United States Patent
Yang et al.

(10) Patent No.: US 11,214,572 B2
(45) Date of Patent: Jan. 4, 2022

(54) 7-SITE SUBSTITUTED PYRROLE TRIAZINE COMPOUNDS OR PHARMACEUTICALLY ACCEPTABLE SALTS THEREOF, AND PREPARATION METHOD THEREOF AND USES THEREOF

(71) Applicant: SHANGHAI INSTITUTE OF MATERIA MEDICA, CHINESE ACADEMY OF SCIENCES, Shanghai (CN)

(72) Inventors: Chunhao Yang, Shanghai (CN); Linghua Meng, Shanghai (CN); Haoyue Xiang, Shanghai (CN); Jing Li, Shanghai (CN); Xi Zhang, Shanghai (CN); Xiang Wang, Shanghai (CN); Cun Tan, Shanghai (CN); Qian He, Shanghai (CN); Jian Ding, Shanghai (CN); Yi Chen, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/626,254

(22) PCT Filed: Jun. 22, 2018

(86) PCT No.: PCT/CN2018/092419
§ 371 (c)(1),
(2) Date: Dec. 23, 2019

(87) PCT Pub. No.: WO2018/233684
PCT Pub. Date: Dec. 27, 2018

(65) Prior Publication Data
US 2020/0157110 A1    May 21, 2020

(30) Foreign Application Priority Data

Jun. 23, 2017  (CN) .......................... 201710493411.2

(51) Int. Cl.
*C07D 487/04*  (2006.01)
*C07D 519/00*  (2006.01)

(52) U.S. Cl.
CPC ......... *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS

2015/0141644 A1   5/2015  Yang et al.
2016/0115166 A1   4/2016  Wu et al.

FOREIGN PATENT DOCUMENTS

| AU | 2013270326 B2 | 12/2013 |
|---|---|---|
| CN | 102675323 A | 9/2012 |
| CN | 103450204 A | 12/2013 |
| EA | 023775 B1 | 7/2016 |
| EP | 2857403 A1 | 4/2015 |
| EP | 3053926 A1 | 8/2016 |
| WO | 2013/177983 | 12/2013 |
| WO | 2017/219800 | 12/2017 |

OTHER PUBLICATIONS

Dugar et al., "Synthesis and evaluation of pyrrolotriazine based molecules as PI3 kinase inhibitors", Bioorganic & Medicinal Chemistry Letters 25 (2015) 3142-3146.
Office Action for Application No. 2018287971, dated Apr. 2020, 3 pages.
Search Report for EP 18820615.5, dated Mar. 20, 2017, 7 pages.
International Search Report for PCT/CN2018/092419, dated Sep. 18, 2018, English translation, 2 pages total.
Office Action issued for India Application No. 202047002922, dated Jul. 14, 2020, 6 pages including English translation.
Office Action for Russia Application No. 2020101594/04(002343), dated Jun. 18, 2020, 18 pages including English translation.
Office Action for Russia Application No. 2020101594/04(002343), dated Oct. 19, 2020, 14 pages including English translation.
Office Action/Written Opinion for Singapore Application No. 11201912827T, dated Sep. 23, 2020, 7 pages.
Office Action for China Application No. CN201710493411.2, dated Jul. 23, 2021, 11 pages including English translation.
Office Action for China Application No. CN201880042091.1, dated Jul. 29, 2021, 11 pages including English translation.
Office Action for Mexico Application No. MXa2019015898, dated Sep. 9, 2021, 11 pages including machine translation.
Office Action/Written Opinion for Singapore Application No. 11201912827T, dated Aug. 25, 2021, 8 pages.

*Primary Examiner* — Paul V Ward
(74) *Attorney, Agent, or Firm* — Adsero IP

(57) ABSTRACT

The present disclosure relates to 7-substituted pyrrolo[2,1-f][1,2,4]triazine compounds or pharmaceutically acceptable salts thereof, and preparation methods and uses thereof. These compounds show good PI3K inhibitory activity, can effectively inhibit the activity of PI3K kinase, and has significant enhancement and improvement of pharmacokinetic properties, such as bioavailability, due to the introduction of the 7-position group; furthermore, the compounds of the present disclosure exhibit an unpredictable high selectivity and strong inhibitory activity on PI3Kδ, and thus these compounds can be used for treating diseases related to PI3K pathway, especially for anti-cancer or for the treatment of tumors, leukemias and autoimmune diseases. After further optimizing and screening, the compounds are expected to be developed into a new type of anti-tumor drugs.

14 Claims, No Drawings

7-SITE SUBSTITUTED PYRROLE TRIAZINE COMPOUNDS OR PHARMACEUTICALLY ACCEPTABLE SALTS THEREOF, AND PREPARATION METHOD THEREOF AND USES THEREOF

CROSS REFERENCE TO RELATED APPLICATIONS

This application is a national stage application for International Application PCT/CN2018/092419, filed on Jun. 22, 2018, which claims the priority benefit of Chinese Patent Application No. 201710493411.2, titled "7-SUBSTITUTED PYRROLOTRIAZINE COMPOUNDS OR PHARMACEUTICALLY ACCEPTABLE SALTS THEREOF, AND PREPARATION METHODS AND USES THEREOF" and filed on Jun. 23, 2017. The entireties of both applications are incorporated by reference herein for all purposes.

TECHNICAL FIELD

The present disclosure relates to the field of medicinal chemistry, and particularly relates to 7-substituted pyrrolotriazine compounds or their pharmaceutically acceptable salts, and preparation methods and uses thereof.

BACKGROUND

PI3K-Akt-mTOR signaling pathway is one of the major pathways that transmits signals from receptor tyrosine kinase and G-protein coupled receptor and plays an important role in a variety of cell functions. Recent studies have found that multiple key node proteins in the PI3K-Akt-mTOR signaling pathway are over activated due to the existence of mutation or amplification of coding genes in a variety of human tumors [Vivancod et al., Nat Rev Cancer 2 (2002), pp. 489-501]. Among them, PI3K, as a bridge molecule connecting extracellular signals and cell response effects, is a key factor that regulates growth, metabolism, and survival of cells, of which over activation is closely related to the occurrence of multiple tumors in humans [Sabbah et al., Curr Med Chem 18 (2011), pp. 5528-5544].

PI3K belongs to intracellular phosphatidylinositol kinase with a phosphatidylinositol kinase activity and a serine/threonine kinase activity. According to different gene series homology, substrate specificity and functions, the PI3K superfamily is mainly divided into three types: type I, type II, and type III [Engelman et al., Nat Rev Genet 7 (2006), pp. 606-619]. Type I PI3K is by far the most widely studied type, this type of PI3K can further be divided into four subtypes: PI3Kα, PI3Kβ, PI3Kδ, and PI3Kγ. Type I PI3K is a heterodimer enzyme consisting of a catalytic subunit of 110 kDa and a regulatory subunit of 85 kDa. Due to difference of regulatory subunits and activation mechanisms, these four subtypes can also be classified into two categories: Class IA, Class IB. Wherein PI3Kα, PI3Kβ, and PI3Kδ belong to Class IA and are activated by receptor tyrosine kinase (RTKs); while PI3Kγ belongs to Class IB and is activated by G-protein coupled receptor. The 3-position of phosphatidylinositol-4,5-phosphate (PIP2) can be phosphorylated by type I PI3K, forming phosphatidylinositol-3,4,5-phosphate (PIP3). As an important second messenger, PIP3 can bind and activate various intracellular target proteins (such as AKT and PDK1) to form a signal cascade complex and ultimately regulate the proliferation, differentiation, survival and migration of cells. The kinase domain of Type II or type III PI3K has a high homology to that of type I PI3K, and Type II and type III PI3Ks have similar phosphorylation functions as type I PI3K. However, the physiological functions of Type II or type III PI3K is poorly understood. Type II PI3K functions as a monomer without regulatory subunit and is divided into three subtypes: PI3KC2α, PI3KC2β, and PI3KC2γ, which is mainly involved in the transporting of intracellular materials, the cell survival and the internalization process of membrane receptor proteins. Type III PI3K, which consists of only one subtype, Vps34 (vacuole protein sorting defective 34), has been widely known for its endocytosis and transport function of Golgi vesicles [Backer, Biochem J 410 (2008), pp. 1-17]. Recent studies have shown that Vps34 plays an important role in the process of cell autophagy [Ma et al., Cell Res 24 (2014), pp. 912-924].

At present, there are dozens of PI3K inhibitors in clinical trials, which can be roughly divided into three categories: non-selective PI3K inhibitors, type I PI3K selective inhibitors and subtype selective type I PI3K inhibitors. From the analysis of existing clinical data, although the non-selective PI3K inhibitors were the earliest candidates which entered into clinical trial, they proceeded slowly due to dose-limiting toxicity. While subtype selective PI3K inhibitors proceeded quickly in clinic trial, especially PI3Kδ inhibitors. The first PI3K inhibitor on the market, Idelalisib, is a PI3Kδ selective inhibitor, and another γ/δ selective inhibitor, Duvelisib, is already in phase III clinical trials [Winkler et al., Chem Biol 20 (2013), pp. 1362-1372]. Among the catalytic subunits of the Class IA, the catalytic subunit p110δ of PI3Kδ, being different from the P110α and P110β which are widely expressed in various tissues throughout the body, is mainly high expressed selectively in the immune system, such as B cells, T cells, etc., closely related to the diseases of hematological malignancy and inflammation, immunity and the like [Fruman et al., N Engl J Med 370 (2014), pp. 1061-1062]. Idelalisib has been approved by the US FDA as a drug for the treatment of three hematologic tumors of recurrent chronic lymphocytic leukemia (CLL), recurrent follicular B-cell non-Hodgkin's lymphoma (FL), and recurrent small lymphocytic lymphoma. This highlights the significance of PI3Kδ inhibitors in the treatment of hematological malignancies.

Currently, the skeletons of the most inhibitors against PI3Kδ are focus on the core scaffold of Idelalisib, for example, US20140121224A1. In contrast, the toxicity of compounds with triazine as the core scaffold was significantly lower than that of Idelalisib based on the available data. Another type core scaffold that has been more studied is thienopyrimidine, whose representative compound is PI3K pan-inhibitor GDC-0941 [Folkes et al., J Med Chem 51 (2008), pp. 5522-5532]. Although thienopyrimidine compounds have been reported as selective PI3K δ inhibitors [Murray et al., J Med Chem 55 (2012), pp. 7866-7695], the core scaffolds thereof are very different from that of pyrrolotriazine in properties. At present, only a few cases of PI3K inhibitors based on pyrrolotriazine as the parent nucleus have been reported, such as those disclosed in CN102675323A, and there have been no reports about the inhibitory activity of PI3Kδ so far.

SUMMARY

Based on this, the object of the present disclosure is to provide 7-substituted pyrrolo[2,1-f][1,2,4]triazine compounds represented by the general formula I or pharmaceutically acceptable salts thereof:

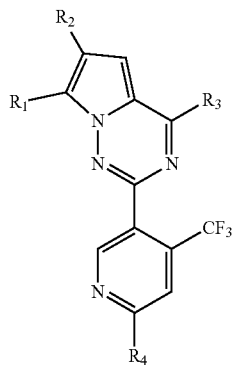

Wherein, $R_1$ is halogen, or $C_{1-6}$ alkyl or $C_{3-8}$ cycloalkyl which is unsubstituted or substituted with at least one substituent, wherein the substituent is halogen;

$R_2$ is: —C(OH)$R_5R_6$; —COC$_{1-6}$ alkyl; —CN; or, unsubstituted or at least one substituent substituted $C_{1-6}$ alkyl, —CH$_2$NH—C$_{1-6}$ alkyl, —CH$_2$N(C$_{1-6}$ alkyl) (C$_{1-6}$ alkyl), —CH$_2$-(saturated heterocyclyl containing 1 to 2 heteroatoms and 3 to 6 carbon atoms), —CH$_2$-(saturated heterocyclyl containing 1 to 2 heteroatoms and 3 to 6 carbon atoms)-(saturated heterocyclyl containing 1 to 2 heteroatoms and 3 to 6 carbon atoms), —CH$_2$-(saturated spirocyclic group containing 1 to 2 heteroatoms and 4 to 12 carbon atoms), —CH$_2$-(saturated bridged ring group containing 1 to 2 heteroatoms and 3 to 12 carbon atoms)-(saturated heterocyclyl containing 1 to 2 heteroatoms and 3 to 6 carbon atoms), or —CH$_2$-(saturated bridged ring group containing 1 to 2 heteroatoms and 3 to 12 carbon atoms), wherein the substituent is halogen, —N(C$_{1-4}$ alkyl)(C$_{1-4}$ alkyl), —O—C$_{1-4}$ alkyl, —CN, —COOH, —CHO, —NHS(O)$_2$—C$_{1-4}$ alkyl, —N(C$_{1-4}$ alkyl)C(C$_{1-4}$ alkyl)(C$_{1-4}$ alkyl)-CONH$_2$, =O, —OH, —S(O)$_2$N(C$_{1-4}$ alkyl)(C$_{1-4}$ alkyl), —S—C$_{1-4}$ alkyl, —S(O)$_2$—C$_{1-4}$ alkyl, —CO—C$_{3-6}$ cycloalkyl, oxetanyl, morpholinyl, C$_{3-6}$ cycloalkyl, —C$_{1-4}$ alkyl-N(C$_{1-4}$ alkyl) (C$_{1-4}$ alkyl), C$_{1-4}$ alkyl-O—C$_{1-4}$ alkyl which is unsubstituted or substituted with at least one methyl, —CONH$_2$ which is unsubstituted or substituted with at least one methyl, C$_{1-4}$ alkyl-CONH$_2$ which is unsubstituted or substituted with at least one methyl, —COO—C$_{1-4}$ alkyl which is unsubstituted or substituted with at least one methyl, —NH$_2$ which is unsubstituted or substituted with at least one methyl, —NHCO—C$_{1-4}$ alkyl which is unsubstituted or substituted with at least one methyl, —CO—C$_{1-4}$ alkyl which is unsubstituted or substituted with at least one substituent A, wherein the substituent A is hydroxyl or methyl, or C$_{1-4}$ alkyl which is unsubstituted or substituted with at least one substituent B, wherein the substituent B is —NH$_2$, —OCH$_3$, —CONH$_2$, —OH or —CF$_3$.

In $R_2$, the heteroatom is selected from at least one of N, O and S, $R_5$ and $R_6$ are each independently hydrogen or $C_{1-6}$ alkyl; $R_3$ is

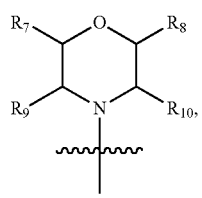

wherein $R_7$, $R_8$, $R_9$ and $R_{10}$ are each independently hydrogen or $C_{1-6}$ alkyl which is unsubstituted or substituted with at least one substituent, wherein the substituent is halogen or hydroxyl;

$R_4$ is —NH$_2$, —NHCONHR$_{11}$ or —NHCO$_2$R$_{12}$, wherein $R_{11}$ and $R_{12}$ are each independently $C_{1-6}$ alkyl, $C_{3-8}$ cycloalkyl or phenyl which is unsubstituted or substituted with at least one substituent selected from at least one of halogen and —C(O)OR$_{13}$, wherein $R_{13}$ is $C_{1-6}$ alkyl which is unsubstituted or substituted with at least one substituent, the substituent in the $R_{13}$ is halogen.

In one embodiment, $R_1$ is halogen, or $C_{1-4}$ alkyl or $C_{3-6}$ cycloalkyl which is unsubstituted or substituted with at least one substituent.

In one embodiment, $R_1$ is —Cl, —F, methyl, trifluoromethyl or difluoromethyl.

In one embodiment, $R_2$ is: —C(OH)$R_5R_6$; —COC$_{1-4}$ alkyl; —CN; or, unsubstituted or at least one substituent substituted $C_{1-4}$ alkyl, —CH$_2$NH—C$_{1-4}$ alkyl, —CH$_2$N(C$_{1-4}$ alkyl)(C$_{1-4}$ alkyl), —X-(saturated four- to six-membered heterocyclyl containing 1 to 2 heteroatoms), —X-(saturated four- to six-membered heterocyclyl containing 1 to 2 heteroatoms)-(saturated four- to six-membered heterocyclyl containing 1 to 2 heteroatoms), —X-(saturated spiro-bicyclic group containing 1 to 2 heteroatoms and 4 to 8 carbon atoms), —X-(saturated bicyclic bridged ring group containing 1 to 2 heteroatoms and 3 to 8 carbon atoms)-(saturated four- to six-membered heterocyclyl containing 1 to 2 heteroatoms), or —X-(saturated bicyclic bridged ring group containing 1 to 2 heteroatoms and 3 to 8 carbon atoms), wherein X is CH$_2$, and wherein the heterocyclyl, spirocyclic group and bridged ring group are connected to X via an N atom, $R_5$ and $R_6$ are each independently hydrogen or $C_{1-4}$ alkyl.

In one embodiment, $R_5$ and $R_6$ are each independently hydrogen, methyl or ethyl.

In one embodiment, the substituent in $R_2$ is —F, —Cl, —Br, —I, —CH$_3$, —CH$_2$CH$_3$, —CH$_2$CH(CH$_3$)$_2$, —CH$_2$NH$_2$, —CH$_2$N(CH$_3$)$_2$, —CH$_2$CH$_2$NH$_2$, —CH$_2$CH$_2$N(CH$_3$)$_2$, —CH$_2$OH, —CH$_2$OCH$_3$, —CH$_2$CH$_2$OH, —C(CH$_3$)$_2$OH, —C(CH$_3$)(CF$_3$)OH, —C(CF$_3$)$_2$OH, —C(CH$_3$)$_2$OCH$_3$, —C(CH$_3$)$_2$NH$_2$, —CH$_2$C(CH$_3$)$_2$OH, —CH(OH)CH(CH$_3$)$_2$, —C(CH$_3$)$_2$CH$_2$OH, —C(CH$_3$)$_2$CH$_2$OCH$_3$, —CN, —CF$_3$, —CO$_2$H, —CHO, —COCH$_3$, —CO$_2$CH$_3$, —CO$_2$C(CH$_3$)$_3$, —COCH$_2$OH, —COC(OH)(CH$_3$)$_2$, —COCH(OH)CH$_3$, —CONH$_2$, —CONHCH$_3$, —CON(CH$_3$)$_2$, —CH$_2$CONH$_2$, —CH$_2$CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, =O, —OH, —OCH$_3$, —S(O)$_2$N(CH$_3$)$_2$, —SCH$_3$, —S(O)$_2$CH$_3$, —C(O)-cyclopropyl, cyclopropyl, cyclobutyl, oxetanyl or morpholinyl.

In one embodiment, $R_2$ is

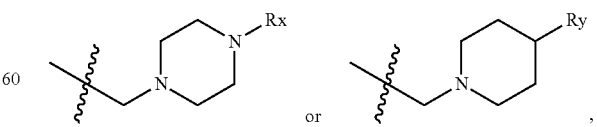

Rx and Ry are each —N(CH$_3$)$_2$, —S(O)$_2$CH$_3$ or $C_{1-4}$ alkyl, wherein the $C_{1-4}$ alkyl is unsubstituted or substituted with at least one substituent, the substituent is halogen, hydroxyl, —CONH$_2$, —CF$_3$, amino or —OCH$_3$.

In one embodiment, R₂ is

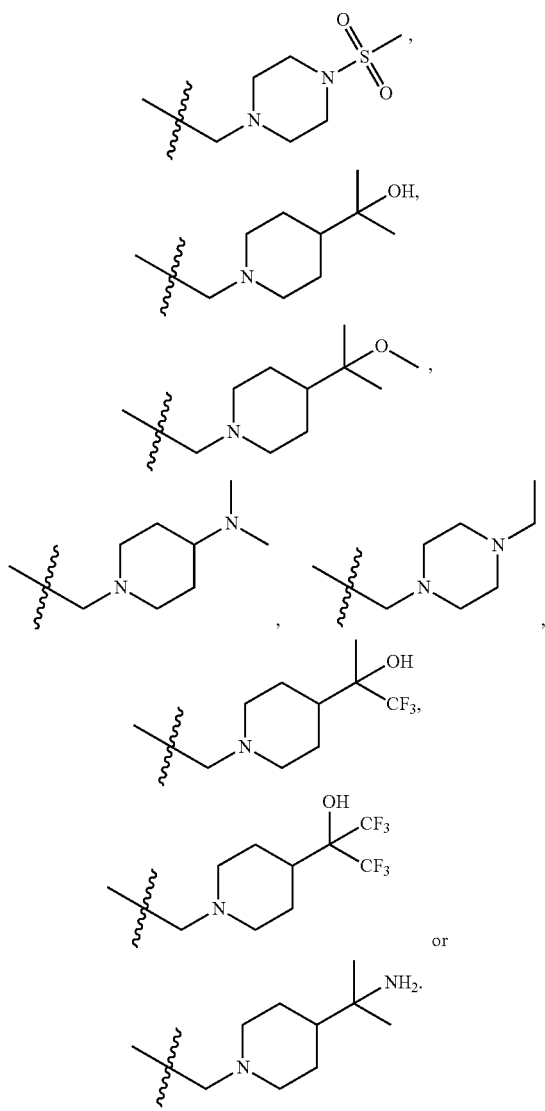

In one embodiment, R₃ is

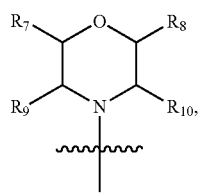

wherein $R_7$, $R_8$, $R_9$, $R_{10}$ are each independently hydrogen or $C_{1-4}$ alkyl.

In one embodiment, $R_7$, $R_8$, $R_9$ and $R_{10}$ are each independently H or methyl.

In one embodiment, $R_3$ is morpholinyl or (S)-3-methylmorpholinyl.

In one embodiment, $R_4$ is —NH₂, —NHCONHR₁₁ or —NHCO₂R₁₂, wherein R₁₁ and R₁₂ are each independently $C_{1-4}$ alkyl, $C_{3-6}$ cycloalkyl or phenyl which is unsubstituted or substituted with at least one substituent selected from at least one of fluoro, chloro, bromo and —C(O)OR₁₃, wherein R₁₃ is $C_{1-4}$ alkyl.

In one embodiment, R₁₁ and R₁₂ are each independently methyl, ethyl, isopropyl, cyclopropyl, phenyl, -Ph-CO₂Et-p or 4-fluorophenyl.

The 7-substituted pyrrolo[2,1-f][1,2,4]triazine compound represented by the general formula I or a pharmaceutically acceptable salt thereof, for example, has a structure represented by one of the following general formulas:

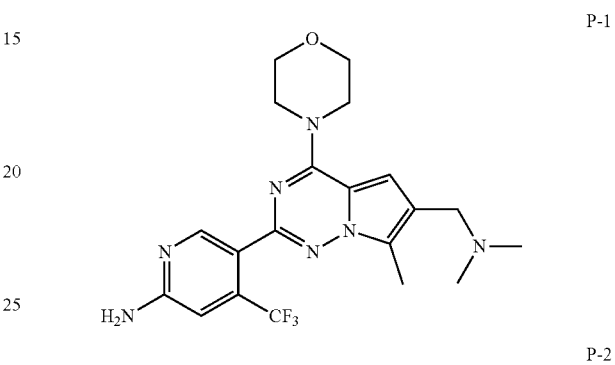

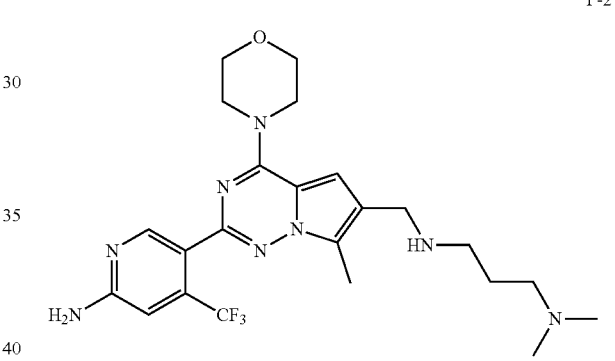

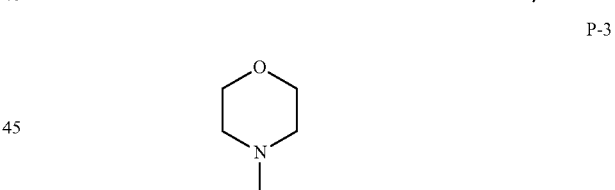

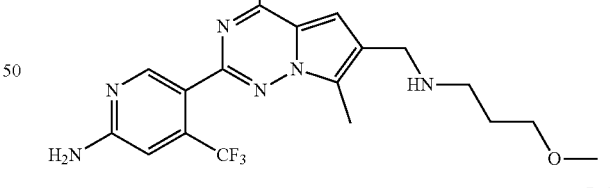

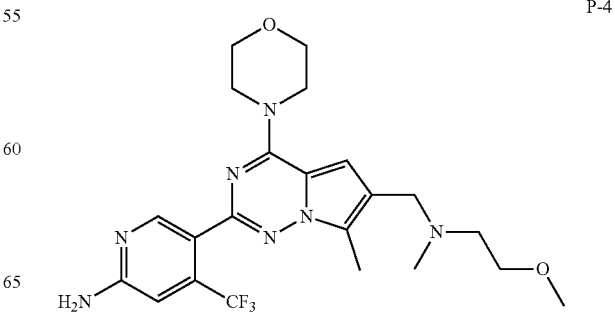

P-5
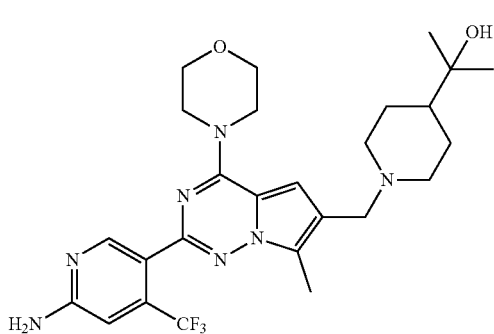
P-6
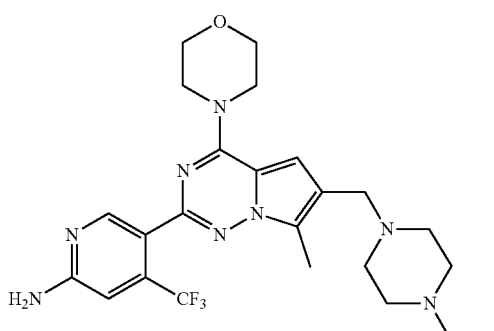
P-7
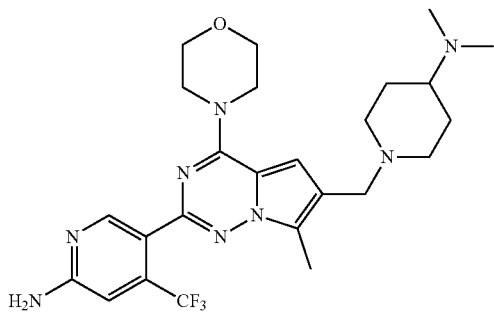
P-8
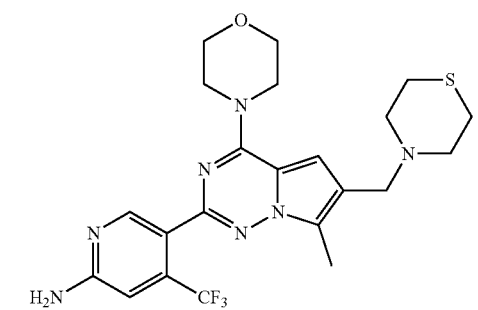
P-9
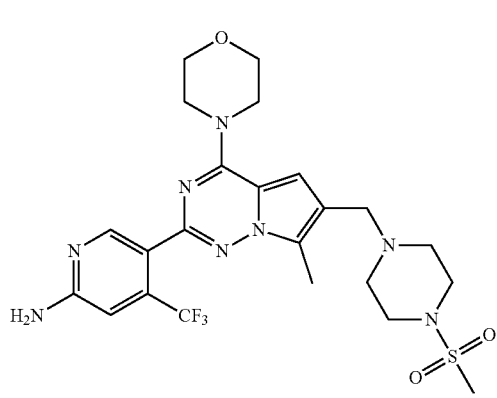
P-10
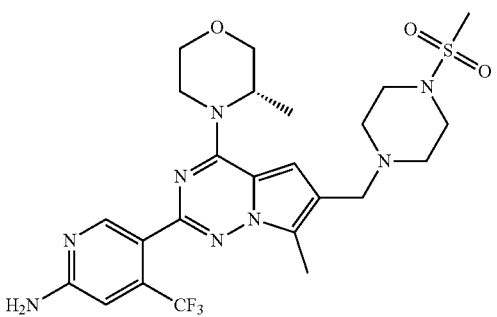
P-11
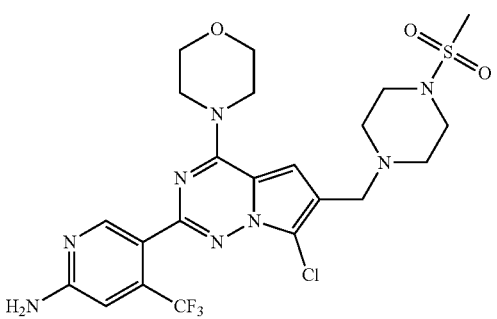
P-12
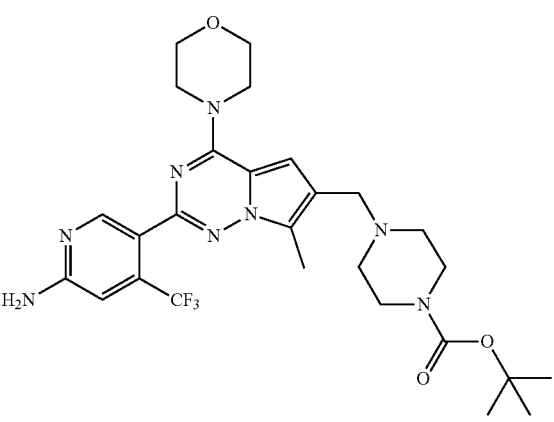

P-13
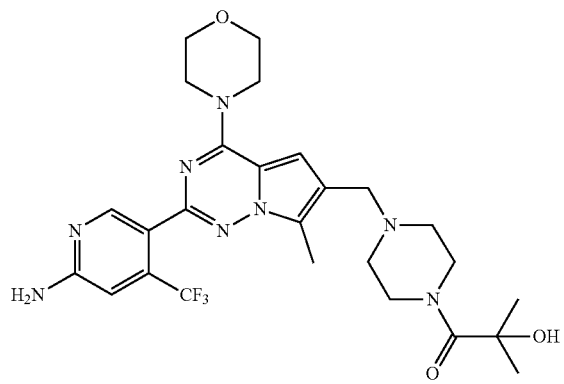
P-14
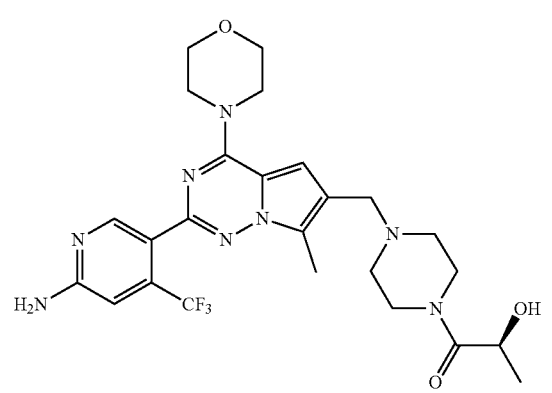
P-15
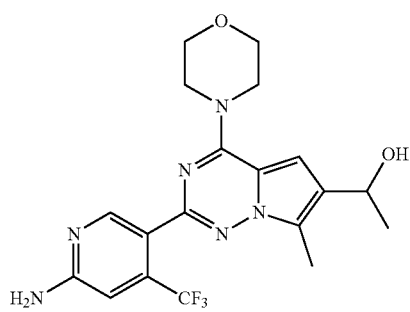
P-16
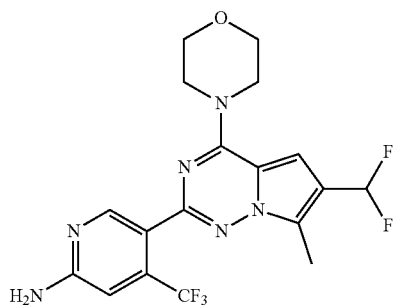
P-17
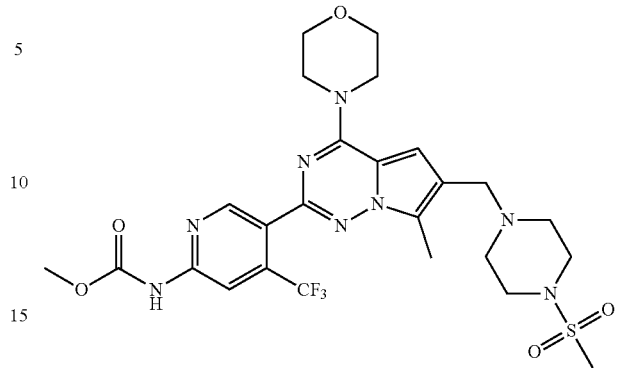
P-18
P-19
P-20
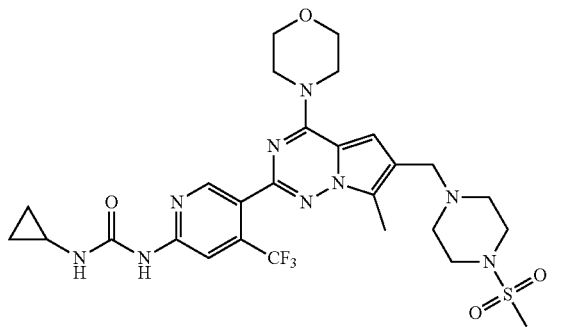

-continued
P-21
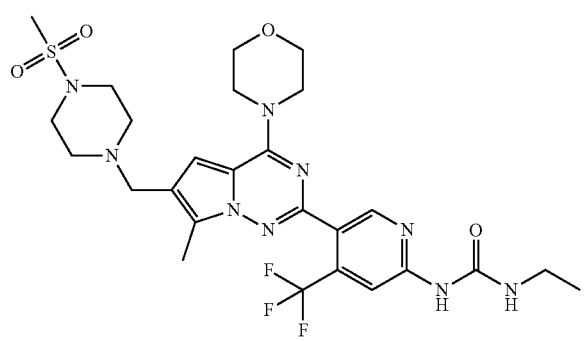
P-22
P-23
R = p-F-Ph
P-24
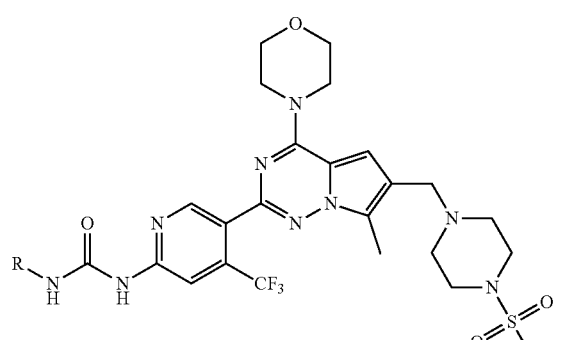
R = p-EtOCOPh
-continued
P-25
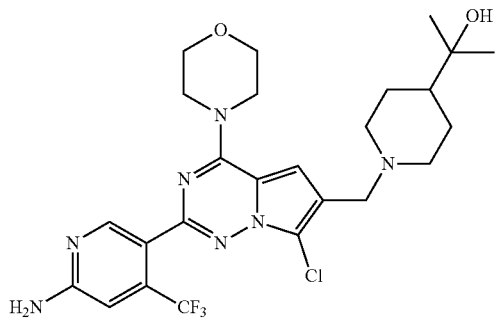
P-26
P-27
P-28
P-29

P-30
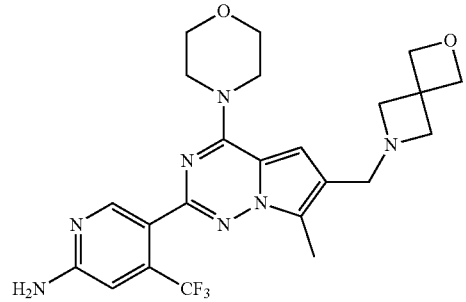
P-31
P-32
P-33
P-34
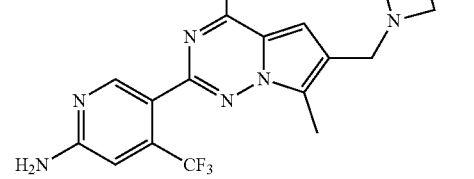
P-35
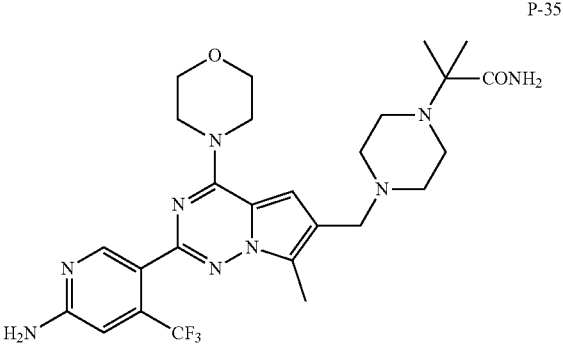
P-36
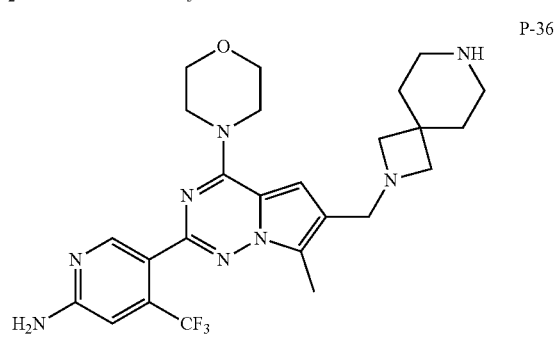
P-37
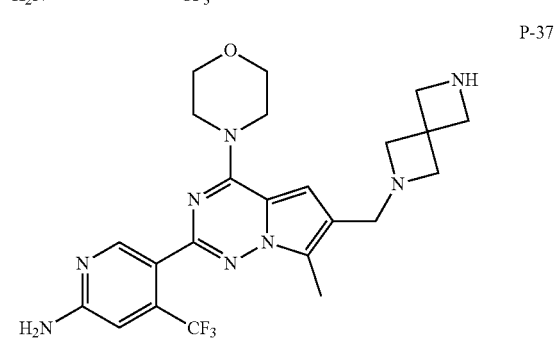
P-38
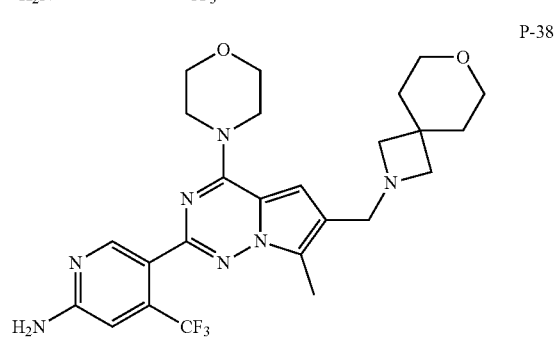
P-39
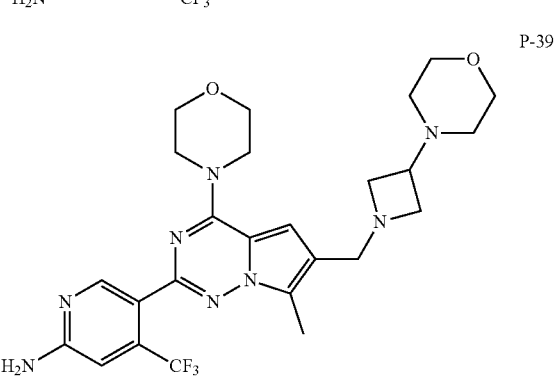

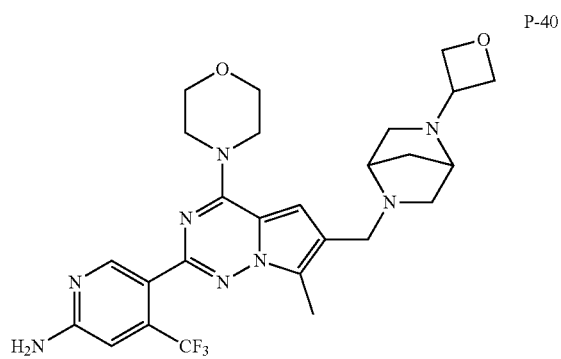

P-40

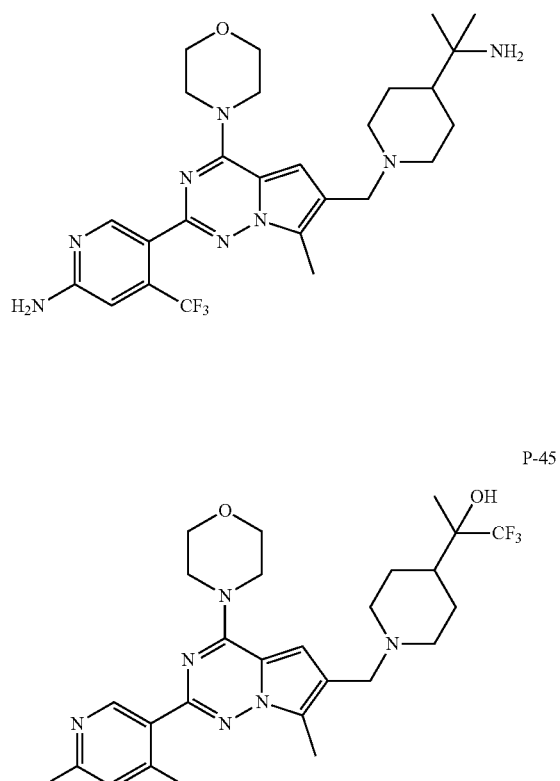

P-44

P-45

P-46

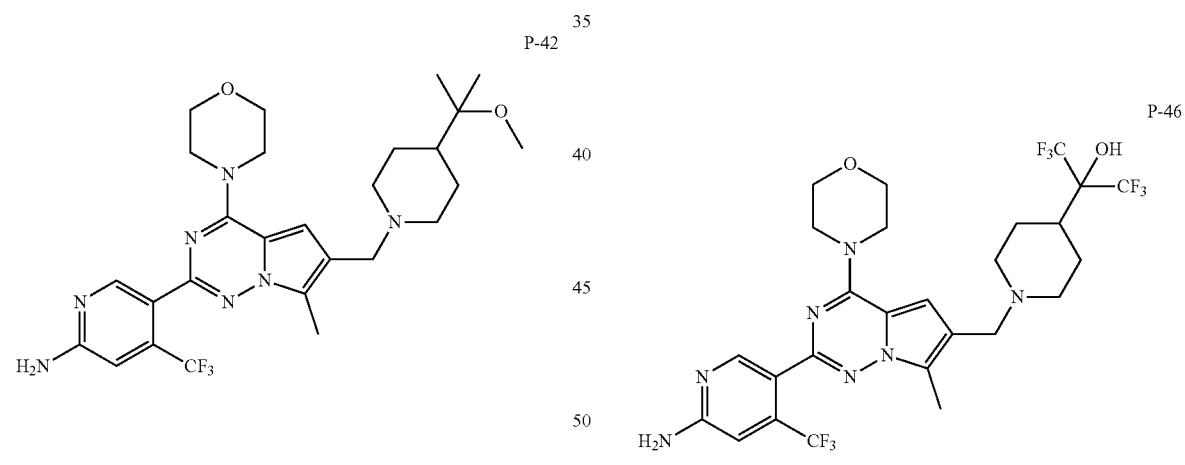

P-41

P-42

P-43

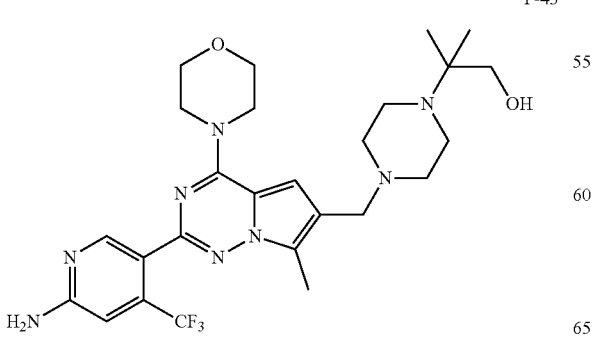

The pharmaceutically acceptable salts include organic acid salts and inorganic acid salts, including but not limited to maleate, succinate, citrate, tartrate, fumarate, acetate, mesylate, hydrochloride, phosphate, nitrate or sulfate.

Another object of the present disclosure is to provide a preparation method of the 7-substituted pyrrolo[2,1-f][1,2,4]triazine compound represented by the general formula I, which is prepared by the following route:

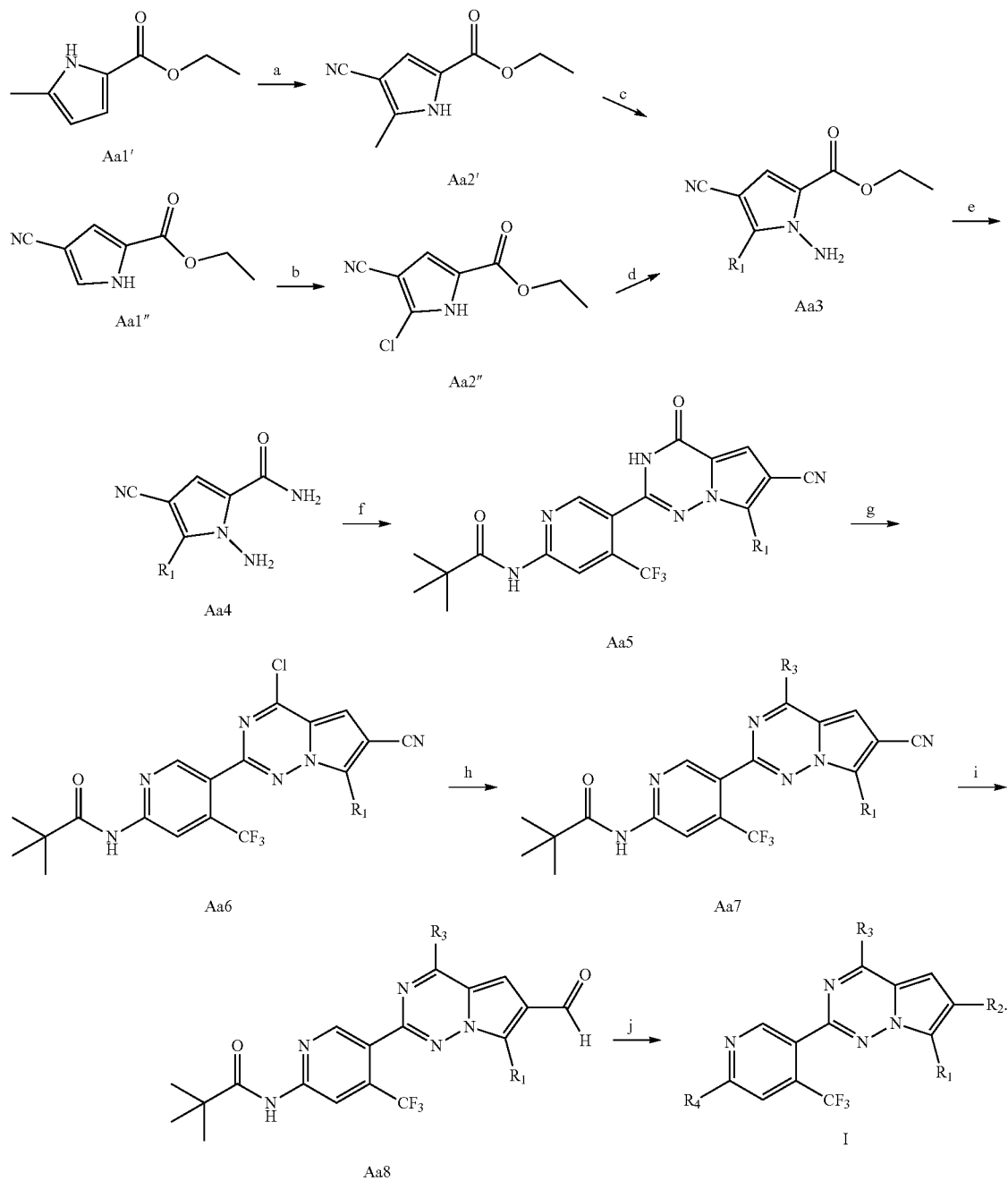

Furthermore, the reagents and conditions required for each step include:

step a: adding chlorosulfonyl isocyanate dropwise to a solution of compound Aa1' and dimethylformamide (DMF) in anhydrous acetonitrile, and reacting to obtain a compound Aa2', or step b: dissolving a compound Aa1" in chloroform and adding N-chlorosuccinimide for reaction to obtain a compound Aa2";

step c: adding 5% wt of sodium hypochlorite solution to a solution of the compound Aa2', $K_2CO_3$, $NH_4Cl$, concentrated aqueous ammonia and methyltrioctyl ammonium chloride in methyl tert-butyl ether, and reacting to obtain a compound Aa3, or step d: dissolving a compound Aa2" in anhydrous dimethylformamide, adding NaH, stirring, and then adding O-(2,4-dinitrophenyl)-hydroxylamine, reacting to obtain a compound Aa3;

Step e: dissolving the compound Aa3 in a saturated methanolic ammonia solution or a solution of ammonia in methanol, and reacting to obtain a compound Aa4;

Step f: mixing the compound Aa4 with aldehyde, anhydrous copper chloride and dimethylsulfoxide, and reacting to obtain a compound Aa5;

Step g: adding phosphorus oxychloride to a mixture of the compound Aa5 and N, N-dimethylaminopyridine or dimethylaminopyridine, and reacting to obtain a compound Aa6;

Step h: adding anhydrous tetrahydrofuran and morpholine to the compound Aa6, and reacting to obtain a compound Aa7;

Step i: adding Raney nickel to a suspension of the compound Aa7 and sodium hypophosphite monohydrate in acetic acid/water/pyridine, and reacting to obtain a compound Aa8; and Step j: suspending the compound Aa8, sodium cyanoborohydride and amine in methanol, adding acetic acid, and reacting to obtain a product; or step j: adding methyl magnesium bromide to a solution of the compound Aa8 in anhydrous tetrahydrofuran, and reacting to obtain a product; or step j: adding diethylaminosulfur trifluoride (DAST) to a solution of the compound Aa8 in anhydrous dichloromethane, and reacting to obtain a product.

In one embodiment, compound P-28 is prepared by the following route:

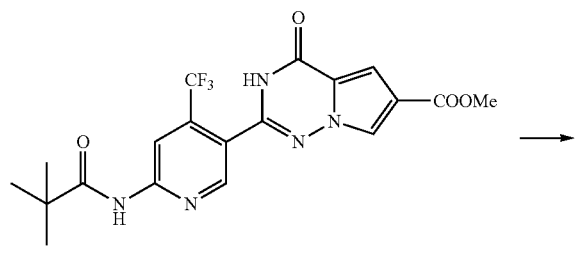

P-28-1

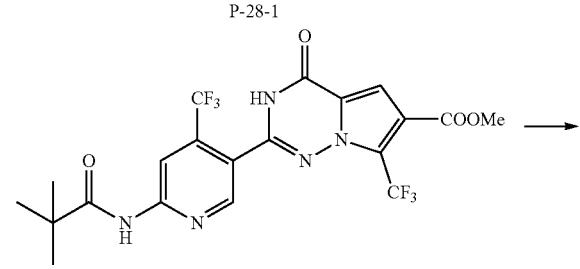

P-28-2

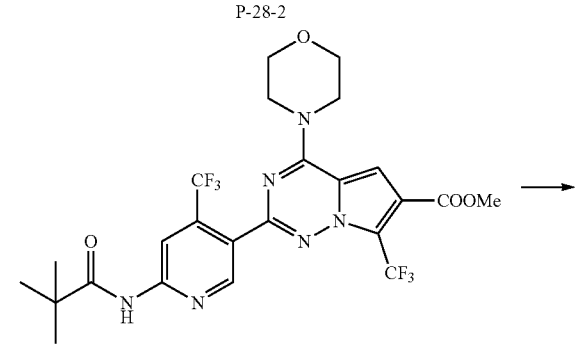

P-28-3

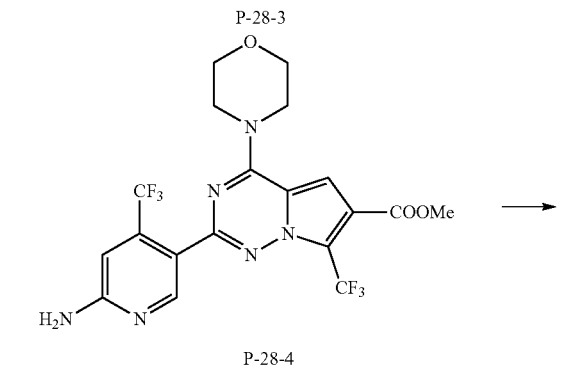

P-28-4

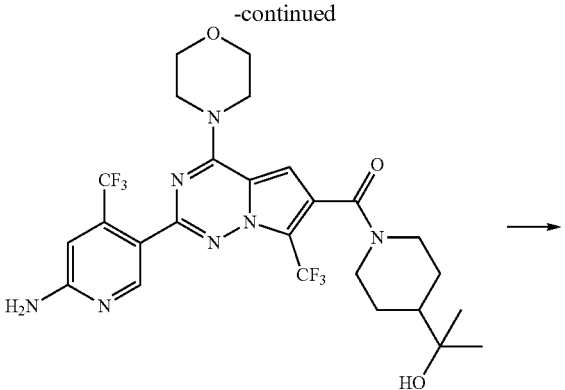

P-28-5

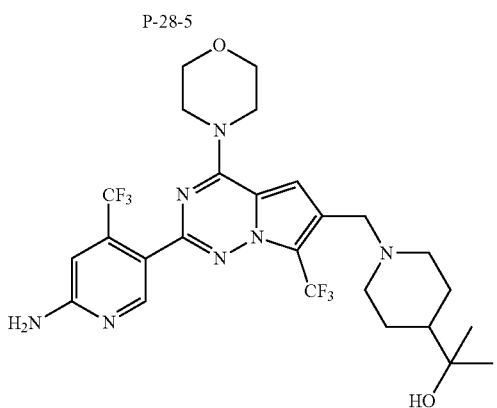

P-28

Specifically comprising the following steps:

step 1: dissolving compound P-28-1 in a mixture of dichloromethane and water, then adding sodium trifluoromethylsulfinate, cooling the above system and slowly adding 70% aqueous solution of tert-butyl hydroperoxide dropwise, then adding dimethyl sulfoxide and warming the reaction to obtain a compound P-28-2;

step 2: adding the compound P-28-2 and phosphorus oxychloride to toluene, then adding N, N-dimethylaniline, reacting at reflux to obtain a crude chlorinated compound, dissolving the crude chlorinated compound in anhydrous tetrahydrofuran, and adding morpholine at 0° C., stirring at room temperature until reacting the raw materials completely, then concentrating to obtain a crude product, which is used directly in the next reaction;

step 3: dissolving the crude product obtained from step 2 in methanol, then adding water and sodium hydroxide, reacting at reflux until the raw materials are completely disappeared, concentrating, adding water and adjusting the pH value to precipitate a solid, drying, and then using it directly in the next reaction;

step 4: adding the crude product from step 3, benzotriazole-N, N, N', N'-tetramethyluronium hexafluorophosphate (HBTU), triethylamine and 2-(4-piperidyl)-2-propanol to N, N-dimethylformamide (DMF), and reacting to obtain a compound P-28-5; and step 5: dissolving the P-28-5 in anhydrous tetrahydrofuran, then slowly adding borane/tetrahydrofuran (BH$_3$/THF) dropwise. After completing dropwise addition, warming the reaction system to react, then cooling the reaction system and slowly adding concentrated hydrochloric acid dropwise, and after completing dropwise addition, warming the reaction to obtain a compound P-28.

Another object of the present disclosure is to provide the use of the 7-substituted pyrrolo[2,1-f][1,2,4]triazine compound represented by the general formula I or its pharmaceutically acceptable salt thereof in the preparation of an active inhibitor of PI3K.

In one embodiment, the PI3K inhibitor has a selective inhibitory effect on PI3Kδ.

In one embodiment, the PI3K inhibitor is used in a medicament for treating diseases related to PI3K signal pathway.

Preferably, the diseases related to the PI3K signal pathway include tumors, leukemias, and autoimmune diseases.

Additionally, the present disclosure provides a pharmaceutical composition, comprising a therapeutically effective amount of the 7-substituted pyrrolo[2,1-f][1,2,4]triazine compound represented by the general formula I or a pharmaceutically acceptable salt thereof, the pharmaceutical composition is used for treating diseases related to the PI3K signal pathway.

The inventors of the present disclosure have obtained a new type of 7-substituted pyrrolo[2,1-f][1,2,4]triazine compounds by reasonable design and overall consideration of the pharmacokinetic factors of compounds. These compounds show a better PI3K inhibitory activity and effectively inhibit the activity of PI3K kinase. They have significant improvement of pharmacokinetic properties, such as bioavailability, due to the introduction of the 7-position group; furthermore, the compounds of the present disclosure exhibit an unpredictable high selectivity and strong inhibitory activity on PI3Kδ, and thus these compounds can be used for treating diseases related to PI3K signal pathway, especially for anti-cancer or for the treatment of tumors, leukemias and autoimmune diseases. After further optimizing and screening, these compounds are expected to be developed into a new type of anti-tumor drugs.

DETAILED DESCRIPTION OF EMBODIMENTS

The term "alkyl" described herein refers to a straight alkyl or branched alkyl.

The term "substitute" or the like described herein refers to substituting one or more hydrogen atoms. The halogen herein may be selected from at least one of F, Cl, Br and I, preferably at least one of F and Cl.

The present disclosure will be further described below with reference to the embodiments, but these embodiments are by no means a limitation to the present disclosure. In all examples, $^1$H NMR was recorded by Brucher AM-400 and GEMINI-300 nuclear magnetic resonance spectrometer, and chemical shifts were expressed in δ (ppm); mass spectra were recorded by MAT-95 mass spectrometer; the silica gel for separation was 200-300 mesh.

Step a: Preparation of ethyl 4-cyano-5-methyl-1H-pyrrole-2-carboxylate (Aa2')

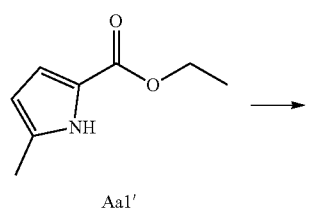

Aa1'

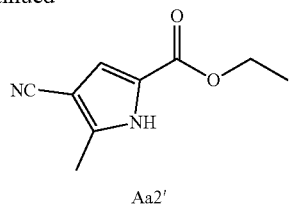

Aa2'

To a solution of compound Aa1' (1.0 g, 6.5 mmol) and DMF (1.3 mL) in anhydrous acetonitrile (20 mL) in an ice bath was added dropwise chlorosulfonyl isocyanate (0.7 mL, 8.0 mmol), then the mixture was moved to room temperature and reacted overnight. The reaction was quenched with saturated sodium carbonate solution (20 mL), diluted with water, then extracted twice with ethyl acetate (50 mL), the organic layers were combined, washed once with saturated brine (100 mL) and dried over anhydrous sodium sulfate, and then concentrated under reduced pressure to give a crude product, which was then purified by chromatographic column (petroleum ether/ethyl acetate: 3/1) to give a white compound (980 mg, 84%).

$^1$H NMR (300 MHz, CDCl$_3$) δ10.07 (br s 1H), 7.03 (d, J=2.53 Hz, 1H), 4.34 (q, J=7.13 Hz, 2H), 2.47 (s, 3H), 1.37 (t, J=7.13 Hz, 3H).

Step c: Preparation of ethyl 1-amino-4-cyano-5-methyl-1H-pyrrole-2-carboxylate (Aa3')

To a solution of compound Aa2' (200 mg, 1.1 mmol), K$_2$CO$_3$ (840 mg, 6.0 mmol), NH$_4$Cl (385 mg, 7.2 mmol), concentrated aqueous ammonia (1.2 mL) and methyltrioctyl ammonium chloride (0.010 mL) in methyl tert-butyl ether (50 mL) in an ice salt bath was added dropwise 5% (mass percentage) sodium hypochlorite solution (12 mL) via a constant pressure dropping funnel, then the mixture was moved to room temperature and reacted for 4 hours. The reaction was quenched with saturated sodium thiosulfate, the methyl tert-butyl ether layer was separated and the aqueous layer was extracted once with ethyl acetate (50 mL), then the organic layers were combined, washed three times with water and dried over anhydrous sodium sulfate, and then concentrated under reduced pressure to give a crude product. The crude product was purified by chromatographic column (petroleum ether/ethyl acetate: 4/1) to give a colorless liquid (183 mg, 86%), which then solidified after standing.

1H NMR (300 MHz, CDCl$_3$) δ 7.01 (s, 1H), 5.46 (s, 2H), 4.30 (q, J=7.13 Hz, 2H), 2.42 (s, 3H), 1.35 (t, J=7.13 Hz, 3H).

Step e: Preparation of 1-amino-4-cyano-5-methyl-1H-pyrrole-2-carboxamide (Aa4')

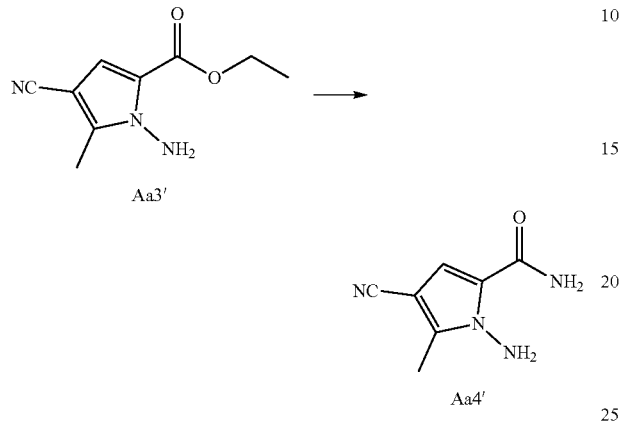

The compound Aa3' (800 mg, 4.1 mmol) was dissolved in 100 mL of saturated methanolic ammonia solution or solution of ammonia in methanol, the mixture reacted at 80° C. for 2 days in a sealed tube, then cooled to room temperature, and concentrated to give a yellow solid (680 mg, 100%).

$^1$H NMR (300 MHz, DMSO-d$_6$) δ 8.01 (br s, 1H), 7.39 br (s, 1H), 7.02 (s, 1H), 6.70 (br s, 2H), 2.27 (s, 3H).

Step b: Preparation of ethyl 4-cyano-5-chloro-1H-pyrrole-2-carboxylate (Aa2")

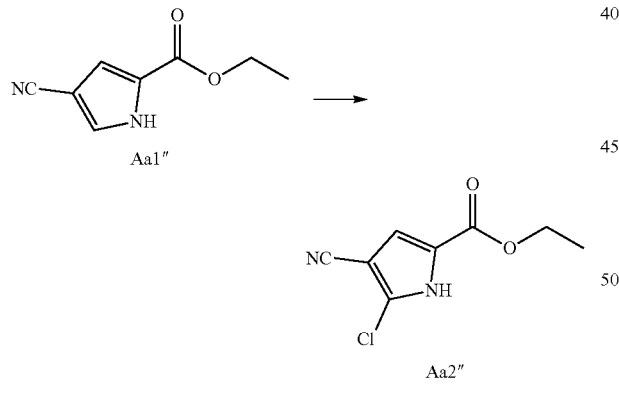

The compound Aa1" (2.0 g, 12.2 mmol) was dissolved in chloroform, and N-chlorosuccinimide (2.0 g, 15.0 mmol) was added, then the mixture was stirred overnight at room temperature; the mixture was diluted with water (100 mL), the organic layer was separated and the aqueous layer was extracted twice with chloroform (100 mL), then the organic phases were combined, washed once with saturated brine (100 mL), dried over anhydrous sodium sulfate, and then concentrated under reduced pressure to give a crude product, which was then purified by chromatographic column (petroleum ether/ethyl acetate: 20/1) to give a white solid (510 mg, 22%).

$^1$H NMR (300 MHz, CDCl$_3$) δ 10.68 (s, 1H), 7.09 (d, J=2.8 Hz, 1H), 4.39 (q, J=7.1 Hz, 2H), 1.39 (t, J=7.2 Hz, 3H).

Step d: Preparation of ethyl 1-amino-4-cyano-5-chloro-1H-pyrrole-2-carboxylate (Aa3")

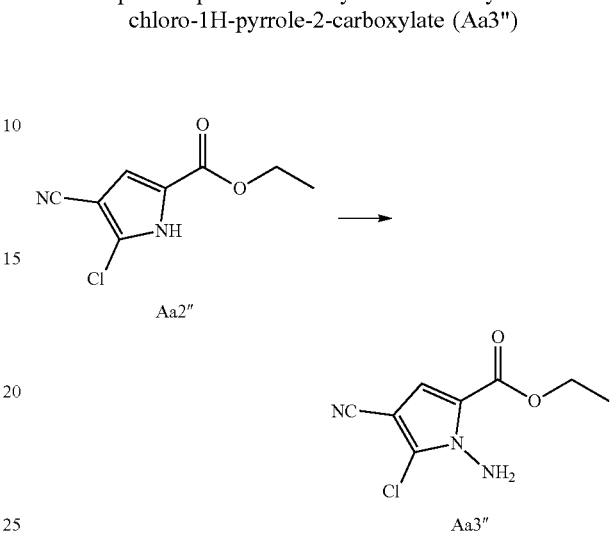

The compound Aa2" (300 mg, 1.5 mmol) was dissolved in anhydrous DMF (10 mL), then NaH (60%, dispersed in mineral oil, 75 mg, 1.9 mmol) was added in an ice bath, after continuing stirring the mixture for 30 minutes, O-(2,4-dinitrophenyl)-hydroxylamine (360 mg, 1.8 mmol) was added, and the mixture was stirred at room temperature for 6 hours. Then the reaction solution was poured into water (50 mL), extracted twice with ethyl acetate (50 mL), the organic layers were combined, washed once with saturated brine (100 mL), dried over anhydrous sodium sulfate, concentrated and then subjected to column chromatography (petroleum ether/ethyl acetate: 10/1) to give a white solid (305 mg, 95%).

$^1$H NMR (300 MHz, CDCl$_3$) δ 7.09 (s, 1H), 5.80 (s, 2H), 4.34 (q, J=7.1 Hz, 2H), 1.37 (t, J=7.1 Hz, 3H).

Step e: Preparation of 1-amino-4=cyano-5-chloro-1H-pyrrole-2=carboxamide (Aa4")

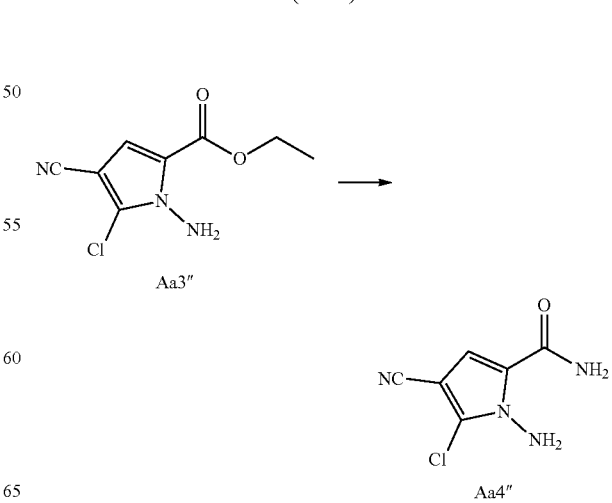

Using compound Aa3" (350 mg, 1.6 mmol) as a raw material to perform a preparation process with reference to that of compound Aa4', a yellow solid (290 mg, 100%) was obtained.

¹H NMR (300 MHz, DMSO-d₆) δ 8.12 (br s, 1H), 7.63 (br s, 1H), 7.19 (s, 1H), 6.86 (br s, 2H).

Step f: Synthesis of Compound Aa5

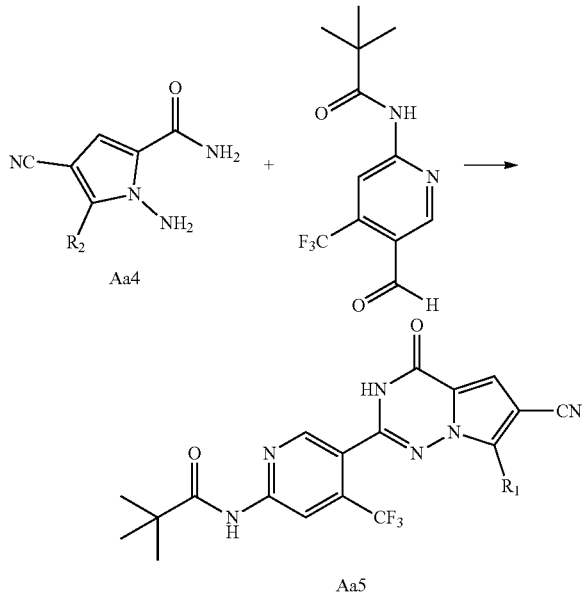

A solution of compound Aa4 (1.0 equiv.), N-(5-formyl-4-(trifluoromethyl) pyridyl-2-)pivalamide (1.2 equiv., prepared by our research group) and anhydrous copper chloride (1.0 equiv.) in dimethylsulfoxide was warmed to 100° C. for reaction. After the reaction was completed, the reaction mixture was cooled, poured into water, and extracted three times with ethyl acetate. The organic layers were combined, washed once with saturated brine and dried over anhydrous sodium sulfate, concentrated and then purified by column chromatography (dichloromethane/methanol: 50/1) to give a yellow solid.

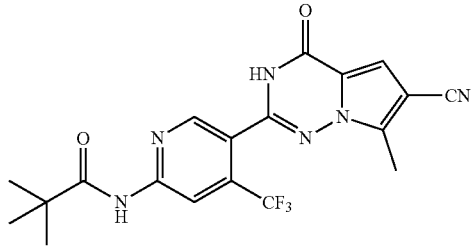

Aa5'

Compound Aa4' (600 mg, 3.7 mmol), the corresponding aldehyde (1.2 g, 4.4 mmol), anhydrous copper chloride (490 mg, 3.7 mmol), dimethylsulfoxide (25 mL); to give a yellow solid (1.3 g, 85%).

¹H NMR (300 MHz, CDCl₃) δ 8.82 (s, 1H), 8.62 (s, 1H), 8.43 (br s, 1H), 7.27 (s, 1H), 2.60 (s, 3H), 1.38 (s, 9H).

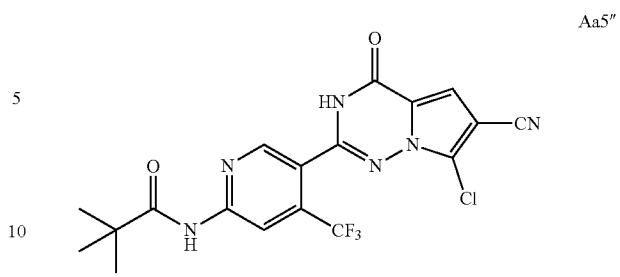

Aa5"

Compound Aa4" (200 mg, 1.1 mmol), the corresponding aldehyde (362 mg, 1.3 mmol), anhydrous copper chloride (150 mg, 1.1 mmol), dimethylsulfoxide (15 mL); to give a yellow solid (408 mg, 85%).

¹H NMR (300 MHz, CDCl₃) δ 8.80 (s, 1H), 8.62 (s, 1H), 8.41 (s, 1H), 7.36 (s, 1H), 1.38 (s, 9H).

Steps g and h: Synthesis of Compound Aa7

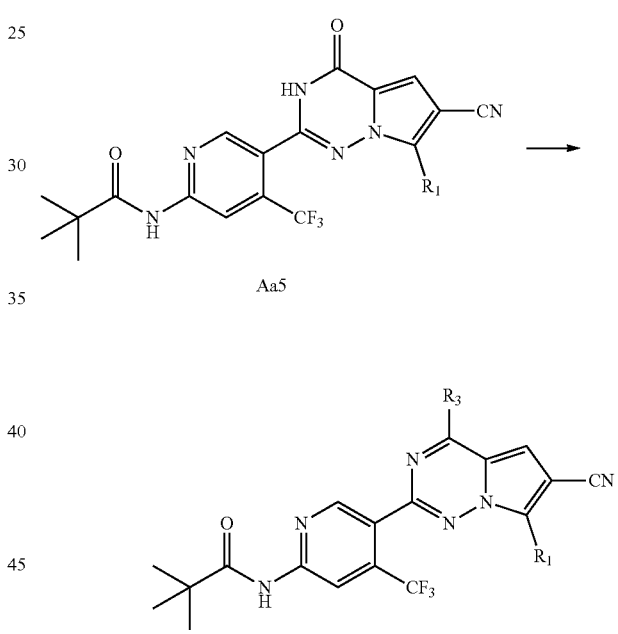

To a mixture of compound Aa5 (1.0 equiv.) and 4-dimethylaminopyridine (2.0 equiv.) was added phosphorus oxychloride and refluxed for 10 hours. After the mixture was cooled, the phosphorus oxychloride was removed under reduced pressure, then anhydrous tetrahydrofuran and morpholine were sequentially added, and then the mixture was refluxed for 2 hours. Tetrahydrofuran was distilled off under reduced pressure, water was added, then the mixture was extracted with ethyl acetate and washed once in turn with saturated brine and water, dried over anhydrous sodium sulfate, concentrated and then purified by column chromatography (petroleum ether/ethyl acetate: 4/1) to give a white solid.

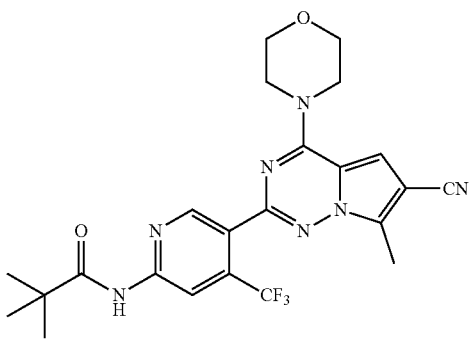

Aa7'

Compound Aa5' (1.0 g, 2.4 mmol), 4-dimethylaminopyridine (583 mg, 4.8 mmol), phosphorus oxychloride (20 mL), tetrahydrofuran (100 mL), morpholine (5 mL); to give a white solid (980 mg, 84%).

$^1$H NMR (300 MHz, CDCl$_3$) δ 8.76 (s, 1H), 8.72 (s, 1H), 8.24 (br s, 1H), 6.99 (s, 1H), 4.06 (t, J=4.77 Hz, 4H), 3.84 (t, J=4.73 Hz, 4H), 2.65 (s, 3H), 1.36 (s, 9H).

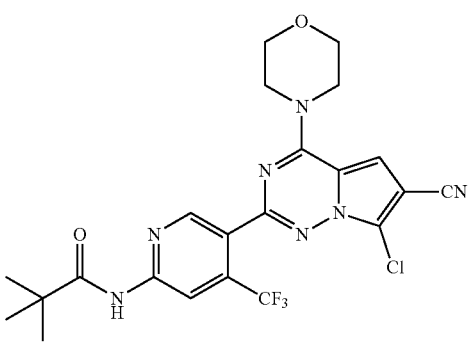

Aa7''

Compound Aa5'' (360 mg, 0.8 mmol), 4-dimethylaminopyridine (200 mg, 1.6 mmol), phosphorus oxychloride (5 mL), tetrahydrofuran (50 mL), morpholine (2 mL); to give a white solid (370 mg, 88%).

$^1$H NMR (300 MHz, CDCl$_3$) δ 8.75 (s, 1H), 8.72 (s, 1H), 8.24 (s, 1H), 7.09 (s, 1H), 4.07 (t, J=4.8 Hz, 4H), 3.86 (t, J=4.8 Hz, 4H), 1.36 (s, 9H).

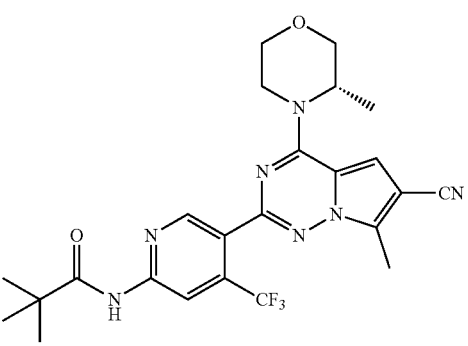

Aa7'''

Compound Aa5' (800 mg, 1.9 mmol), 4-dimethylaminopyridine (466 mg, 3.8 mmol), phosphorus oxychloride (15 mL), tetrahydrofuran (100 mL), (S)-3-methylmorpholine (5 mL); to give a yellow solid (720 mg, 76%).

Step i: Synthesis of Compound Aa8

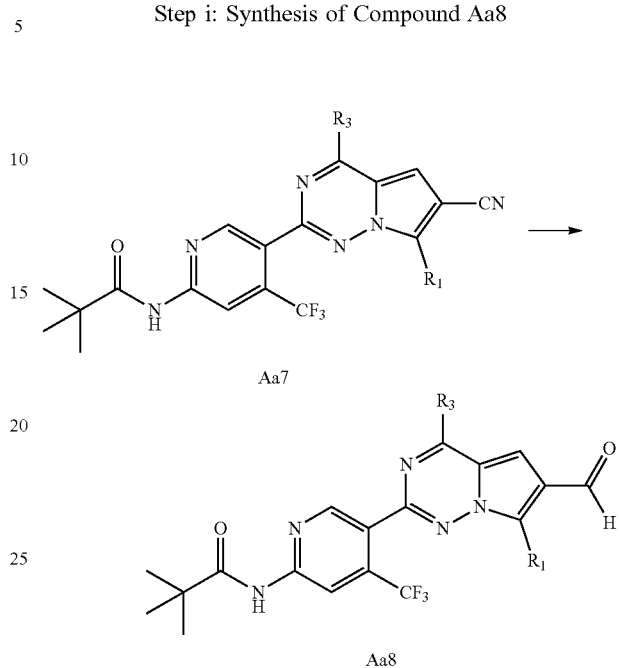

To a suspension of compound Aa7 (1.0 equiv.) and sodium hypophosphite monohydrate (6.7 equiv.) in acetic acid/water/pyridine (v/v/v: 1/1/2) was added Raney nickel, and the mixture was warmed to 60° C. for reaction. The reaction mixture was cooled to room temperature and filtered, extracted with ethyl acetate, washed with 3N hydrochloric acid for three times, concentrated and then purified by column chromatography (dichloromethane/methanol: 50/1) to give a yellow solid.

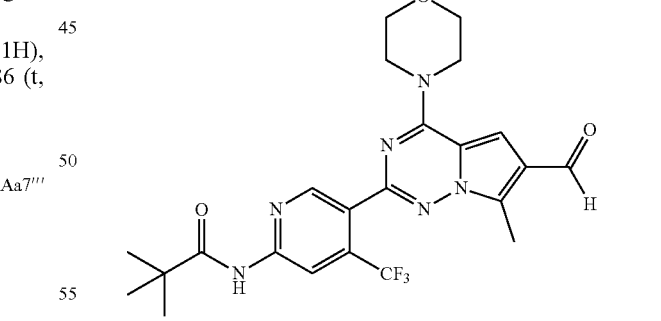

Aa8'

Compound Aa7' (1.0 g, 1.0 mmol), sodium hypophosphite monohydrate (710 mg, 6.7 mmol), acetic acid/water/pyridine (v/v/v: 1/1/2) (50 mL), Raney nickel (750 mg), to give a yellow solid (232 mg, 47%).

$^1$H NMR (300 MHz, CDCl$_3$) δ 10.15 (s, 1H), 8.78 (br s, 1H), 8.72 (s, 1H), 8.25 (s, 1H), 7.17 (s, 1H), 4.10 (t, J=4.8 Hz, 8H), 3.84 (t, J=4.8 Hz, 8H), 2.79 (s, 3H), 1.36 (s, 9H).

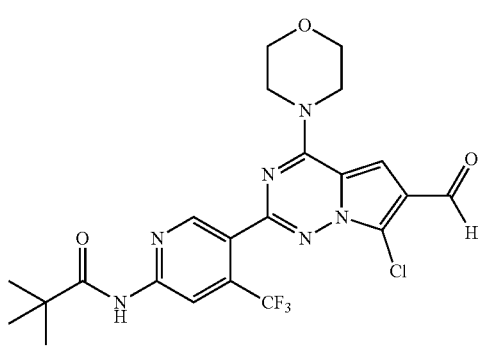

Aa7"

Compound Aa7" (300 mg, 0.6 mmol), sodium hypophosphite monohydrate (426 mg, 4.0 mmol), acetic acid/water/pyridine (v/v/v: 1/1/2) (25 mL), Raney nickel (450 mg), to give a yellow solid (130 mg, 42%).

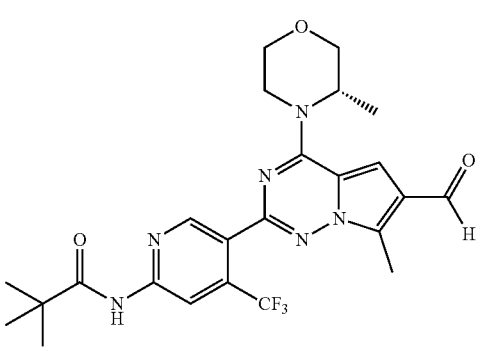

Aa8'''

Compound Aa7''' (600 mg, 1.2 mmol), sodium hypophosphite monohydrate (852 mg, 8.0 mmol), acetic acid/water/pyridine (v/v/v: 1/1/2) (50 mL), Raney nickel (900 mg), to give a yellow solid (420 mg, 83%).

Step j: Synthesis of Compounds P-(1-9), 12, (29-32), (34-35), (38-43), (45-46)

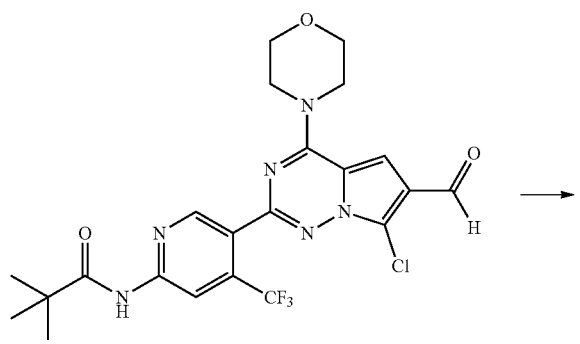

Aa8

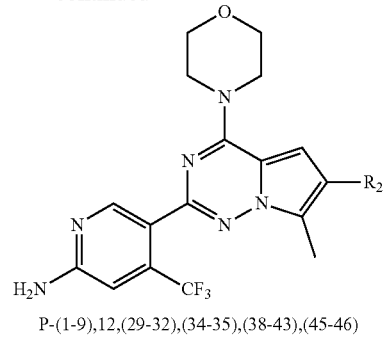

P-(1-9),12,(29-32),(34-35),(38-43),(45-46)

Compound Aa8 (0.2 mmol), sodium cyanoborohydride (0.4 mmol) and the corresponding amine (0.24 mmol) were suspended in methanol (20 mL), acetic acid (0.05 mL) was added, and then the mixture was stirred at room temperature. After the reaction was completed, the mixture was diluted with water (50 mL) and extracted twice with ethyl acetate (100 mL). The organic layers were combined, washed once with saturated brine (100 mL) and dried over anhydrous sodium sulfate, concentrated and then subjected to column chromatography (dichloromethane/methanol: 40/1) to give a product.

The resulting product was dissolved in methanol (15 mL), added 10 equivalents of 1M potassium hydroxide solution, and refluxed. After the reaction was completed, the reaction mixture was concentrated and purified by column chromatography (dichloromethane/methanol: 40/1).

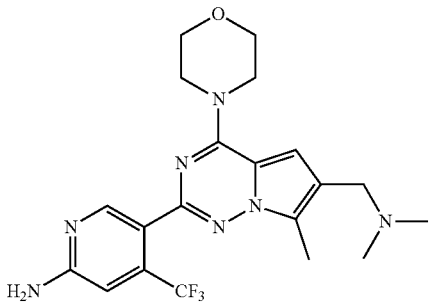

P-1

Yellow solid (38 mg, total yield of two steps: 44%). $^1$H NMR (300 MHz, CDCl$_3$) δ 8.62 (s, 1H), 6.80 (s, 1H), 6.73 (s, 1H), 4.90 (br s, 2H), 4.03 (t, J=4.5 Hz, 4H), 3.81 (t, J=4.5 Hz, 4H), 3.50 (s, 2H), 2.48 (s, 3H), 2.28 (s, 6H).

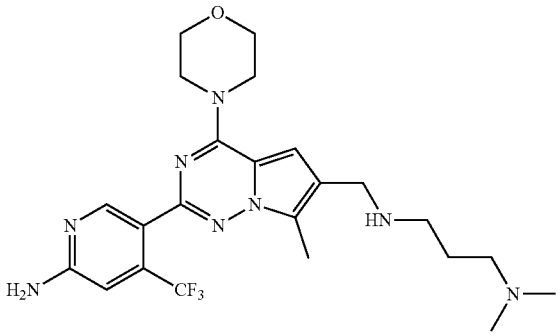

P-2

Yellow solid (44 mg, total yield of two steps: 45%). ¹H NMR (300 MHz, CDCl₃) δ 8.63 (s, 1H), 6.80 (s, 1H), 6.77 (s, 1H), 4.89 (br s, 2H), 4.04 (br s, 4H), 3.87 (s, 2H), 3.82 (br s, 4H), 2.77 (t, J=3.3 Hz, 2H), 2.49 (s, 3H), 2.35 (t, J=6.3 Hz, 2H), 2.23 (s, 6H), 1.80-1.64 (m, 2H).

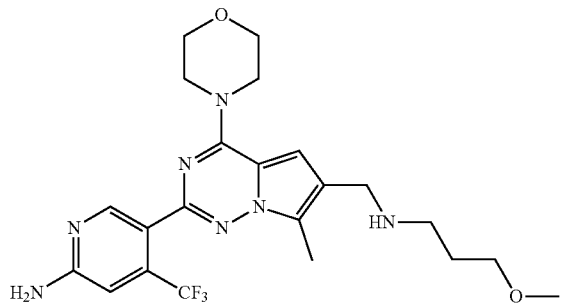

P-3

Yellow solid (49 mg, total yield of two steps: 52%). ¹H NMR (300 MHz, CDCl₃) δ 8.62 (s, 1H), 6.79 (s, 1H), 6.72 (s, 1H), 4.88 (br s, 2H), 4.04 (t, J=3.9 Hz, 4H), 3.91-3.73 (m, 6H), 3.46 (t, J=6.7 Hz, 2H), 3.32 (s, 3H), 2.77 (t, J=6.8 Hz, 2H), 2.49 (s, 3H), 1.89-1.72 (m, 2H). ¹³C NMR (126 MHz, CDCl₃) δ 158.83, 153.94, 151.95, 151.83, 138.11 (q, J=32.4 Hz), 126.24, 122.95 (q, J=274.3 Hz), 122.44, 121.65, 111.79, 105.21 (q, J=5.5 Hz), 103.35, 71.40, 66.81, 58.71, 47.06, 45.94, 45.66, 29.90, 9.24.

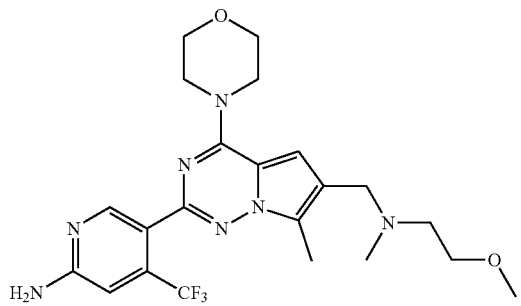

P-4

Yellow solid (38 mg, total yield of two steps: 38%). ¹H NMR (400 MHz, CDCl₃) δ 8.63 (s, 1H), 6.80 (s, 1H), 6.76 (s, 1H), 4.84 (br s, 2H), 4.03 (t, J=4.9 Hz, 4H), 3.82 (t, J=4.8 Hz, 4H), 3.63 (s, 2H), 3.53 (t, J=5.6 Hz, 2H), 3.35 (s, 3H), 2.63 (t, J=5.6 Hz, 2H), 2.48 (s, 3H), 2.33 (s, 3H). ¹³C NMR (101 MHz, CDCl₃) δ 158.77, 153.94, 151.95, 151.77, 138.13 (q, J=32.8 Hz), 127.07, 122.28 (q, J=275.7 Hz), 121.72, 120.25, 111.93, 105.22 (q, J=5.6 Hz), 104.45, 70.60, 66.81, 58.92, 56.06, 54.13, 45.91, 42.68, 9.36.

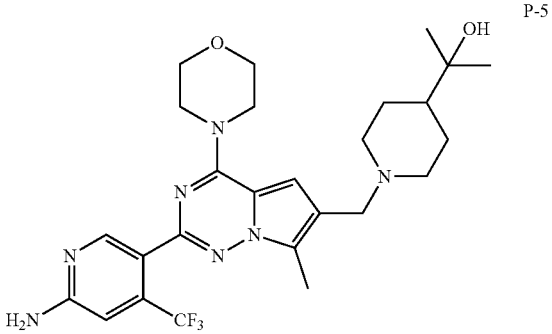 [SMILES: Cc1c(CN2CCC(C(C)(C)O)CC2)cc2c(N3CCOCC3)nc(-c3cnc(N)cc3C(F)(F)F)nn12]

P-5

Yellow solid (68 mg, total yield of two steps: 64%). ¹H NMR (500 MHz, CDCl₃) δ 8.65 (s, 1H), 6.82 (s, 1H), 6.74 (s, 1H), 4.94-4.88 (m, 2H), 4.06 (t, J=4.6 Hz, 4H), 3.84 (t, J=4.8 Hz, 4H), 3.59 (s, 2H), 3.06 (d, J=10.7 Hz, 2H), 2.51 (s, 3H), 1.97 (t, J=11.3 Hz, 2H), 1.81-1.67 (m, 2H), 1.35-1.25 (m, 3H), 1.19 (s, 6H). ¹³C NMR (126 MHz, CDCl₃) δ 158.79, 153.93, 151.95, 151.77, 138.12 (q, J=32.3 Hz), 127.33, 122.95 (q, J=274.5 Hz), 121.68, 120.06, 111.82, 105.23 (q, J=6.2 Hz), 104.54, 72.47, 66.81, 54.58, 54.06, 47.40, 45.93, 27.00, 26.84, 9.48.

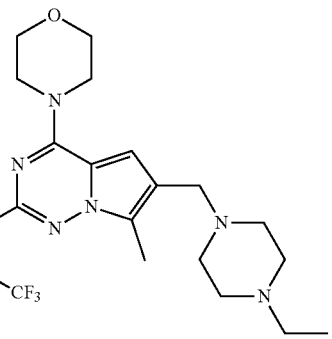

P-6

Yellow solid (58 mg, total yield of two steps: 58%). ¹H NMR (300 MHz, CDCl₃) δ 8.62 (s, 1H), 6.80 (s, 1H), 6.69 (s, 1H), 4.84 (br s, 2H), 4.03 (t, J=4.8 Hz, 4H), 3.82 (t, J=4.8 Hz, 4H), 3.57 (s, 2H), 2.68-2.45 (m, 8H), 2.41 (q, J=7.2 Hz, 2H), 1.07 (t, J=7.2 Hz, 3H). ¹³C NMR (126 MHz, CDCl₃) δ 158.78, 153.94, 151.93, 151.79, 138.15 (q, J=32.5 Hz, CF₃C), 127.42, 122.94 (q, J=274.4 Hz, CF₃), 121.71, 119.89, 111.77, 105.23 (q, J=5.5 Hz, CF₃CCH), 104.57, 66.81, 54.42, 52.97, 52.83, 52.28, 45.94, 12.01, 9.45.

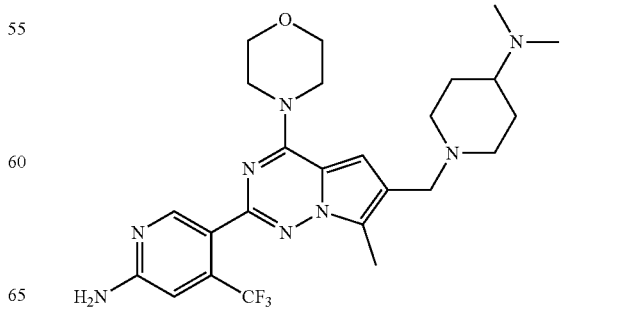

P-7

Yellow solid (55 mg, total yield of two steps: 53%). $^1$H NMR (500 MHz, CDCl$_3$) δ 8.64 (s, 1H), 6.80 (s, 1H), 6.71 (s, 1H), 4.99 (br s, 2H), 4.04 (t, J=4.8 Hz, 4H), 3.83 (t, J=4.8 Hz, 4H), 3.56 (s, 2H), 3.09-2.86 (m, 2H), 2.50 (s, 3H), 2.29 (s, 6H), 2.21-2.07 (m, 1H), 2.05-1.93 (m, 2H), 1.87-1.75 (m, 2H), 1.65-1.44 (m, 2H). $^{13}$C NMR (126 MHz, CDCl$_3$) δ 158.88, 153.92, 151.93, 151.77, 138.07 (q, J=32.5 Hz), 127.26, 122.95 (q, J=274.6 Hz), 121.58, 120.29, 111.78, 105.21 (q, J=5.7 Hz), 104.45, 66.80, 62.32, 54.34, 52.93, 45.92, 41.72, 28.29, 9.45.

P-8

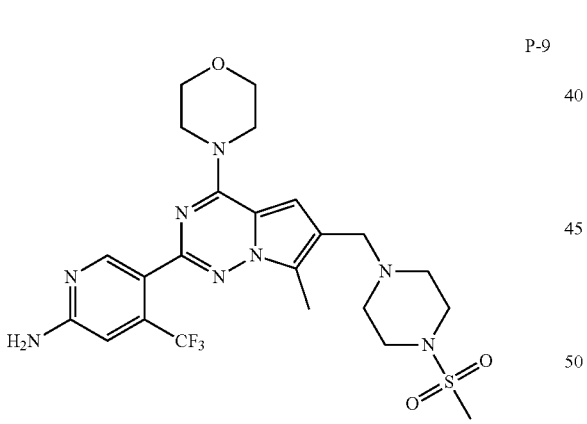

Yellow solid (46 mg, total yield of two steps: 47%). $^1$H NMR (400 MHz, CDCl$_3$) δ 8.62 (s, 1H), 6.81 (s, 2H), 4.87 (br s, 2H), 4.05 (t, J=4.8 Hz, 4H), 3.83 (t, J=4.8 Hz, 4H), 3.70 (s, 2H), 2.85 (s, 4H), 2.78 (s, 4H), 2.49 (s, 3H). $^{13}$C NMR (126 MHz, CDCl$_3$) δ 158.82, 153.96, 152.08, 151.89, 138.16 (q, J=32.3 Hz), 127.58, 122.93 (q, J=274.6 Hz), 121.55, 112.14, 105.29 (q, J=5.4 Hz), 105.03, 66.80, 54.99, 54.49, 45.96, 27.36, 9.47.

P-9

Yellow solid (79 mg, total yield of two steps: 72%). $^1$H NMR (300 MHz, CDCl$_3$) δ 8.62 (s, 1H), 6.81 (s, 1H), 6.64 (s, 1H), 4.84 (br s, 2H), 4.03 (t, J=4.5 Hz, 4H), 3.82 (t, J=4.9 Hz, 4H), 3.60 (s, 2H), 3.24 (t, J=5.0 Hz, 4H), 2.77 (s, 3H), 2.58 (t, J=4.9 Hz, 4H), 2.49 (s, 3H). $^{13}$C NMR (126 MHz, CDCl$_3$) δ 158.83, 153.95, 151.99, 151.95, 138.12 (q, J=32.4 Hz, CF$_3$C), 127.42, 122.95 (q, J=274.4 Hz, CF$_3$), 121.57, 119.23, 111.90, 105.25 (q, J=5.5 Hz, CF$_3$CCH), 104.48, 66.79, 54.26, 52.19, 45.95, 45.84, 34.28, 9.44.

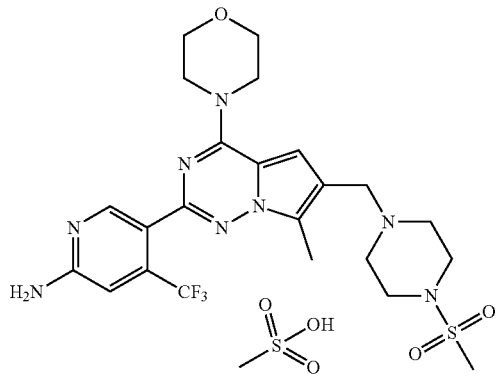

To a solution of compound P-9 (160 mg, 0.3 mmol) in chloroform (10 mL) was added methanesulfonic acid (370 μL, 0.3 mmol). After 2 hours of reaction at room temperature, the reaction mixture was diluted with anhydrous ether (50 mL), filtered and dried to give P-9 methane sulfonate (145 mg, 77%) as a yellow compound.

$^1$H NMR (500 MHz, DMSO-d$_6$) δ 9.89 (br s, 1H), 8.51 (s, 1H), 7.25 (s, 1H), 7.23 (s, 1H), 4.47 (br s, 2H), 4.02 (t, J=5.0 Hz, 4H), 3.76 (t, J=4.9 Hz, 4H), 3.73 (s, 2H), 3.57-3.47 (m, 2H), 3.30-3.09 (m, 4H), 3.01 (s, 3H), 2.52 (br s, 2H), 2.43 (br s, 6H). $^{13}$C NMR (126 MHz, DMSO-d$_6$) δ 157.47, 153.93, 151.45, 145.46, 138.57 (q, J=33.3 Hz), 129.45, 122.77 (q, J=275.06 Hz), 118.65, 112.36, 111.92, 110.13, 107.64, 66.42, 51.32, 50.27, 46.01, 42.96, 40.23, 35.51, 9.65.

P-12

Yellow solid (63 mg, total yield of two steps: 53%). $^1$H NMR (400 MHz, CDCl$_3$) δ 8.63 (s, 1H), 6.83 (s, 1H), 6.70 (s, 1H), 4.99 (br s, 2H), 4.24-3.98 (m, 4H), 3.96-3.78 (m, 4H), 3.60 (s, 2H), 3.46 (br s, 4H), 2.51 (s, 3H), 2.44 (br s, 4H), 1.47 (s, 9H). $^{13}$C NMR (126 MHz, CDCl$_3$) δ 158.91, 154.77, 153.94, 151.85, 151.72, 138.18 (q, J=32.6 Hz), 127.40, 122.93 (q, J=274.1 Hz), 121.50, 119.51, 111.85, 105.39 (q, J=5.6 Hz), 104.52, 79.65, 66.79, 54.45, 52.74, 45.93, 28.43, 9.45.

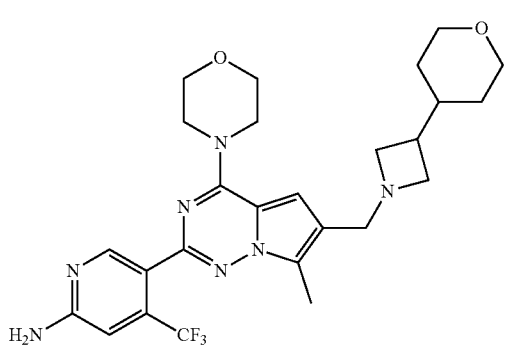

P-29

Yellow solid (45 mg, total yield of two steps: 43%). ¹H NMR (500 MHz, Chloroform-d) δ 8.62 (s, 1H), 6.80 (s, 1H), 6.70 (s, 1H), 4.84 (d, J=7.5 Hz, 2H), 4.06-4.00 (m, 4H), 3.95 (d, J=11.4 Hz, 2H), 3.83-3.80 (m, 4H), 3.65 (s, 2H), 3.47 (t, J=7.5 Hz, 2H), 3.36 (t, J=11.7 Hz, 2H), 2.88 (t, J=7.3 Hz, 2H), 2.32-2.16 (m, 2H), 1.71-1.57 (m, 2H), 1.52 (ddd, J=13.2, 3.8, 1.9 Hz, 2H).

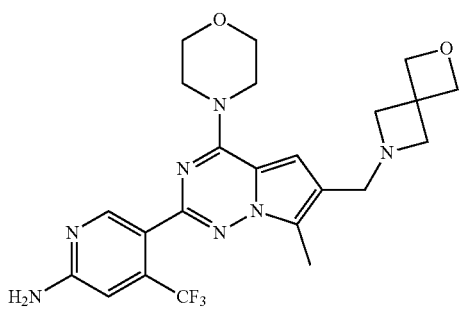

P-30

Yellow solid (40 mg, total yield of two steps: 41%). ¹H NMR (500 MHz, Chloroform-d) δ 8.62 (s, 1H), 6.81 (s, 1H), 6.65 (s, 1H), 4.85 (d, J=5.3 Hz, 2H), 4.75 (s, 4H), 4.05-4.00 (m, 4H), 3.82 (t, J=4.9 Hz, 4H), 3.61 (s, 2H), 3.42 (s, 3H), 2.48 (s, 4H).

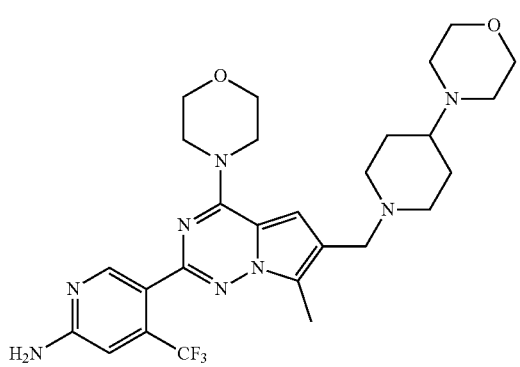

P-31

Yellow solid (36 mg, total yield of two steps: 32%). ¹H NMR (300 MHz, Chloroform-d) δ 8.61 (s, 1H), 6.79 (s, 1H), 6.72 (s, 1H), 4.90 (d, J=5.8 Hz, 2H), 4.02 (t, J=4.7 Hz, 4H), 3.81 (t, J=4.8 Hz, 5H), 3.73-3.68 (m, 4H), 3.57 (s, 2H), 3.00 (d, J=11.1 Hz, 2H), 2.58-2.46 (m, 8H), 2.18 (dq, J=11.2, 5.9, 4.2 Hz, 1H), 2.01 (t, J=11.1 Hz, 2H), 1.82 (d, J=13.4 Hz, 2H), 1.58 (td, J=12.1, 3.6 Hz, 2H).

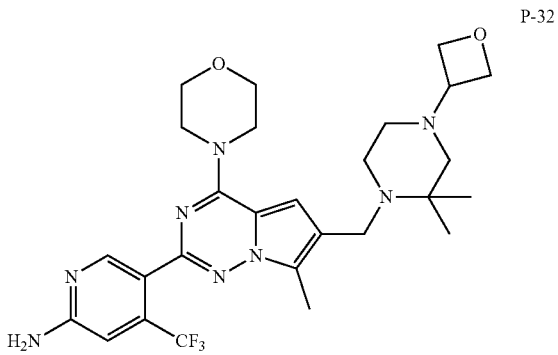 [SMILES: Cc1c(CN2CCN(C3COC3)CC2(C)C)cc2c(N3CCOCC3)nc(-c3cnc(N)cc3C(F)(F)F)nn12]

P-32

The corresponding amine was synthesized by taking reference to WO2010138589 (A1). Yellow solid (20 mg, total yield of two steps: 18%). ¹H NMR (400 MHz, Chloroform-d) δ 8.61 (s, 1H), 7.74-7.50 (m, 1H), 6.81 (s, 1H), 4.84 (s, 2H), 4.67-4.60 (m, 2H), 4.59-4.51 (m, 2H), 4.32-4.13 (m, 2H), 4.10-3.98 (m, 4H), 3.83 (t, J=4.9 Hz, 4H), 2.92-2.74 (m, 1H), 2.50 (s, 3H), 2.21 (d, J=7.7 Hz, 2H), 2.06-1.97 (m, 4H), 1.00-0.84 (m, 6H).

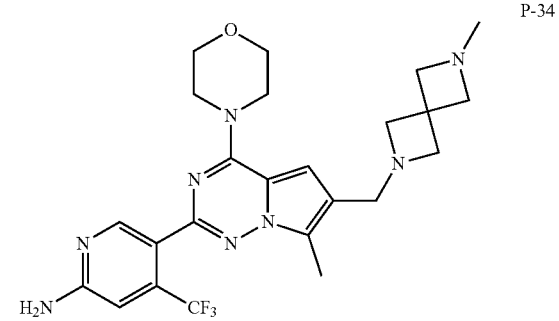 [SMILES: Cc1c(CN2CC3(CN(C)C3)C2)cc2c(N3CCOCC3)nc(-c3cnc(N)cc3C(F)(F)F)nn12]

P-34

Yellow solid (52 mg, total yield of two steps: 52%). ¹H NMR (300 MHz, Chloroform-d) δ 8.62 (s, 1H), 6.80 (s, 1H), 6.67 (d, J=1.3 Hz, 1H), 4.84 (d, J=4.0 Hz, 2H), 4.08-3.98 (m, 4H), 3.81 (t, J=4.8 Hz, 4H), 3.62 (s, 2H), 3.37 (dd, J=4.3, 1.5 Hz, 8H), 2.47 (d, J=1.5 Hz, 3H), 2.32 (d, J=1.5 Hz, 3H).

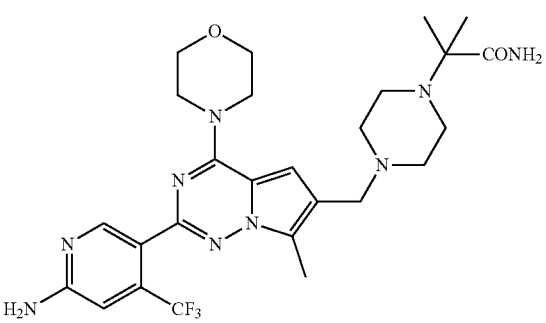

P-35

The corresponding amine was synthesized by taking reference to WO2010138589 (A1). Yellow solid (75 mg, total yield of two steps: 67%). ¹H NMR (400 MHz, Chloroform-d) δ 8.61 (s, 1H), 7.14 (d, J=5.3 Hz, 1H), 6.80 (s, 1H), 6.68 (s, 1H), 5.54 (d, J=5.3 Hz, 1H), 4.93 (s, 2H), 4.03 (dd, J=5.7, 4.0 Hz, 4H), 3.82 (dd, J=5.7, 4.0 Hz, 4H), 3.58 (s, 2H), 2.59-2.52 (m, 6H), 2.49 (s, 3H), 1.20 (s, 8H).

P-38

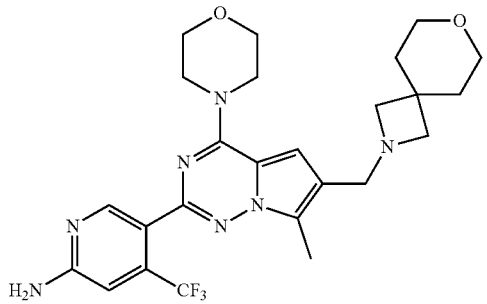

Yellow solid (49 mg, total yield of two steps: 47%). ¹H NMR (400 MHz, Chloroform-d) δ 8.61 (s, 1H), 6.85 (s, 1H), 6.81 (s, 1H), 4.86 (s, 2H), 4.04 (t, J=4.9 Hz, 4H), 3.82 (q, J=4.8, 3.6 Hz, 8H), 3.58 (t, J=5.3 Hz, 4H), 3.28-3.25 (m, 2H), 2.51 (s, 3H), 1.81 (t, J=5.6 Hz, 4H).

P-39

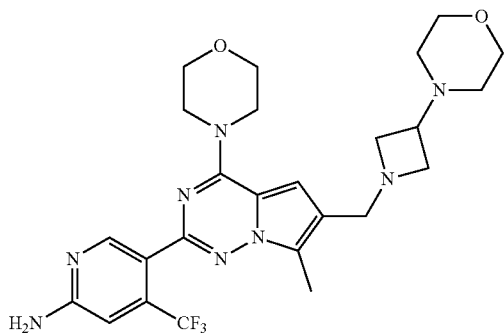

The corresponding amine was synthesized by taking reference to WO2010138589 (A1). Yellow solid (47 mg, total yield of two steps: 44%). ¹H NMR (400 MHz, Chloroform-d) δ 8.61 (s, 1H), 6.80 (s, 1H), 6.77 (s, 1H), 4.88 (s, 2H), 4.03 (dd, J=5.7, 4.1 Hz, 4H), 3.82 (dd, J=5.6, 4.0 Hz, 4H), 3.75 (d, J=1.5 Hz, 2H), 3.47 (s, 2H), 3.42 (d, J=12.1 Hz, 2H), 3.32 (d, J=10.1 Hz, 1H), 3.20 (d, J=10.2 Hz, 1H), 3.01 (s, 1H), 2.78 (dd, J=9.2, 2.4 Hz, 1H), 2.66 (d, J=2.4 Hz, 2H), 2.50 (s, 3H), 2.24-2.14 (m, 1H), 1.75 (d, J=9.7 Hz, 1H), 1.51 (d, J=9.7 Hz, 1H).

P-40

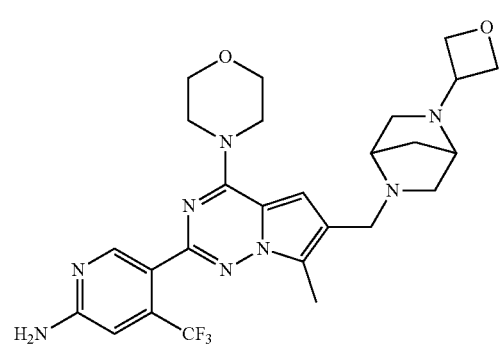

Yellow solid (56 mg, total yield of two steps: 51%). ¹H NMR (400 MHz, Chloroform-d) δ 8.59 (s, 1H), 7.62 (s, 1H), 6.82 (s, 1H), 4.97 (s, 2H), 4.74 (t, J=6.3 Hz, 1H), 4.67 (d, J=6.4 Hz, 1H), 4.55-4.44 (m, 2H), 4.26-4.14 (m, 2H), 4.07 (dd, J=5.7, 4.0 Hz, 4H), 4.03-3.87 (m, 2H), 3.86-3.80 (m, 4H), 3.49 (s, 1H), 3.35 (d, J=11.7 Hz, 1H), 2.82-2.62 (m, 1H), 2.51 (s, 3H), 2.21 (t, J=7.6 Hz, 1H), 2.04-1.97 (m, 2H), 0.90-0.82 (m, 1H).

P-41

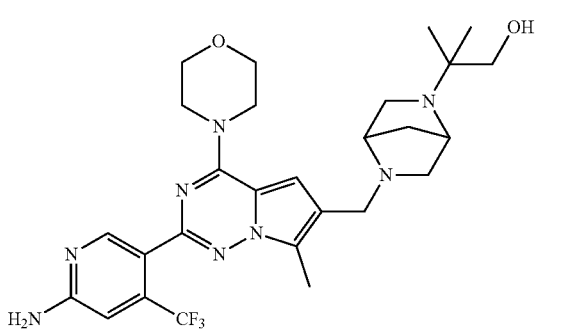

The corresponding amine was synthesized by taking reference to WO2010138589(A1). Yellow solid (53 mg, total yield of two steps: 47%). ¹H NMR (400 MHz, Chloroform-d) δ 8.62 (s, 1H), 6.81 (s, 1H), 6.77 (s, 1H), 4.81 (s, 2H), 4.03 (dd, J=5.7, 4.1 Hz, 4H), 3.83-3.81 (m, 4H), 3.72 (d, J=4.7 Hz, 4H), 3.60 (s, 2H), 3.04 (s, 3H), 2.50 (s, 3H), 2.32 (d, J=5.3 Hz, 4H), 1.70 (s, 6H).

P-42

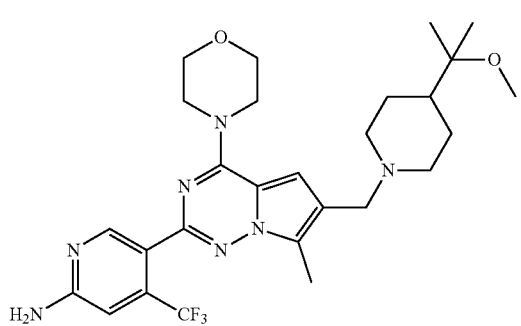

The corresponding amine was synthesized by taking reference to WO2010138589(A1). Yellow solid (52 mg, total yield of two steps: 48%). ¹H NMR (400 MHz, Chloroform-d) δ 8.61 (d, J=3.7 Hz, 1H), 6.81 (s, 1H), 6.71 (s, 1H), 4.88 (s, 2H), 4.03 (dq, J=6.3, 2.8, 2.3 Hz, 4H), 3.85-3.79 (m, 4H), 3.59 (s, 2H), 3.34 (s, 2H), 2.67-2.42 (m, 15H), 1.04 (s, 6H).

P-43

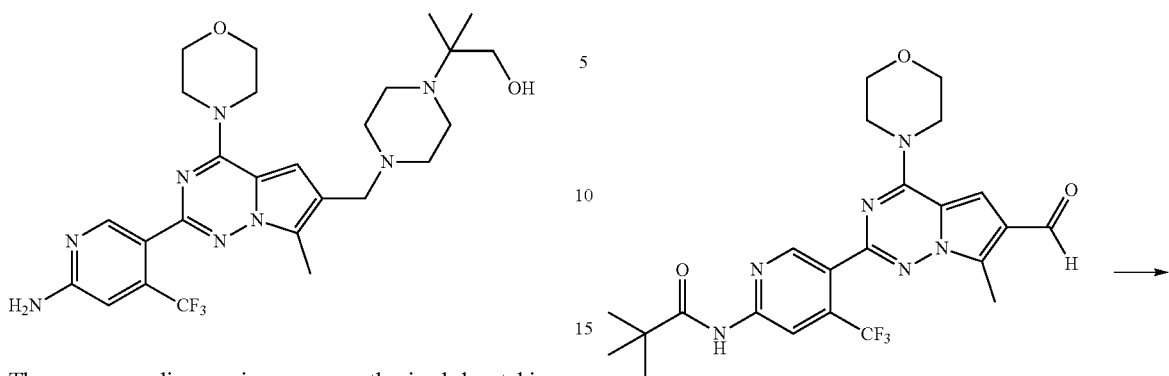

The corresponding amine was synthesized by taking reference to WO2010138589(A1). Yellow solid (52 mg, total yield of two steps: 48%). $^1$H NMR (400 MHz, Chloroform-d) δ 8.62 (s, 1H), 6.80 (s, 1H), 4.86 (s, 2H), 4.04 (dd, J=5.7, 4.1 Hz, 4H), 3.84-3.79 (m, 4H), 3.62 (s, 2H), 3.16 (d, J=1.4 Hz, 2H), 3.09-3.04 (m, 2H), 2.48 (d, J=1.5 Hz, 3H), 2.02 (d, J=13.2 Hz, 2H), 1.67 (d, J=8.8 Hz, 2H), 1.45 (s, 2H), 1.08 (s, 6H).

P-45

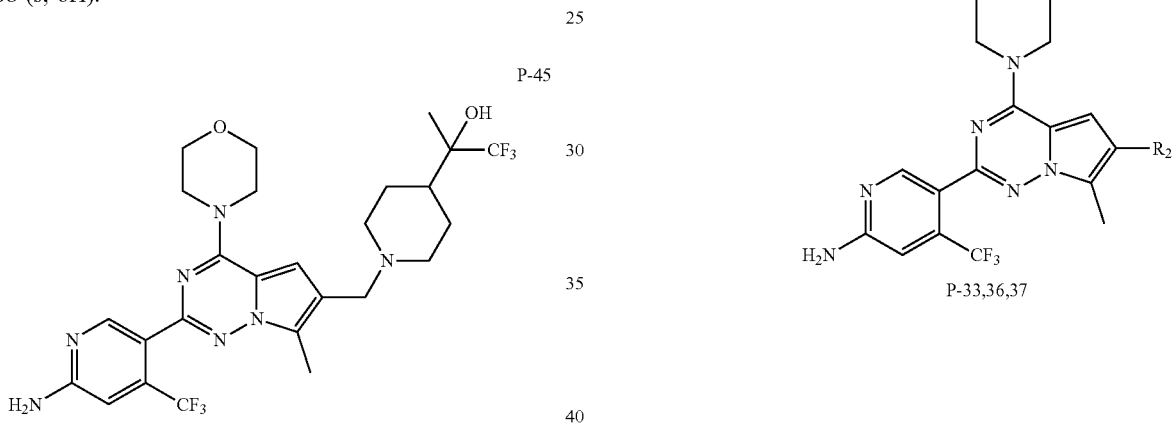

The corresponding amine was synthesized by taking reference to WO2013134226. Yellow solid (50 mg, total yield of two steps: 43%). LC-MS m/z: [M+H]$^+$=588.0.

P-46

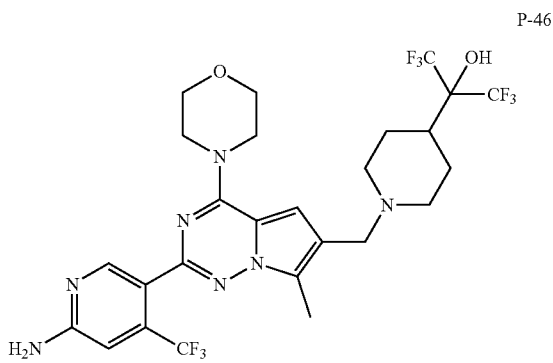 [SMILES: Cc1c(CN2CCC(C(O)(C(F)(F)F)C(F)(F)F)CC2)cc2c(N3CCOCC3)nc(-c3cnc(N)cc3C(F)(F)F)nn12]

The corresponding amine was synthesized by taking reference to WO2013134226. Yellow solid (61 mg, total yield of two steps: 48%). LC-MS m/z: [M+H]$^+$=641.9.

Step j: Synthesis of Compounds P-33, 36, 37

Aa8

P-33,36,37

Compound Aa8 (0.2 mmol), sodium cyanoborohydride (0.4 mmol) and the corresponding Boc-protected amine (0.24 mmol) were suspended in methanol (20 mL), acetic acid (0.05 mL) was added, and then the mixture was stirred at room temperature. After the reaction was completed, the reaction mixture was diluted with water (50 mL) and extracted twice with ethyl acetate (100 mL). The organic layers were combined, washed once with saturated brine (100 mL) and dried over anhydrous sodium sulfate, concentrated and then subjected to column chromatography (dichloromethane/methanol: 40/1) to give a product.

The product was dissolved in dichloromethane (10 mL), and 10-fold equivalent of trifluoroacetic acid was added, then the mixture was stirred at room temperature for 2 days, and then evaporated directly after the reaction was completed.

The resulting product was dissolved in methanol (15 mL), and 10 equivalents of 1M potassium hydroxide solution were added, then the mixture was refluxed. After the reaction was completed, the reaction mixture was concentrated and purified by column chromatography (dichloromethane/methanol: 40/1).

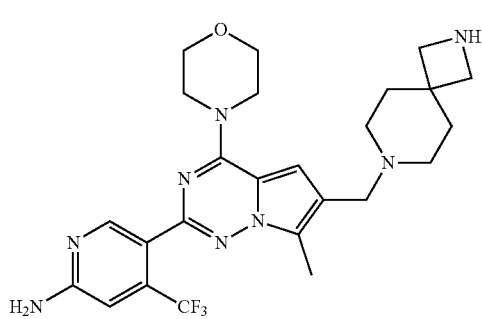

P-33

Yellow solid (52 mg, total yield of two steps: 50%). ¹H NMR (400 MHz, Chloroform-d) δ 8.62 (s, 1H), 6.81 (s, 1H), 6.68 (d, J=3.4 Hz, 1H), 4.83 (s, 2H), 4.03 (t, J=4.8 Hz, 4H), 3.82 (t, J=5.0 Hz, 4H), 3.49 (d, J=3.3 Hz, 2H), 3.36 (s, 2H), 2.47 (d, J=3.4 Hz, 3H), 2.34 (s, 2H), 1.93 (s, 4H), 1.79 (t, J=5.3 Hz, 4H).

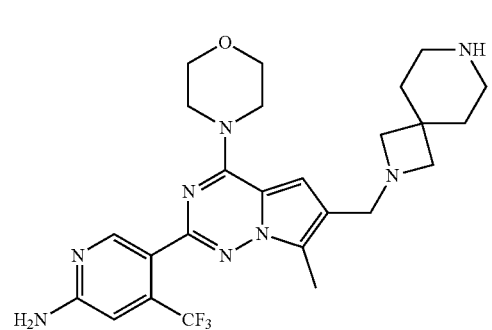

P-36

Yellow solid (50 mg, total yield of two steps: 48%). ¹H NMR (400 MHz, Chloroform-d) δ 8.60 (s, 1H), 6.79 (s, 1H), 6.67 (s, 1H), 4.90 (s, 2H), 4.02 (dd, J=5.7, 4.1 Hz, 4H), 3.84-3.77 (m, 4H), 3.67 (s, 2H), 3.05 (s, 4H), 2.77 (dd, J=6.6, 4.0 Hz, 4H), 2.49 (s, 3H, 1.76-1.69 (m, 4H).

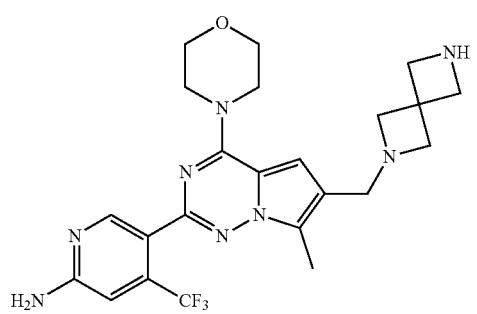

P-37

Yellow solid (45 mg, total yield of two steps: 46%). ¹H NMR (400 MHz, Chloroform-d) δ 8.62 (d, J=2.0 Hz, 1H), 6.81 (s, 1H), 6.65 (d, J=3.8 Hz, 1H), 4.80 (s, 2H), 4.03 (q, J=4.1, 3.2 Hz, 4H), 3.82 (t, J=4.8 Hz, 4H), 3.74 (s, 2H), 3.60 (d, J=2.5 Hz, 2H), 3.35 (s, 3H), 3.30 (d, J=8.3 Hz, 2H), 2.51-2.46 (m, 4H).

Step j: Synthesis of Compound P-44

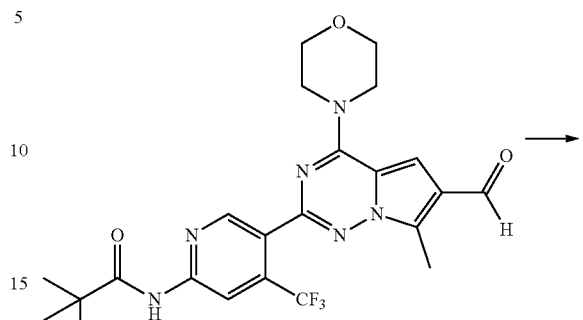

Aa8

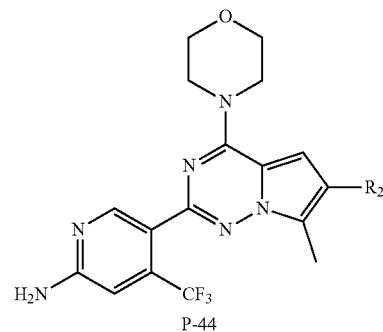

P-44

Compound Aa8 (0.2 mmol), sodium cyanoborohydride (0.4 mmol) and N-acetyl-2-(4-piperidyl)-2-propylamine (0.24 mmol) were suspended in methanol (20 mL), and acetic acid (0.05 mL) was added, then the mixture was stirred at room temperature. After the reaction was completed, the reaction mixture was diluted with water (50 mL) and extracted twice with ethyl acetate (100 mL). The organic layers were combined, washed once with saturated brine (100 mL) and dried over anhydrous sodium sulfate, concentrated and then subjected to column chromatography (dichloromethane/methanol: 40/1) to give a product.

The resulting product was dissolved in concentrated hydrochloric acid (10 mL), and refluxed for 7 days. After the reaction was completed, the reaction mixture was neutralized and purified by column chromatography (dichloromethane/methanol: 10/1).

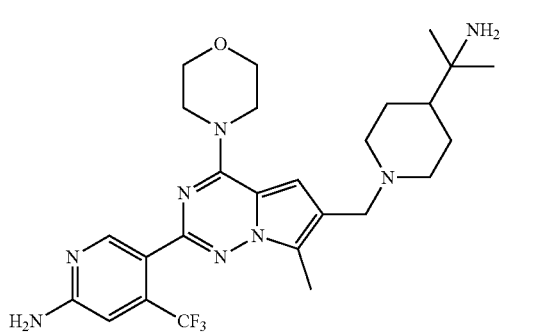

P-44

N-acetyl-2-(4-piperidyl)-2-propylamine was synthesized by taking reference to WO2014043068. Yellow solid (12 mg, total yield of two steps: 11%). LC-MS m/z: [M+H]⁺ =533.0.

Step j: Synthesis of Compound P-10

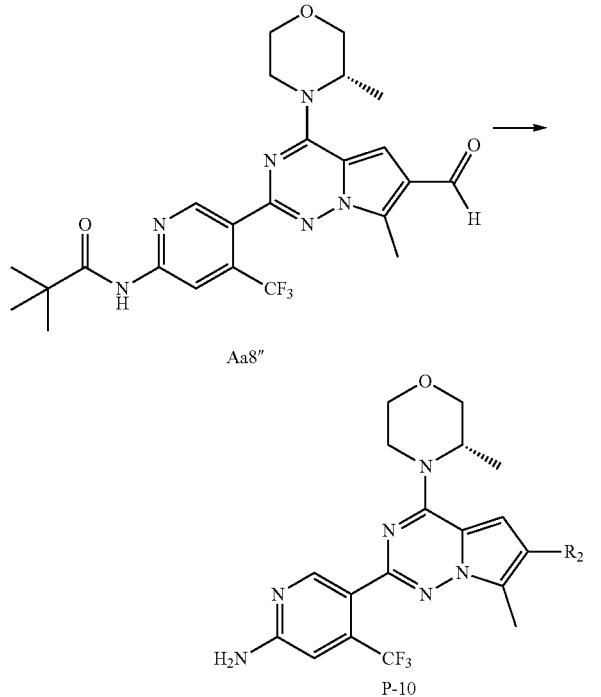

Compound Aa8″ (0.2 mmol), sodium cyanoborohydride (0.4 mmol) and the corresponding amine (0.24 mmol) were suspended in methanol (20 mL), and acetic acid (0.05 mL) was added, then the mixture was stirred at room temperature. After the reaction was completed, the reaction mixture was diluted with water (50 mL) and extracted twice with ethyl acetate (100 mL). The organic layers were combined, washed once with saturated brine (100 mL) and dried over anhydrous sodium sulfate, concentrated and then subjected to column chromatography (dichloromethane/methanol: 40/1) to give a product.

The resulting product was dissolved in methanol (15 mL), and 10 equivalents of 1M potassium hydroxide solution were added, then the mixture was refluxed. After the reaction was completed, the reaction mixture was concentrated and purified by column chromatography (dichloromethane/methanol: 40/1).

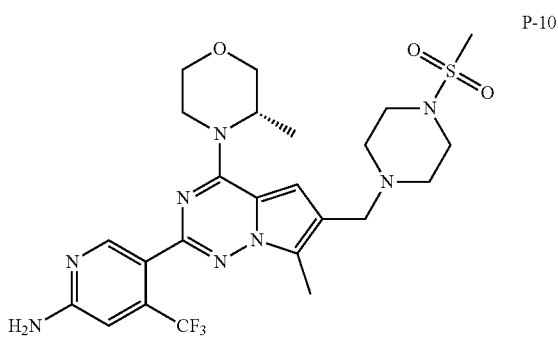 [SMILES: Cc1c(CN2CCN(S(C)(=O)=O)CC2)cc2c(N3CCOC[C@@H]3C)nc(-c3cnc(N)cc3C(F)(F)F)nn12]

P-10

Yellow solid (55 mg, total yield of two steps: 48%). ¹H NMR (300 MHz, Chloroform-d) δ 8.63 (d, J=3.1 Hz, 1H), 6.82 (d, J=3.1 Hz, 1H), 6.65 (s, 1H), 4.93 (br s, 1H), 4.83 (s, 2H), 4.56 (d, J=11.3 Hz, 1H), 4.09-3.97 (m, 1H), 3.89-3.74 (m, 2H), 3.72-3.53 (m, 4H), 3.26 (s, 4H), 2.78 (s, 3H), 2.60 (s, 4H), 2.49 (s, 3H), 1.45 (d, J=6.8 Hz, 3H). ¹³C NMR (126 MHz, Chloroform-d) δ 158.81, 153.66, 152.06, 151.91, 138.12 (q, J=32.3 Hz), 127.41, 122.94 (d, J=274.5 Hz), 121.65, 111.92, 105.26 (d, J=6.7 Hz), 104.58, 71.03, 66.98, 54.26, 52.16, 45.83, 34.28, 15.27, 9.49.

Step j: Synthesis of Compounds P-11, (25-27)

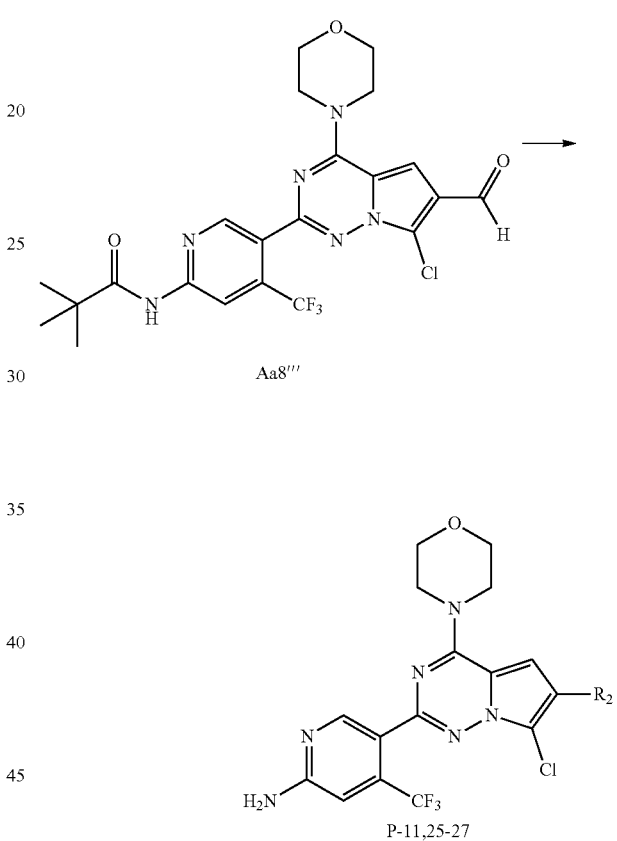

Compound Aa8‴ (0.2 mmol), sodium cyanoborohydride (0.4 mmol) and the corresponding amine (0.24 mmol) were suspended in methanol (20 mL), and acetic acid (0.05 mL) was added, then the mixture was stirred at room temperature. After the reaction was completed, the reaction mixture was diluted with water (50 mL) and extracted twice with ethyl acetate (100 mL). The organic layers were combined, washed once with saturated brine (100 mL) and dried over anhydrous sodium sulfate, concentrated and then subjected to column chromatography (dichloromethane/methanol: 40/1) to give a product.

The resulting product was dissolved in methanol (15 mL), and 10 equivalents of 1M potassium hydroxide solution were added, then the mixture was refluxed. After the reaction was completed, the reaction mixture was concentrated and purified by column chromatography (dichloromethane/methanol: 40/1).

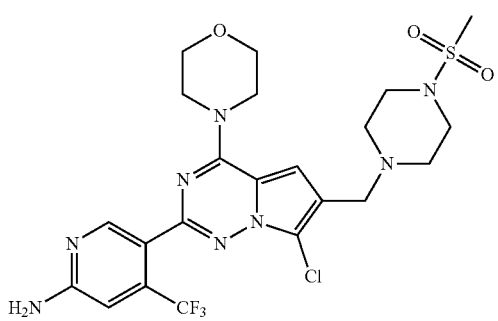

P-11

Yellow solid (34 mg, total yield of two steps: 30%). $^1$H NMR (300 MHz, CDCl$_3$) δ 8.59 (s, 1H), 6.80 (s, 1H), 6.74 (s, 1H), 4.87 (br s, 2H), 4.04 (t, J=4.6 Hz, 4H), 3.83 (t, J=4.7 Hz, 4H), 3.67 (s, 2H), 3.27 (t, J=4.9 Hz, 4H), 2.78 (s, 2H), 2.64 (t, J=5.1 Hz, 4H). $^{13}$C NMR (126 MHz, CDCl$_3$) δ 159.02, 153.50, 153.30, 151.82, 138.25 (q, J=32.8 Hz), 122.85 (q, J=274.3 Hz), 120.96, 118.53, 115.86, 112.74, 105.24 (q, J=6.1 Hz), 104.61, 66.69, 53.04, 52.06, 46.00, 45.79, 34.38.

P-25

White solid (35 mg, yield: 45%). $^1$H NMR (400 MHz, CD$_3$OD) δ8.31 (s, 1H), 7.00 (s, 1H), 6.82 (s, 1H), 3.97 (m, 4H), 3.72 (m, 4H), 3.68 (s, 2H), 3.23 (s, 2H), 3.06 (d, 2H), 2.16 (t, 2H), 1.72 (d, 2H), 1.33 (m, 4H), 1.05 (s, 6H).

P-26

White solid (30 mg, yield: 40%). $^1$H NMR (400 MHz, CD$_3$OD) δ 8.32 (s, 1H), 6.94 (s, 1H), 6.83 (s, 1H), 3.97 (m, 4H), 3.72 (m, 4H), 3.55 (br, s, 1H), 3.22 (d, 2H), 2.92 (d, 2H), 2.23 (s, 6H), 2.03 (d, 2H), 1.78 (d, 2H), 1.47 (d, 2H), 1.18 (d, 2H).

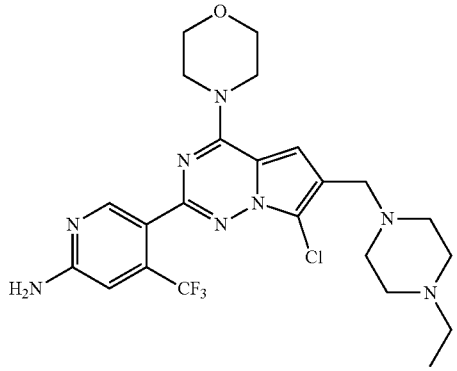

P-27

White solid (38 mg, yield: 42%). $^1$H NMR (400 MHz, CD$_3$OD) δ 8.30 (s, 1H), 6.97 (s, 1H), 6.83 (s, 1H), 4.00 (m, 4H), 3.73 (m, 4H), 3.65 (s, 2H), 3.23 (d, 2H), 2.66 (m, 4H), 1.16 (t, 3H).

Synthesis of Compounds P-13, 14

P-13,14

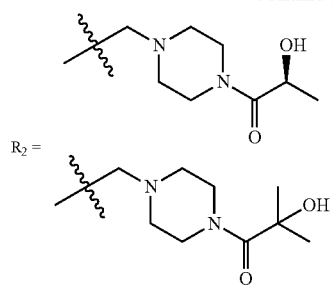

R₂ =

The compound P-12 (500 mg) was dissolved in 40 mL of dichloromethane, added 2.5 mL of trifluoroacetic acid, and then stirred at room temperature for 2 hours. After the reaction was completed, the solvent was removed under reduced pressure to give an oil. The oil was dissolved by adding 10 mL of methanol, and added diethyl ether (80 mL) to precipitate a solid, which was filtered to give 420 mg of the trifluoroacetate salt of the Boc-deprotected product.

The above obtained salt (calculated by containing one molecule of trifluoroacetic acid, 114 mg, 0.2 mmol), the corresponding acid (1.5 equiv.), 1-ethyl-(3-dimethylaminopropyl)carbodiimide hydrochloride (EDC-HCl) (1.5 equiv.), 1-hydroxybenzotriazole (HOBT) (1.5 equiv.) and N, N-diisopropylethylamine (DIPEA) (3 equiv.) were suspended in DMF, then reacted at room temperature. After the reaction was completed, the reaction mixture was diluted with water, and extracted three times with ethyl acetate. The organic layers were combined, dried over anhydrous sodium sulfate, concentrated and then purified by column chromatography (dichloromethane/methanol: 20/1) to give a product.

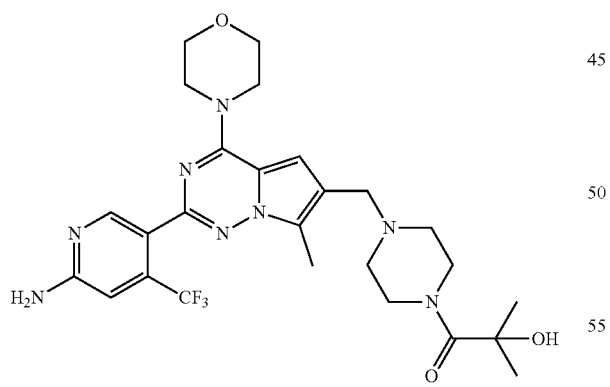

P-13

Yellow solid (67 mg, 60%). ¹H NMR (500 MHz, CDCl₃) δ 8.65 (s, 1H), 6.84 (s, 1H), 6.68 (s, 1H), 4.91 (s, 2H), 4.53 (br s, 1H), 4.06 (t, J=4.8 Hz, 4H), 3.85 (t, J=4.8 Hz, 4H), 3.79-3.65 (m, 4H), 3.60 (s, 2H), 2.51 (s, 7H), 1.50 (s, 6H). ¹³C NMR (126 MHz, CDCl₃) δ 174.93, 158.85, 153.94, 151.94, 151.92, 138.12 (q, J=32.6 Hz), 127.36, 122.90 (q, J=274.06 Hz), 121.55, 119.38, 111.87, 105.27 (q, J=6.3 Hz), 104.42, 71.53, 66.79, 54.40, 52.96, 45.94, 27.83, 9.44.

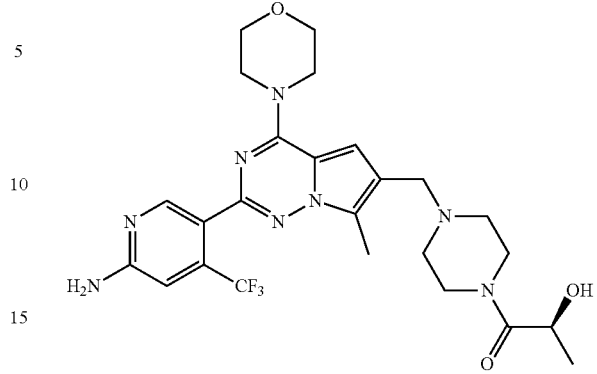

P-14

Yellow solid (55 mg, 50%). ¹H NMR (500 MHz, CDCl₃) δ 8.66 (s, 1H), 6.84 (s, 1H), 6.68 (s, 1H), 4.87 (s, 2H), 4.47 (t, J=6.7 Hz, 1H), 4.07 (t, J=4.8 Hz, 4H), 3.90 (d, J=7.3 Hz, 1H), 3.86 (t, J=4.8 Hz, 4H), 3.82-3.71 (m, 1H), 3.69-3.62 (m, 1H), 3.61 (s, 1H), 3.43 (d, J=5.2 Hz, 2H), 2.58-2.35 (m, 7H), 1.34 (d, J=6.6 Hz, 3H). ¹³C NMR (126 MHz, CDCl₃) δ 173.50, 158.83, 153.95, 151.97, 138.26, 138.13 (d, J=32.8 Hz), 127.37, 122.95 (q, J=274.6 Hz), 121.59, 119.28, 111.89, 105.27, 104.41, 66.79, 64.02, 54.42, 52.70, 52.56, 45.94, 44.87, 42.53, 21.50, 9.44.

Synthesis of Compound P-15

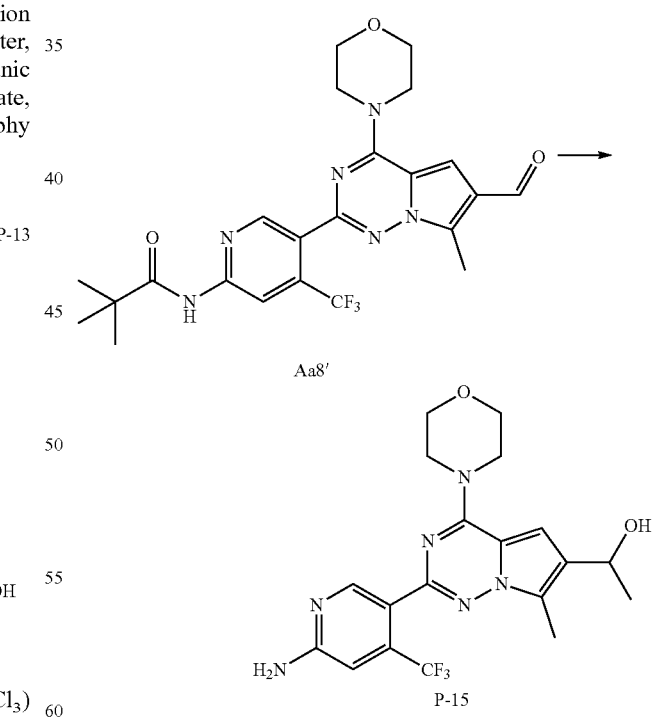

P-15

To a solution of compound Aa8' (600 mg, 1.2 mmol) in anhydrous tetrahydrofuran (40 mL) was added 1M methylmagnesium bromide (4.8 mL, 4.8 mmol) in an ice bath under nitrogen protection, and the mixture was moved to room temperature for reaction. After the reaction was completed, the reaction mixture was diluted with 50 mL of water and extracted twice with ethyl acetate (100 mL). The organic layers were combined, washed once with saturated brine (100 mL) and dried over anhydrous sodium sulfate, concentrated and then subjected to column chromatography (dichloromethane/methanol: 40/1) to give a yellow compound (520 mg, 86%).

The above obtained product (400 mg, 0.8 mmol) was dissolved in 15 mL of methanol, and 10 equivalents of 1M potassium hydroxide solution (8 mL) were added, then the mixture was reacted at reflux. After the reaction was completed, the reaction mixture was concentrated and purified by column chromatography (dichloromethane/methanol=40/1) to give a yellow compound (270 mg, 80%).

$^1$H NMR (300 MHz, CDCl$_3$). δ 8.59 (s, 1H), 6.80 (s, 1H), 6.75 (s, 1H), 5.14 (q, J=4.8 Hz, 1H), 4.82 (s, 2H), 4.04 (t, J=4.8 Hz, 4H), 3.82 (t, J=4.8 Hz, 4H), 2.53 (s, 3H), 1.99 (br s, 1H), 1.58 (d, J=6.4 Hz, 3H). $^{13}$C NMR (126 MHz, CDCl$_3$) δ 158.78, 154.14, 152.05, 151.93, 128.13, 125.24, 111.85, 105.25 (q, J=5.5 Hz), 100.27, 66.80, 63.82, 45.97, 24.52, 9.38.

Synthesis of Compound P-16

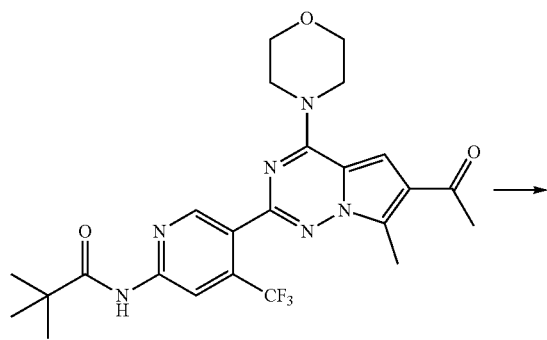

Aa8'

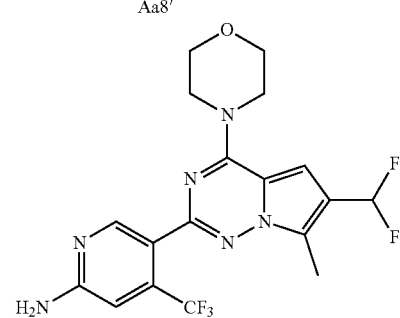

P-16

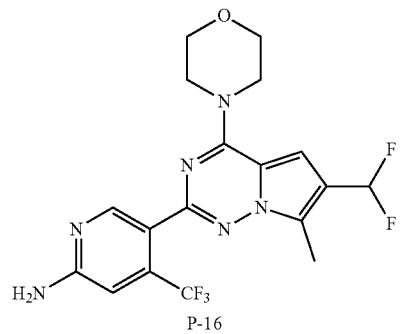

P-16

To a solution of compound Aa8' (100 mg, 0.2 mmol) in anhydrous dichloromethane (20 mL) was added 1 mL of diethylaminosulfur trifluoride (DAST) in an ice bath under nitrogen protection, and the mixture was moved to room temperature for reaction. After the reaction was completed, 10 mL of ice water was slowly added to quench, then the reaction mixture was diluted with water (50 mL) and extracted twice with dichloromethane (50 mL). The organic layers were combined, washed once with saturated brine (100 mL) and dried over anhydrous sodium sulfate, concentrated and then used directly in the next reaction.

The above obtained product was dissolved in 15 mL of methanol, and 10 equivalents of 1M potassium hydroxide solution (2 mL) were added, then the mixture was reflux. After the reaction was completed, the reaction mixture was concentrated and purified by column chromatography (dichloromethane/methanol=40/1) to give a yellow compound (38 mg, total yield of two steps: 44%).

$^1$H NMR (300 MHz, CDCl$_3$). δ 8.63 (s, 1H), 6.86 (t, J=56.4 Hz, 1H), 6.85 (s, 1H), 6.82 (s, 1H), 4.85 (br s, 2H), 4.06 (t, J=4.9 Hz, 4H), 3.84 (t, J=4.8 Hz, 4H), 2.58 (s, 3H). $^{13}$C NMR (101 MHz, CDCl$_3$) δ 158.98, 154.52, 152.94, 151.96, 138.17 (q, J=32.6 Hz), 127.09 (t, J=6.3 Hz), 122.88 (q, J=274.3 Hz), 121.13, 117.39 (t, J=25.8 Hz), 112.40 (t, J=233.7 Hz), 112.24, 105.29 (q, J=6.1 Hz), 101.21 (t, J=5.0 Hz), 66.71, 45.96, 9.46.

Synthesis of Compounds P-17,18

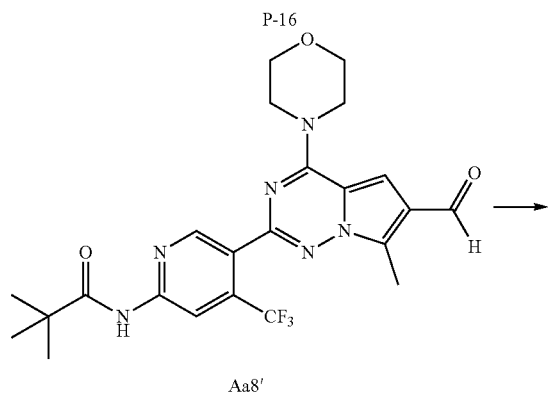

Aa8'

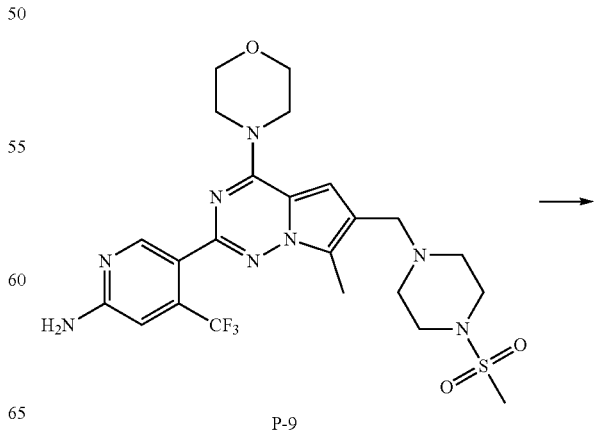

P-9

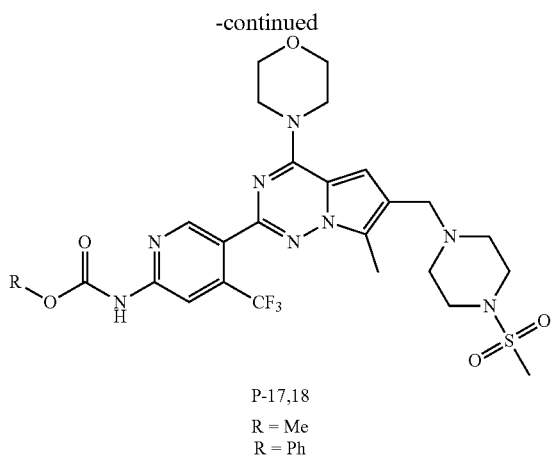

P-17,18
R = Me
R = Ph

To a solution of compound P-9 (110 mg, 0.2 mmol) in anhydrous chloroform (10 mL) was added anhydrous triethylamine (30 μL, 0.25 mmol) at −30° C., and a solution of the corresponding chloroformate (0.6 mmol) in chloroform (5 mL) was added dropwise, then the reaction was maintained at this temperature. After the reaction was completed, 10 mL of ice water was slowly added to quench, and dichloromethane (40 mL) was added to dilute. The organic layer was separated, washed once with saturated brine (50 mL) and dried over anhydrous sodium sulfate, concentrated and purified by column chromatography (dichloromethane/methanol: 50/1 to give a yellow solid.

P-17

Yellow solid (55 mg, 45%). $^1$H NMR (400 MHz, CDCl$_3$) δ 9.18 (br s, 1H), 8.84 (s, 1H), 8.45 (s, 1H), 6.68 (s, 1H), 4.05 (t, J=4.5 Hz, 4H), 3.86 (s, 3H), 3.84-3.78 (m, 4H), 3.62 (s, 2H), 3.25 (s, 4H), 2.78 (s, 3H), 2.59 (s, 4H), 2.50 (s, 3H). $^{13}$C NMR (101 MHz, CDCl$_3$) δ 153.87, 153.54, 152.67, 151.39, 150.80, 138.69 (q, J=32.9 Hz, CF$_3$C), 127.50, 126.60, 122.72 (q, J=275.83 Hz, CF$_3$), 119.55, 111.79, 109.21 (q, J=5.2 Hz, CF$_3$CCH), 104.69, 66.70, 54.19, 52.72, 52.18, 45.89, 45.84, 34.22, 9.40.

Reference was made to the preparation method of the methane sulfonate of compound P-9. Using compound P-17 (200 mg, 0.3 mmol) as a raw material, the methane sulfonate (190 mg, 81%) of compound P-17 was obtained as a yellow compound.

$^1$H NMR (400 MHz, DMSO-d$_6$) δ 10.91 (s, 1H), 9.83 (br s, 1H), 8.79 (s, 1H), 8.31 (s, 1H), 7.23 (s, 1H), 4.46 (s, 2H), 4.01 (t, J=4.8 Hz, 4H), 3.82-3.68 (m, 7H), 3.62-3.41 (m, 4H), 3.28-3.04 (m, 4H), 3.00 (s, 3H), 2.50 (s, 3H), 2.38 (s, 3H). $^{13}$C NMR (126 MHz, DMSO-d$_6$) δ 154.58, 154.11, 153.99, 152.04, 151.38, 136.87 (q, J=31.6 Hz, CF$_3$C), 129.53, 125.47, 123.08 (q, J=274.9 Hz, CF$_3$), 112.40, 112.00, 108.63 (q, J=6.9 Hz, CF$_3$CCH), 107.63, 66.41, 52.76, 51.36, 50.31, 46.02, 42.98, 40.23, 35.54, 9.69.

P-18

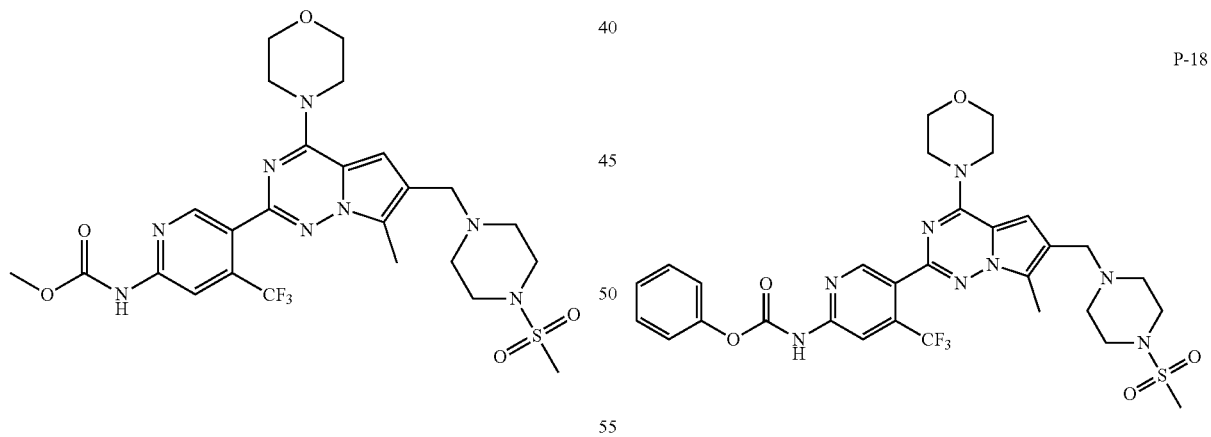

Yellow solid (55 mg, 74%). $^1$H NMR (300 MHz, CDCl$_3$) δ 9.69 (s, 1H), 8.96 (s, 1H), 8.51 (s, 1H), 7.41 (t, J=7.2 Hz, 2H), 7.36-7.19 (m, 3H), 6.67 (s, 1H), 4.13-3.91 (m, 4H), 3.79 (s, 4H), 3.61 (s, 2H), 3.25 (s, 4H), 2.78 (s, 3H), 2.58 (s, 4H), 2.41 (s, 3H).

Synthesis of Compound P-19

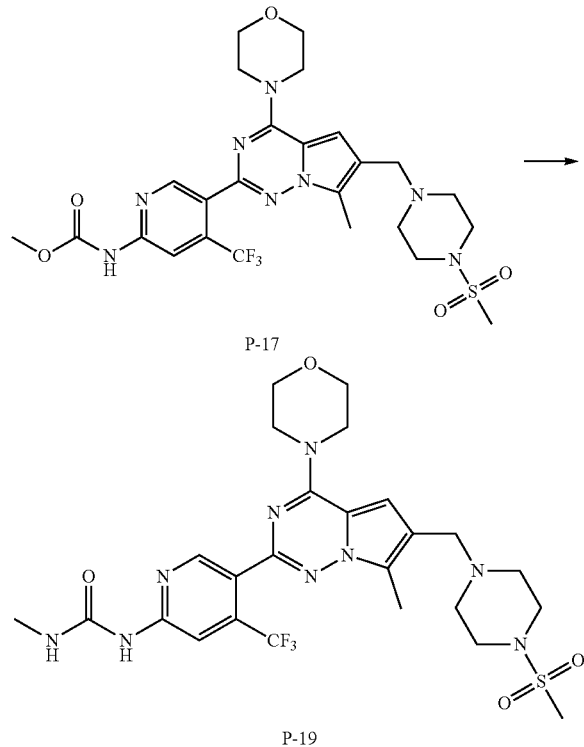

P-17

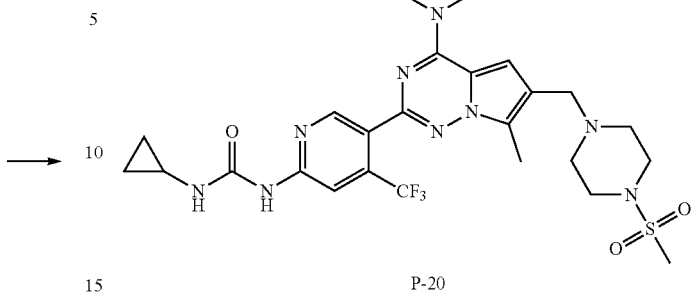

P-20

In a 10 mL microwave reaction tube, compound P-17 (122 mg, 0.2 mmol), anhydrous calcium chloride (10 mg, 0.09 mmol) and methylamine methanolic solution (2 mL) were added, reacted at 100° C. for 30 minutes under microwave, concentrated and purified by thin layer chromatography (dichloromethane/methanol: 20/1) to gave a white solid (30 mg, 33%).

$^1$H NMR (400 MHz, CDCl$_3$). δ 9.37 (s, 1H), 9.06 (br s, 1H), 8.74 (s, 1H), 7.28 (s, 1H), 6.68 (s, 1H), 4.05 (t, J=4.6 Hz, 4H), 3.84 (t, J=4.9 Hz, 4H), 3.61 (s, 2H), 3.25 (br s, 4H), 3.01 (d, J=4.6 Hz, 3H), 2.78 (s, 3H), 2.59 (br s, 4H), 2.50 (s, 3H). $^{13}$C NMR (126 MHz, CDCl$_3$) δ 156.42, 153.99 (q, J=13.5 Hz), 151.34, 149.71, 138.66, 138.39, 127.59, 124.36, 122.56 (q, J=274.93 Hz), 119.56, 111.84, 109.33 (q, J=5.4 Hz), 104.70, 66.78, 54.26, 52.23, 45.95, 45.90, 34.27, 26.54, 9.45.

Synthesis of Compound P-20

To a solution of compound P-18 (75 mg, 0.1 mmol) in DMF (3 mL) was added cyclopropylamine (1 mL), and the mixture was warmed to 60° C. After the reaction was completed, the reaction mixture was diluted with water (30 mL) and extracted twice with ethyl acetate (50 mL). The organic layers were combined, washed once with saturated brine (100 mL) and dried over anhydrous sodium sulfate, concentrated and then subjected to thin layer chromatography (dichloromethane/methanol: 40/1) to give a yellow compound (26 mg, 40%).

$^1$H NMR (400 MHz, CDCl$_3$). δ 9.47 (br s, 1H), 9.09 (br s, 1H), 8.73 (s, 1H), 7.40 (s, 1H), 6.67 (s, 1H), 4.05 (t, J=4.7 Hz, 4H), 3.84 (t, J=4.8 Hz, 4H), 3.61 (s, 2H), 3.25 (t, J=4.7 Hz, 4H), 2.78 (br s, 4H), 2.59 (s, 4H), 2.49 (s, 3H), 0.95-0.78 (m, 2H), 0.71-0.61 (m, 2H). $^{13}$C NMR (126 MHz, CDCl$_3$) δ 156.70, 153.93, 153.85, 151.32, 149.81, 138.53 (q, J=33.2 Hz), 127.59, 124.65, 122.57 (q, J=274.7 Hz), 119.57, 111.83, 109.48 (q, J=6.6 Hz), 104.69, 66.77, 54.26, 52.23, 45.95, 45.90, 34.27, 22.58, 9.45, 6.80.

Synthesis of Compounds P-(21-24)

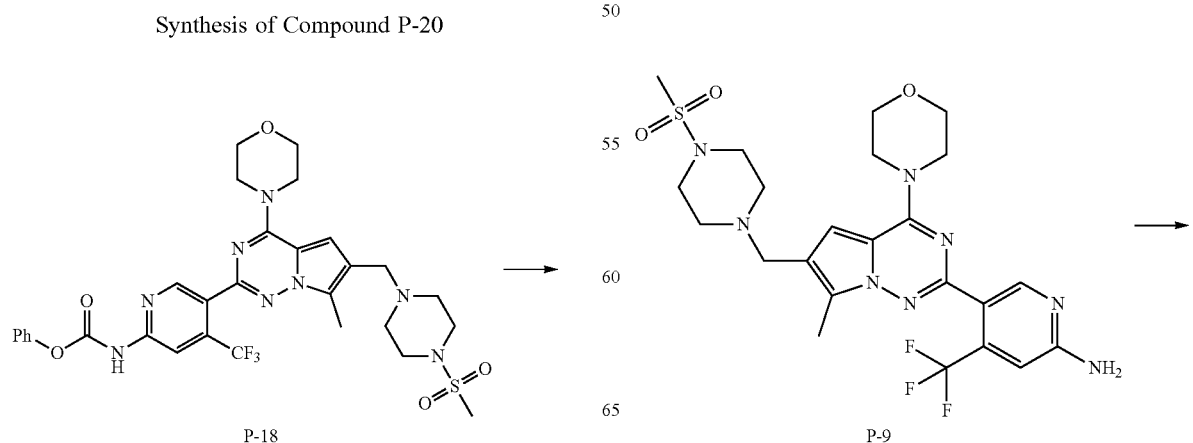

P-18      P-9

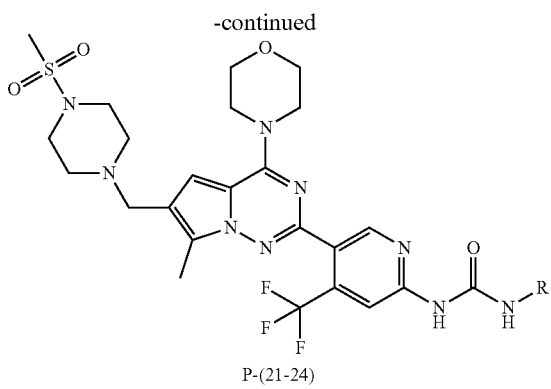

P-(21-24)

To a solution of compound P-9 (1 equiv.) and 1,8-diazacyclo[5.4.0]undec-7-ene (DBU, 6 equiv) in dichloromethane was added the corresponding isocyanate (6 equiv) and reacted at room temperature. After the reaction was completed, the reaction mixture was diluted with water, extracted once with dichloromethane, washed once with saturated brine and dried over anhydrous sodium sulfate, concentrated and then purified by column chromatography (dichloromethane/methanol: 50/1) to give a yellow solid.

P-21

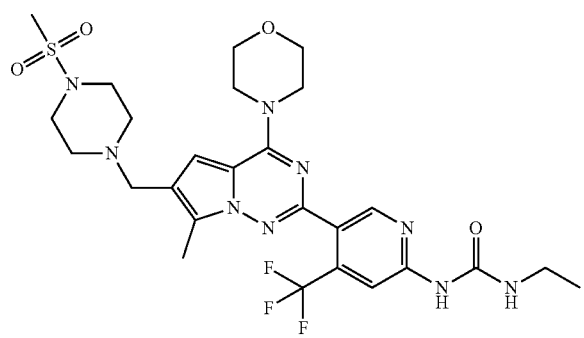

By using compound P-9 (160 mg, 0.3 mmol) as a starting material, a yellow solid (54 mg, 29%) was obtained. $^1$H NMR (300 MHz, DMSO-$d_6$) δ 9.62 (s, 1H), 8.71 (s, 1H), 8.08 (s, 1H), 7.45 (d, J=5.7 Hz, 1H), 6.92 (s, 1H), 3.96 (t, J=4.8 Hz, 4H), 3.73 (t, J=4.8 Hz, 4H), 3.56 (s, 2H), 3.18 (t, J=6.8 Hz, 2H), 3.08 (s, 4H), 2.85 (s, 3H), 2.48 (s, 4H), 2.42 (s, 3H), 1.09 (t, J=7.1 Hz, 3H). $^{13}$C NMR (126 MHz, DMSO-$d_6$) δ 154.81, 154.58, 153.78, 151.31, 150.88, 136.71 (q, J=31.8 Hz), 127.20, 124.08, 123.23 (q, J=274.81 Hz), 120.27, 111.34, 108.29 (q, J=6.2 Hz), 106.21, 66.46, 53.80, 52.14, 45.94, 34.44, 34.06, 15.69, 9.67.

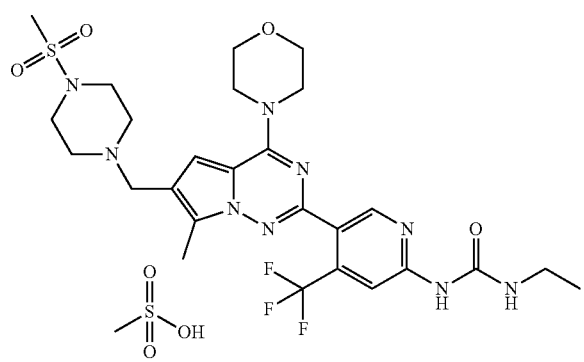

Reference was made to the preparation method of the methane sulfonate of compound P-9. By using compound P-21 (75 mg, 0.31 mmol) as a raw material, the methane sulfonate (70 mg, 81%) of compound P-21 was obtained as a yellow compound.

$^1$H NMR (300 MHz, DMSO-$d_6$) δ 9.80 (br s, 1H), 9.65 (s, 1H), 8.72 (s, 1H), 8.11 (s, 1H), 7.44 (br s, 1H), 7.20 (s, 1H), 4.45 (s, 2H), 4.13 (s, 2H), 4.01 (t, J=4.9 Hz, 4H), 3.75 (s, 6H), 3.49 (s, 2H), 3.27-3.03 (m, 7H), 3.00 (s, 3H), 2.37 (s, 3H), 1.09 (t, J=7.0 Hz, 3H). $^{13}$C NMR (126 MHz, DMSO-$d_6$) δ 155.00, 154.56, 153.98, 152.13, 150.91, 136.74 (q, J=31.4 Hz), 129.46, 123.69, 123.29 (q, J=274.3 Hz), 112.39, 111.93, 108.36 (q, J=6.4 Hz), 107.53, 66.41, 51.36, 40.24, 50.30, 46.00, 42.99, 35.51, 34.45, 15.68, 9.69.

P-22

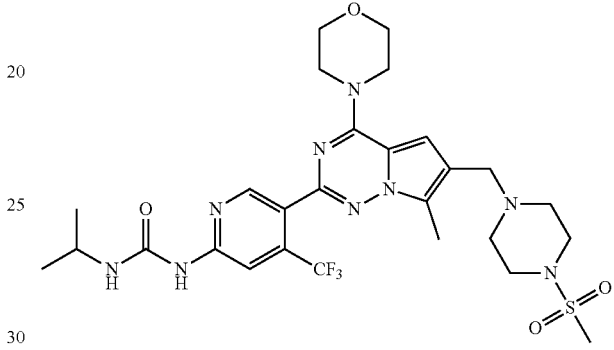

By using compound P-9 (160 mg, 0.3 mmol) as a starting material, a yellow solid (128 mg, 67%) was obtained. $^1$H NMR (300 MHz, CDCl$_3$) δ 9.45 (s, 1H), 8.93 (br s, 1H), 8.74 (s, 1H), 7.30 (s, 1H), 6.67 (s, 1H), 4.10-4.16 (m, 1H), 4.05 (t, J=4.4 Hz, 4H), 3.84 (t, J=4.3 Hz, 4H), 3.61 (s, 2H), 3.25 (t, J=4.5 Hz, 4H), 2.78 (s, 3H), 2.59 (t, J=4.7 Hz, 4H), 2.50 (s, 3H), 1.30 (d, J=6.4 Hz, 6H). $^{13}$C NMR (126 MHz, CDCl$_3$) δ 155.16, 154.33, 153.93, 151.41, 149.67, 138.39 (q, J=32.9 Hz), 127.55, 124.19, 122.61 (q, J=274.4 Hz), 119.53, 111.83, 109.53 (q, J=5.6 Hz), 104.66, 66.78, 54.26, 52.23, 45.95, 45.91, 42.21, 34.25, 23.08, 9.45.

P-23

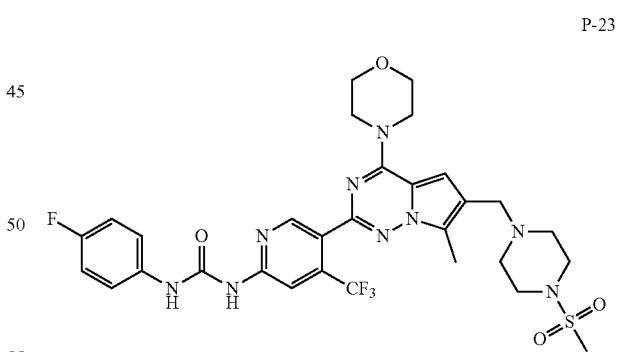

By using compound P-9 (110 mg, 0.2 mmol) as a starting material, a yellow solid (40 mg, 29%) was obtained. $^1$H NMR (300 MHz, CDCl$_3$) δ 11.45 (s, 1H), 9.44 (s, 1H), 8.85 (s, 1H), 7.60 (dd, J=8.9, 4.7 Hz, 2H), 7.35 (s, 1H), 7.07 (t, J=8.2 Hz, 2H), 6.69 (s, 1H), 4.07 (br s, 4H), 3.86 (t, J=5.1 Hz, 4H), 3.63 (s, 2H), 3.26 (s, 4H), 2.79 (s, 3H), 2.60 (s, 4H), 2.52 (s, 3H). $^{13}$C NMR (126 MHz, CDCl$_3$) δ 159.29 (d, J=242.9 Hz), 153.74 (d, J=54.9 Hz), 153.50, 151.09, 149.67, 138.93 (q, J=32.9 Hz), 133.94 (q, J=2.9 Hz), 127.67, 125.13, 122.05 (q, J=7.8 Hz), 119.69, 115.66 (q, J=22.6 Hz), 111.82, 109.78, 104.83, 66.78, 54.27, 52.25, 45.96, 45.91, 34.28, 9.47.

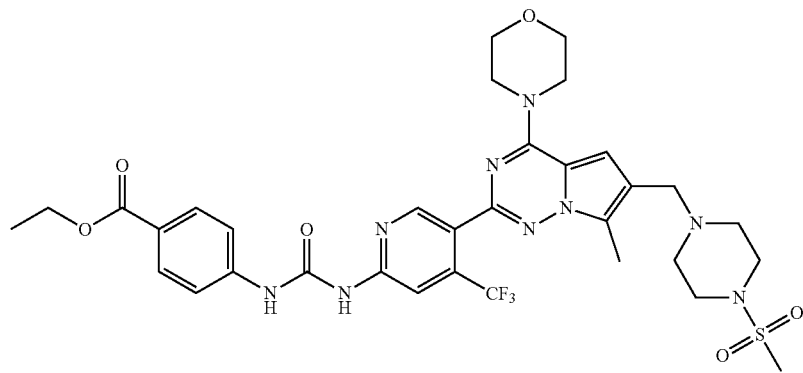
P-24
By using compound P-9 (110 mg, 0.2 mmol) as a starting material, a yellow solid (46 mg, 31%) was obtained. $^1$H NMR (300 MHz, DMSO-d$_6$) δ 10.04 (s, 1H), 9.92 (s, 1H), 8.82 (s, 1H), 8.22 (s, 1H), 7.91 (d, J=8.7 Hz, 2H), 7.65 (d, J=8.8 Hz, 2H), 6.94 (s, 1H), 4.27 (q, J=6.9 Hz, 2H), 3.97 (t, J=4.9 Hz, 4H), 3.82-3.66 (m, 4H), 3.57 (s, 2H), 3.08 (s, 4H), 2.85 (s, 3H), 2.48-2.43 (m, 7H), 1.30 (t, J=7.0 Hz, 3H). $^{13}$C NMR (126 MHz, DMSO-d$_6$) δ 165.79, 153.90, 153.79, 152.07, 151.17, 143.65, 136.95 (q, J=32.2 Hz), 130.89, 127.27, 125.30, 123.23 (q, J=274.93 Hz), 124.16, 120.35, 118.45, 111.35, 108.74, 106.31, 66.47, 60.89, 53.80, 52.14, 45.94, 34.07, 14.71, 9.68.
Synthesis of Compound P-28
-continued
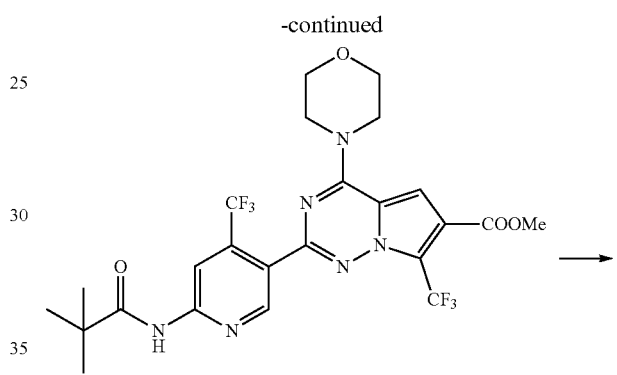
P-28-3
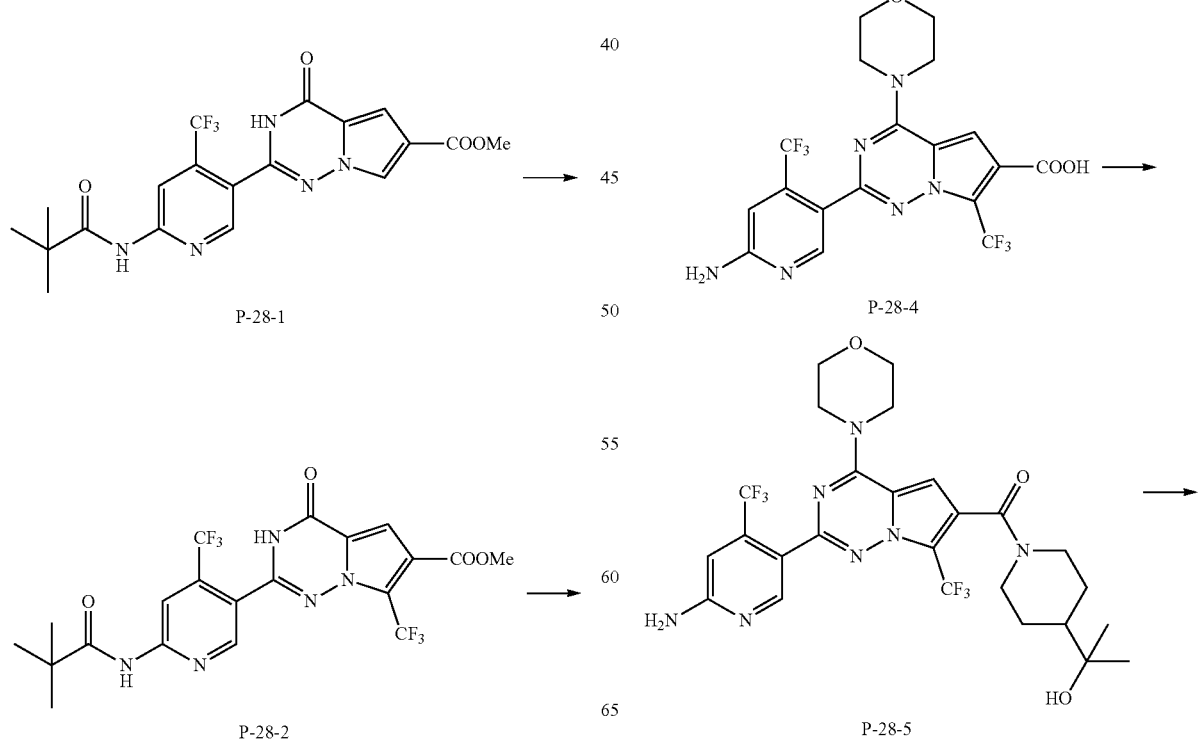
P-28-1
P-28-4
P-28-2
P-28-5

-continued

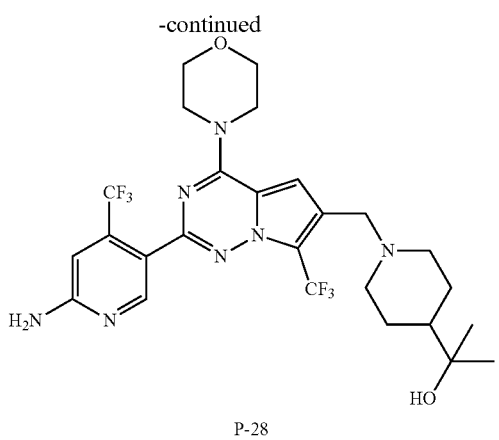

P-28

Step 1: P-28-1 (437.0 mg, 1.0 mmol, for the preparation method thereof, see CN201210177980.3) was dissolved in a mixture of dichloromethane:water (10:1, 20 mL), and then sodium trifluoromethylsulfinate (936.0 mg, 6 mmol) was added, the above system was cooled to 0° C. and 70% aqueous solution of t-butyl hydroperoxide (1.4 mL, 10.0 mmol) was slowly added dropwise. After the dropwise addition was completed, continuing stirring for 30 min; then dimethyl sulfoxide (4.0 mL) was added and warmed to 40° C. to react overnight. The end of the reaction was detected and analyzed by LC-MS. Dichloromethane and water were added and stirred, rested, and the organic phase was separated, dried and concentrated to give a crude product. The crude product was eluated by chromatography with petroleum ether:ethyl acetate (10:1 to 4:1) to give P-28-2 (300 mg). LC-MS: 506.2 (M+1).

Step 2: P-28-2 (300 mg, 0.6 mmol) and phosphorus oxychloride (1.85 g, 11.9 mmol) were added to toluene (20 mL), then N, N-dimethylaniline (215.6 mg, 18.0 mmol) was added and refluxed overnight. After the reaction was completed by TCL analysis, the reaction system was concentrated. Then, ethyl acetate and ice water were added and stirred, and then the ethyl acetate phase was obtained by separation. The ethyl acetate phase was dried and concentrated to give a crude chlorinated compound. The crude chlorinated compound was dissolved in anhydrous tetrahydrofuran (10 mL), morpholine (155.0 mg, 1.8 mmol) was added at 0° C. and the mixture was stirred at room temperature until the raw materials consumed completely, then concentrated to give a crude product, which was used directly in the next step.

Step 3: the crude product obtained from step 2 was dissolved in methanol (20 mL), then added water (1 mL) and sodium hydroxide (237.6 mg) and refluxed until the raw materials were completely disappeared, concentrated, added water, adjusted the pH value to 5-6 to precipitate a solid, dried and used directly in the next step. LC-MS: 477.2 (M+H)$^+$.

Step 4: the crude product from step 3, HBTU (455.0 mg, 1.2 mmol), triethylamine (121 mg, 1.2 mmol) and 2-(4-piperidyl)-2-propanol (Aa9', 93.2 mg, 0.65 mmol) were added to DMF (10 mL) and reacted at room temperature overnight. The end of the reaction was monitored by LC-MS. The reaction system was poured into ice water and extracted with ethyl acetate. The organic phase was dried, concentrated, and passed through a column (DCM: MeOH=100:1~40:1) to give P-28-5 (140 mg) as a light-colored solid.

$^1$H NMR (300 MHz, CD$_3$OD) δ 8.48 (s, 1H), 7.79 (d, 1H), 7.65 (d, 1H), 7.34-7.42 (brs, 2H), 6.81 (s, 1H), 6.70 (s, 1H), 5.26 (s, 1H), 4.76 (d, 1H), 4.02 (s, 4H), 3.80 (s, 4H), 1.82-1.95 (m, 2H), 1.47-1.69 (m, 2H), 1.24 (s, 6H). LC-MS: 602.3 (M+1).

Step 5: Under N$_2$ protection, P-28-5 (100 mg, 0.17 mmol) was dissolved in anhydrous tetrahydrofuran (10 mL) and cooled to −20° C., then BH$_3$/THF (1N, 1.7 mL, 1.7 mmol) was slowly added dropwise. After the dropwise addition was completed, the reaction system was warmed to 60° C. and reacted for 1 h, and then the reaction system was cooled to −20° C. and concentrated hydrochloric acid (0.8 mL) was added dropwise slowly, and then warmed to 60° C. for reaction after addition. It was detected by LC-MS that all intermediates were converted to the target compounds. The mixture was cooled, and then added ethyl acetate and water for liquid-separating to obtain the aqueous phase. The aqueous phase was adjusted to a pH of about 10 with sodium hydroxide, extracted with DCM, dried and concentrated, and then quickly eluated by a column (DCM:MeOH=100:1 to 40:1) to give P-28 (20 mg).

$^1$H NMR (300 MHz, CD$_3$OD) δ: 8.36 (s, 1H), 7.09 (s, 1H), 6.84 (s, 1H), 5.42 (s, 1H), 4.05 (t, 4H), 3.99 (s, 2H), 3.77 (t, 4H), 3.50 (brs, 1H), 2.39 (t, 2H), 1.80 (t, 2H), 1.36~1.52 (m, 4H), 1.08 (s, 6H), LC-MS: 588.2 (M+1).

The Effect of Compounds on the Kinase Activity of PI3K

Concentration setting for preliminary screening: the compounds to be tested were dissolved in DMSO (dimethyl sulfoxide) to 100 μM or 10 μM as storage solutions; for each one, 2 μL was taken to be added to 48 μL of 1× Reaction Buffer to obtain a 4 μM or 400 nM compound solution containing 4% DMSO. After well mixing, the mixture was diluted with 4% DMSO in 1× Reaction Buffer to obtain a 4 μM or 400 nM compound solution. 5 μL of each diluted solution was taken to be added to a 384-well plate, so that the final concentration of the compound in the final 20 μL of the kinase reaction system was 1 μM and 100 nM or 100 nM and 20 nM, respectively, and containing 1% DMSO.

Concentration setting for IC$_{50}$ determination: For different enzymes, 10 μM and 100 μM were selected as the initial concentrations. The compounds to be tested were dissolved in DMSO to 1 mM or 10 mM as working solutions, 1 μL of each working solution was taken to be added to 24 μl of 1× Kinase Buffer A to obtain a 40 μM or 400 μM compound solution containing 4% DMSO. The compound solution was diluted by 4× gradient in sequence, 10 dilution concentrations. 2.5 μL of each diluted solution was taken to be added to a 384-well plate, so that the final concentration of the compound in the final 10 μL of the kinase reaction system was 10 μM, 2.5 μM and 0.625 μM, successively, and containing 1% DMSO.

Experimental Steps: At room temperature, the PI3K kinase was reacted for 30 minutes and then terminated, detection solutions were added to each well, well mixed, and incubated for 2 hours at room temperature, then detected by multifunctional microplate reader (2104 EnVision® Multilabel Reader (Cat: 2104-0010, PerkinElmer)) and the test results were recorded.

Experimental Results

Calculation of the Emission Ratio of Each Well
Emission Ratio (ER)=665 nM Emission signal/620 nm Emission signal
The average Emission Ratio of 100% inhibition control was recorded as: ER$_{100\%}$ The average Emission Ratio of 0% inhibition control was recorded as: $ER_{0\%}$ Calculation of the Inhibition Rate The inhibitory rate was calculated by the following formula:

Inhibitory rate=$(ER_{sample}-ER_{0\%})/(ER_{100\%}-ER_{0\%})\times 100\%$

As shown in Table 1 and Table 2, the compounds in the tables all show good inhibitory effects on PI3K kinase, especially compounds P-5/6/7 show a selective inhibitory effect on PI3Kδ.

TABLE 1

Inhibitory effect of some compounds on various isoforms of PI3K kinase at specified concentrations

| Compound | IH (%) @ 20 nM | | IH (%) @ 100 nM | |
|---|---|---|---|---|
| | α | δ | β | γ |
| P-2 | 18.72 | 46.02 | 4.74 | 0.62 |
| P-3 | 6.72 | 39.81 | −0.12 | 2.94 |
| P-5 | −0.60 | 53.19 | 14.87 | −2.33 |
| P-6 | 69.72 | 41.43 | 11.78 | −4.80 |
| P-7 | 3.60 | 53.59 | 3.43 | −7.96 |
| P-9 | 68.90 | 51.20 | 12.81 | 31.41 |
| P-10 | 80.49 | 39.74 | 7.84 | 32.10 |
| P-11 | 72.76 | 50.28 | 15.82 | 19.40 |
| P-13 | 30.49 | 41.24 | 2.34 | 2.16 |
| P-14 | 24.80 | 63.28 | 3.44 | 6.83 |
| P-17 | 60.73 | 64.14 | 15.98 | 47.01 |
| P-20 | 101.92 | 83.13 | 57.35 | 68.29 |
| P-21 | 89.32 | 107.21 | 46.28 | 74.08 |
| P-22 | 50.00 | 46.54 | 15.08 | 30.34 |
| P-23 | 77.87 | 77.08 | 32.63 | 66.96 |
| GDC0941 | 41.74 | 56.31 | 21.13 | 2.00 |

TABLE 2

Inhibitory effects of some compounds on various isoforms of PI3K kinase

| Compound | IC$_{50}$ (nM) | | | |
|---|---|---|---|---|
| | α | δ | β | γ |
| P-2 | 321.2 | 36.60 | 2135 | 37640 |
| P-5 | 424.3 | 19.60 | 1365 | 4832 |
| P-6 | 624.0 | 35.29 | 4574 | 9875 |
| P-7 | 438.8 | 27.58 | 3459 | 15300 |
| P-9 | 26.41 | 23.69 | 1186 | 282.8 |
| P-10 | 104.1 | 79.66 | 1769 | 201.6 |
| P-11 | 21.29 | 28.08 | 1443 | 247.5 |
| P-14 | 77.46 | 85.57 | 2649 | 1946 |
| P-17 | 76.24 | 75.20 | 912.5 | 290.2 |
| P-20 | 10.79 | 3.733 | 124.3 | 36.55 |
| P-21 | 21.84 | 6.224 | 139.2 | 37.45 |
| P-22 | 122.2 | 29.49 | 1536 | 311.2 |

TABLE 2-continued

Inhibitory effects of some compounds on various isoforms of PI3K kinase

| Compound | IC$_{50}$ (nM) | | | |
|---|---|---|---|---|
| | α | δ | β | γ |
| P-23 | 18.68 | 10.09 | 108.7 | 47.10 |
| GDC0941 | 35.42 | 9.036 | 324.5 | 746.1 |

It can be seen from the tables that compounds P-5, P-6, P-7, etc., have good selectivities for PI3Kδ. GDC0941 is a positive compound with a chemical name of 2-(1H-indazol-4-yl)-6-[[4-(methylsulfonyl)-1-piperazinyl]methyl]-4-(4-morpholinyl)thieno[3,2-D]pyrimidine (4-[2-(1H-indazol-4-yl)-6-[(4-methylsulfonylpiperazin-1-yl)methyl]thieno[3,2-d]pyrimidin-4-yl]morpholine).

Preliminary Pharmacokinetic Test 1. 14 healthy SD rats, male, weigh 200-220 g, were taken to be randomly divided into 4 groups, 3-4 in each group, and were administered the tested compound P-17 and compound CYH33 (compared with compound P-17, missing a methyl group on 7-position) via intragastric administration (10 mg/kg) and intravenous injection (5 mg/kg) respectively, the specific arrangements are shown in the following table 3:

| Group | Number of animals | Compound | Dose route | Dosage (mg/kg) | Dose volume (mL/kg) |
|---|---|---|---|---|---|
| 1 | 4 | CYH33 | Intragastric administration | 10 | 10 |
| 2 | 4 | CYH33 | intravenous | 5 | 5 |
| 3 | 4 | P-17 | Intragastric administration | 10 | 10 |
| 4 | 3 | P-17 | intravenous | 5 | 5 |

The rats were fasted for 12 h before experiment, water was taken freely. The rats were fed 2 h after dosing.

2. Blood Sampling Time Points and Sample Processing

Dosing via intragastric administration: 0.25 h, 0.5 h, 1.0 h, 2.0 h, 3.0 h, 4.0 h, 6.0 h, 8.0 h, and 24 h after dosing.

Dosing via intravenous: 5 min, 0.25 h, 0.5 h, 1.0 h, 2.0 h, 4.0 h, 6.0 h, 8.0 h, and 24 h after dosing.

At the above setting time points, 0.3 ml of venous blood was taken from the retroorbital venous plexus of the rat, and placed in a heparinized test tube, centrifuged at 11,000 rpm for 5 min, then the plasma was separated, and frozen in a refrigerator at −20° C.

3. Sample Testing and Data Analysis

LC/MS/MS method was used to determine the concentration of the compounds in the plasma of rats.

The non-compartment model of Phoenix 1.3 software (Pharsight Corporation, USA) was used to calculate the pharmacokinetic parameters after dosing.

TABLE 4

Pharmacokinetic data after intravenous injection of 5 mg/kg of different compounds in rats

| Treatment | ID | AUC 0 – t (h*ng/ml) | AUC 0 – ∞ (h*ng/ml) | MRT (h) | T1/2 (h) | Cl (l/h/kg) | Vss (l/kg) |
|---|---|---|---|---|---|---|---|
| CYH33 | 5 | 2847 | 2850 | 1.1 | 0.83 | 1.75 | 1.93 |
| | 6 | 3645 | 3655 | 1.26 | 0.95 | 1.37 | 1.72 |
| | 7 | 4142 | 4172 | 1.57 | 1.16 | 1.2 | 1.88 |
| | Mean | 3545 | 3559 | 1.308 | 0.982 | 1.44 | 1.843 |
| | SD | 653 | 666 | 0.239 | 0.168 | 0.285 | 0.11 |
| | CV % | 18.4 | 18.7 | 18.3 | 17.1 | 19.8 | 5.9 |

TABLE 4-continued

Pharmacokinetic data after intravenous injection of 5 mg/kg of different compounds in rats

| Treatment | ID | AUC 0 - t (h*ng/ml) | AUC 0 - ∞ (h*ng/ml) | MRT (h) | T1/2 (h) | Cl (l/h/kg) | Vss (l/kg) |
|---|---|---|---|---|---|---|---|
| P-17 | 5 | 3698 | 4188 | 3.53 | 2.61 | 1.19 | 4.21 |
|  | 6 | 2564 | 2672 | 2.13 | 1.88 | 1.87 | 3.98 |
|  | 7 | 2711 | 2845 | 2.46 | 1.82 | 1.76 | 4.33 |
|  | Mean | 2991 | 3235 | 2.706 | 2.104 | 1.607 | 4.175 |
|  | SD | 617 | 830 | 0.729 | 0.44 | 0.363 | 0.176 |
|  | CV % | 20.6 | 25.6 | 26.9 | 20.9 | 22.6 | 4.2 |

TABLE 5

Pharmacokinetic data after intravenous injection of 10 mg/kg of different compounds in rats

| Treatment | ID | Tmax (h) | Cmax (ng/ml) | AUC0-t (h*ng/ml) | AUC0-∞ (h*ng/ml) | MRT (h) | T½ (h) | F (%) |
|---|---|---|---|---|---|---|---|---|
| CYH33 | 1 | 1 | 770 | 1968 | 2027 | 2.41 | 1.62 | 36.9 |
|  | 2 | 1 | 1743 | 5959 | 6360 | 3.31 | 1.83 |  |
|  | 3 | 0.5 | 441 | 1199 | 1250 | 2.64 | 1.7 |  |
|  | 4 | 1 | 372 | 1351 | 1360 | 2.66 | 0.82 |  |
|  | Mean | 0.875 | 831.5 | 2619 | 2749 | 2.76 | 1.49 |  |
|  | SD | 0.25 | 632 | 2251 | 2432 | 0.39 | 0.46 |  |
|  | CV % | 28.6 | 76 | 86 | 88.4 | 14 | 30.4 |  |
| P-17 | 1 | 4 | 678 | 7245 | 7286 | 5.82 | 3.08 | 95.8 |
|  | 2 | 2 | 875 | 8176 | 8198 | 5.55 | 2.68 |  |
|  | 3 | 1 | 679 | 3389 | 4014 | 4.65 | 2.6 |  |
|  | 4 | 2 | 833 | 4122 | 4993 | 4.94 | 2.71 |  |
|  | Mean | 2.25 | 766.3 | 5733 | 6123 | 5.24 | 2.767 |  |
|  | SD | 1.258 | 102.8 | 2334 | 1948 | 0.539 | 0.215 |  |
|  | CV % | 55.9 | 13.4 | 40.7 | 31.8 | 10.3 | 7.8 |  |

(ID is the animal number, Tmax is the peak time, Cmax is the peak blood drug concentration, AUC is the area under the curve during medication, MRT is the average residence time, Cl is the drug clearance rate, Vss is the steady-state distribution volume, F is the absolute bioavailability)

As can be seen from the above table, although P-17 differs from CYH33 by one methyl, the steady-state distribution volume Vss, average residence time MRT, half-life T½, and absolute bioavailability F of P-17 have all been improved, especially the absolute bioavailability has been greatly increased (the tested compounds are monomesylates of CYH33 and P17, the structures of the compounds are as follows).

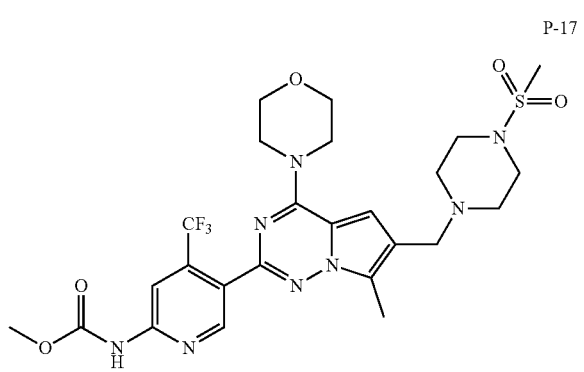

P-17

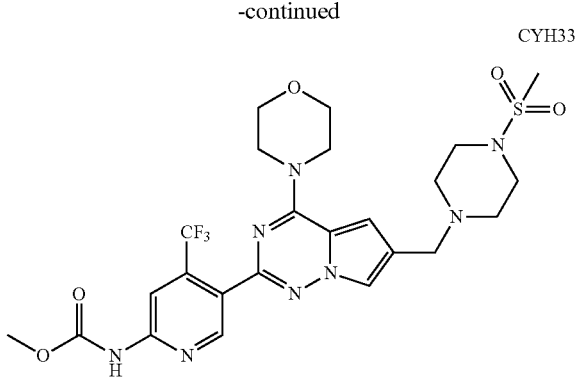

CYH33

The above-mentioned examples are merely illustrative of several embodiments of the present disclosure, which are described specifically and in detail, but it cannot be understood to limit the scope of the present disclosure. It should be noted that, for those ordinary skilled in the art, several variations and improvements may be made without departing from the concept of the present disclosure, and all of which are within the protection scope of the present disclosure. Therefore, the protection scope of the present disclosure shall be defined by the appended claims.

The invention claimed is:

1. A 7-substituted pyrrolo[2,1-f][1,2,4]triazine compound represented by a general formula I or a pharmaceutically acceptable salt thereof:

65

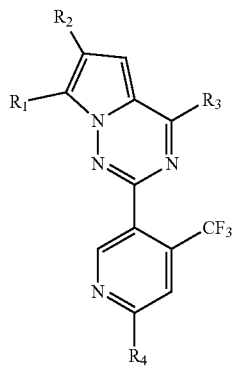

wherein,
$R_1$ is halogen, or $C_{1-6}$ alkyl or $C_{3-8}$ cycloalkyl which is unsubstituted or substituted with at least one substituent, wherein the substituent is halogen;
$R_2$ is: —C(OH)$R_5R_6$; —CO$C_{1-6}$ alkyl; —CN; or, unsubstituted or at least one substituent substituted $C_{1-6}$ alkyl, —CH$_2$NH—$C_{1-6}$ alkyl, —CH$_2$N($C_{1-6}$ alkyl)($C_{1-6}$ alkyl), —CH$_2$-(saturated heterocyclyl containing 1 to 2 heteroatoms and 3 to 6 carbon atoms), —CH$_2$-(saturated heterocyclyl containing 1 to 2 heteroatoms and 3 to 6 carbon atoms)-(saturated heterocyclyl containing 1 to 2 heteroatoms and 3 to 6 carbon atoms), —CH$_2$-(saturated spirocyclic group containing 1 to 2 heteroatoms and 4 to 12 carbon atoms), —CH$_2$-(saturated bridged ring group containing 1 to 2 heteroatoms and 3 to 12 carbon atoms)-(saturated heterocyclyl containing 1 to 2 heteroatoms and 3 to 6 carbon atoms), or —CH$_2$-(saturated bridged ring group containing 1 to 2 heteroatoms and 3 to 12 carbon atoms), wherein the substituent is halogen, —N($C_{1-4}$ alkyl)($C_{1-4}$ alkyl), —O—$C_{1-4}$ alkyl, —CN, —COOH, —CHO, —NHS(O)$_2$—$C_{1-4}$ alkyl, —N($C_{1-4}$ alkyl)C($C_{1-4}$ alkyl)($C_{1-4}$ alkyl)—CONH$_2$, =O, —OH, —S(O)$_2$N($C_{1-4}$ alkyl)($C_{1-4}$ alkyl), —S—$C_{1-4}$ alkyl, —S(O)$_2$—$C_{1-4}$ alkyl, —CO—$C_{3-6}$ cycloalkyl, oxetanyl, morpholinyl, $C_{3-6}$ cycloalkyl, —$C_{1-4}$ alkyl-N($C_{1-4}$ alkyl)($C_{1-4}$ alkyl), $C_{1-4}$ alkyl-O—$C_{1-4}$ alkyl which is unsubstituted or substituted with at least one methyl, —CONH$_2$ which is unsubstituted or substituted with at least one methyl, $C_{1-4}$ alkyl-CONH$_2$ which is unsubstituted or substituted with at least one methyl, —COO—$C_{1-4}$ alkyl which is unsubstituted or substituted with at least one methyl, —NH$_2$ which is unsubstituted or substituted with at least one methyl, —NHCO—$C_{1-4}$ alkyl which is unsubstituted or substituted with at least one methyl, —CO—$C_{1-4}$ alkyl which is unsubstituted or substituted with at least one substituent A, wherein the substituent A is hydroxyl or methyl, or $C_{1-4}$ alkyl which is unsubstituted or substituted with at least one substituent B, wherein the substituent B is —NH$_2$, —OCH$_3$, —CONH$_2$, —OH or —CF$_3$;
in $R_2$, the heteroatom is selected from at least one of N, O and S,
$R_5$ and $R_6$ are each independently hydrogen or $C_{1-6}$ alkyl;

66

$R_3$ is

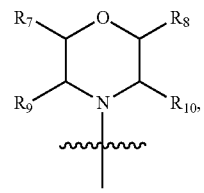

wherein $R_7$, $R_8$, $R_9$ and $R_{10}$ are each independently hydrogen or $C_{1-6}$ alkyl which is unsubstituted or substituted with at least one substituent, wherein the substituent is halogen or hydroxyl;
$R_4$ is —NH$_2$, —NHCONH$R_{11}$ or —NHCO$_2R_{12}$, wherein $R_{11}$ and $R_{12}$ are each independently $C_{1-6}$ alkyl, $C_{3-8}$ cycloalkyl or phenyl which is unsubstituted or substituted with at least one substituent selected from at least one of halogen and —C(O)O$R_{13}$, wherein $R_{13}$ is $C_{1-6}$ alkyl which is unsubstituted or substituted with at least one substituent, and the substituent in the $R_{13}$ is halogen.

2. The 7-substituted pyrrolo[2,1-f][1,2,4]triazine compound represented by the general formula I of claim 1 or a pharmaceutically acceptable salt thereof, wherein $R_1$ is halogen, or $C_{1-4}$ alkyl or $C_{3-6}$ cycloalkyl which is unsubstituted or substituted with at least one substituent.

3. The 7-substituted pyrrolo[2,1-f][1,2,4]triazine compound represented by the general formula I of claim 2 or a pharmaceutically acceptable salt thereof, wherein $R_1$ is —Cl, —F, methyl, trifluoromethyl or difluoromethyl.

4. The 7-substituted pyrrolo[2,1-f][1,2,4]triazine compound represented by the general formula I of claim 1 or a pharmaceutically acceptable salt thereof, wherein $R_2$ is: —C(OH)$R_5R_6$; —CO$C_{1-4}$ alkyl; —CN; or, unsubstituted or at least one substituent substituted $C_{1-4}$ alkyl, —CH$_2$NH—$C_{1-4}$ alkyl, —CH$_2$N($C_{1-4}$ alkyl)($C_{1-4}$ alkyl), —X-(saturated four- to six-membered heterocyclyl containing 1 to 2 heteroatoms), —X-(saturated four- to six-membered heterocyclyl containing 1 to 2 heteroatoms)-(saturated four- to six-membered heterocyclyl containing 1 to 2 heteroatoms), —X-(saturated bicyclic spirocyclic group containing 1 to 2 heteroatoms and 4 to 8 carbon atoms), —X-(saturated bicyclic bridged ring group containing 1 to 2 heteroatoms and 3 to 8 carbon atoms)-(saturated four- to six-membered heterocyclyl containing 1 to 2 heteroatoms), or —X-(saturated bicyclic bridged ring group containing 1 to 2 heteroatoms and 3 to 8 carbon atoms), wherein X is CH$_2$, and wherein the heterocyclyl, spirocyclic group and bridged ring group are connected to X via an N atom, $R_5$ and $R_6$ are each independently hydrogen or $C_{1-4}$ alkyl.

5. The 7-substituted pyrrolo[2,1-f][1,2,4]triazine compound represented by the general formula I of claim 4 or a pharmaceutically acceptable salt thereof, wherein the substituent in $R_2$ is —F, —Cl, —Br, —I, —CH$_3$, —CH$_2$CH$_3$, —CH$_2$CH(CH$_3$)$_2$, —CH$_2$NH$_2$, —CH$_2$N(CH$_3$)$_2$, —CH$_2$CH$_2$NH$_2$, —CH$_2$CH$_2$N(CH$_3$)$_2$, —CH$_2$OH, —CH$_2$OCH$_3$, —CH$_2$CH$_2$OH, —C(CH$_3$)$_2$OH, —C(CH$_3$)(CF$_3$)OH, —C(CF$_3$)$_2$OH, —C(CH$_3$)$_2$OCH$_3$, —C(CH$_3$)$_2$NH$_2$, —CH$_2$C(CH$_3$)$_2$OH, —CH(OH)CH(CH$_3$)$_2$, —C(CH$_3$)$_2$CH$_2$OH, —C(CH$_3$)$_2$CH$_2$OCH$_3$, —CN, —CF$_3$, —CO$_2$H, —CHO, —COCH$_3$, —CO$_2$CH$_3$, —CO$_2$C(CH$_3$)$_3$, —COCH$_2$OH, —COC(OH)(CH$_3$)$_2$, —COCH(OH)CH$_3$, —CONH$_2$, —CONHCH$_3$, —CON(CH$_3$)$_2$, —CH$_2$CONH$_2$, —CH$_2$CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, =O, —OH, —OCH₃, —S(O)₂N(CH₃)₂, —SCH₃, —S(O)₂CH₃, —C(O)-cyclopropyl, cyclopropyl, cyclobutyl, oxetanyl or morpholinyl.

6. The 7-substituted pyrrolo[2,1-f][1,2,4]triazine compound represented by the general formula I of claim 1 or a pharmaceutically acceptable salt thereof, wherein $R_2$ is

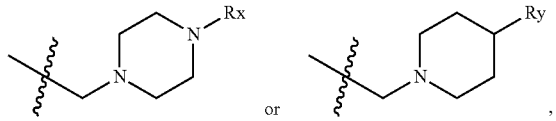

or

Rx and Ry are each —N(CH₃)₂, —S(O)₂CH₃ or $C_{1-4}$ alkyl, wherein the $C_{1-4}$ alkyl is unsubstituted or substituted with at least one substituent, the substituent is halogen, hydroxyl, —CONH₂, —CF₃, amino or —OCH₃.

7. The 7-substituted pyrrolo[2,1-f][1,2,4]triazine compound represented by the general formula I of claim 1 or a pharmaceutically acceptable salt thereof, wherein $R_2$ is

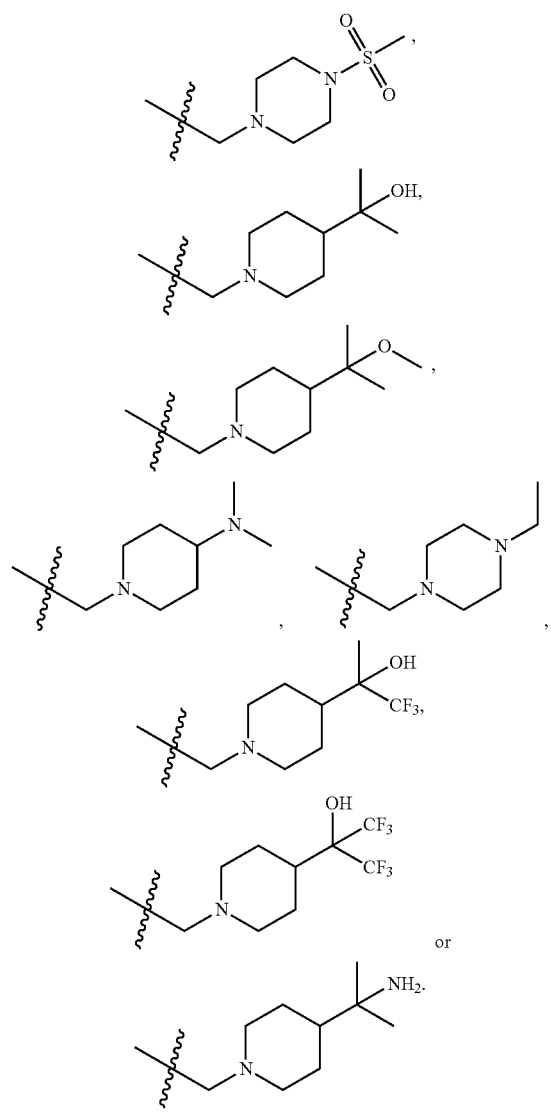

8. The 7-substituted pyrrolo[2,1-f][1,2,4]triazine compound represented by the general formula I of claim 1 or a pharmaceutically acceptable salt thereof, wherein $R_3$ is

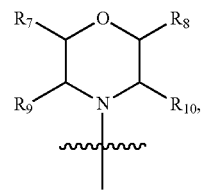

and wherein $R_7$, $R_8$, $R_9$ and $R_{10}$ are each independently hydrogen or $C_{1-4}$ alkyl.

9. The 7-substituted pyrrolo[2,1-f][1,2,4]triazine compound represented by the general formula I of claim 8 or a pharmaceutically acceptable salt thereof, wherein $R_3$ is morpholinyl or (S)-3-methylmorpholinyl.

10. The 7-substituted pyrrolo[2,1-f][1,2,4]triazine compound represented by the general formula I of claim 1 or a pharmaceutically acceptable salt thereof, wherein $R_4$ is —NH₂, —NHCONHR₁₁ or —NHCO₂R₁₂, wherein $R_{11}$ and $R_{12}$ are each independently $C_{1-4}$ alkyl, $C_{3-6}$ cycloalkyl or phenyl which is unsubstituted or substituted with at least one substituent selected from at least one of fluoro, chloro, bromo and —C(O)OR₁₃, wherein $R_{13}$ is $C_{1-4}$ alkyl.

11. The 7-substituted pyrrolo[2,1-f][1,2,4]triazine compound represented by the general formula I of claim 10 or a pharmaceutically acceptable salt thereof, wherein $R_{11}$ and $R_{12}$ are each independently methyl, ethyl, isopropyl, cyclopropyl, phenyl, -Ph-CO₂Et-p or 4-fluorophenyl.

12. The 7-substituted pyrrolo[2,1-f][1,2,4]triazine compound represented by the general formula I of claim 1 or a pharmaceutically acceptable salt thereof, wherein the compound has a structure represented by one of the following general formulas:

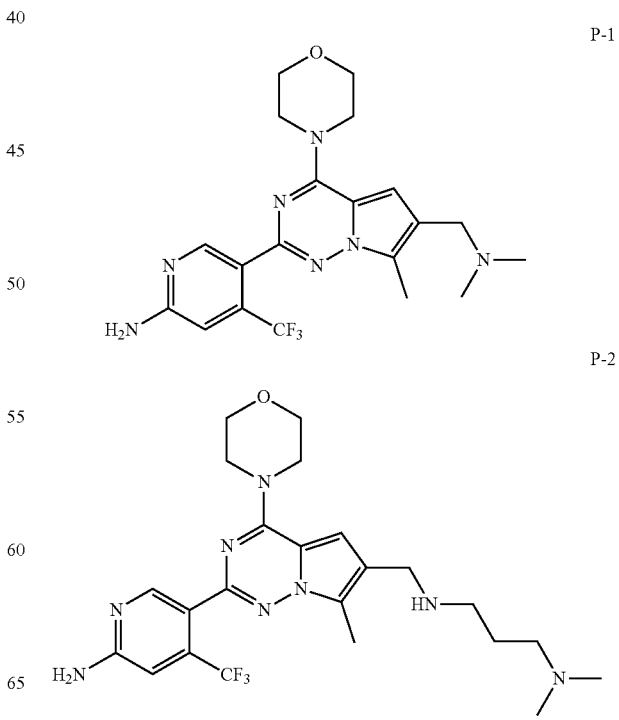

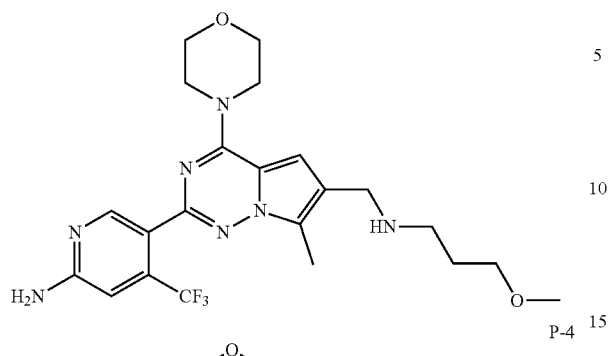
P-3
P-4
P-5
P-6
P-7
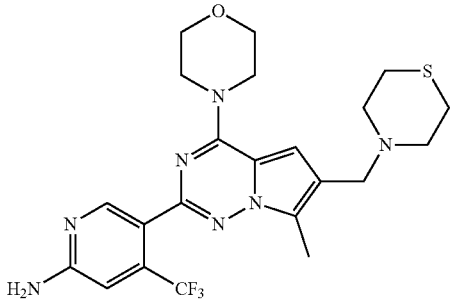
P-8
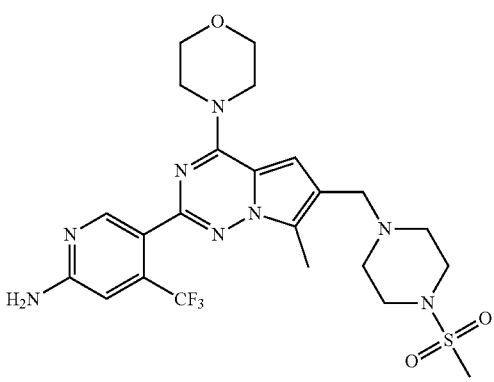
P-9
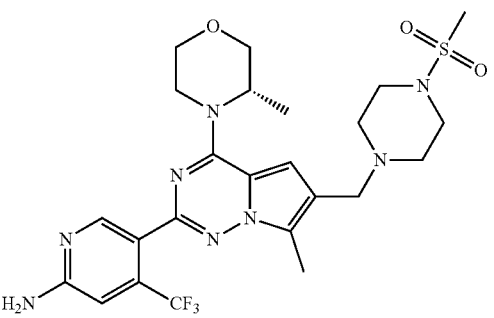
P-10
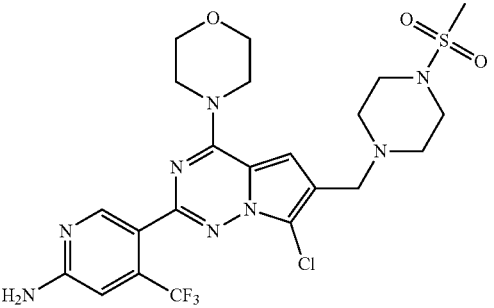
P-11

P-12
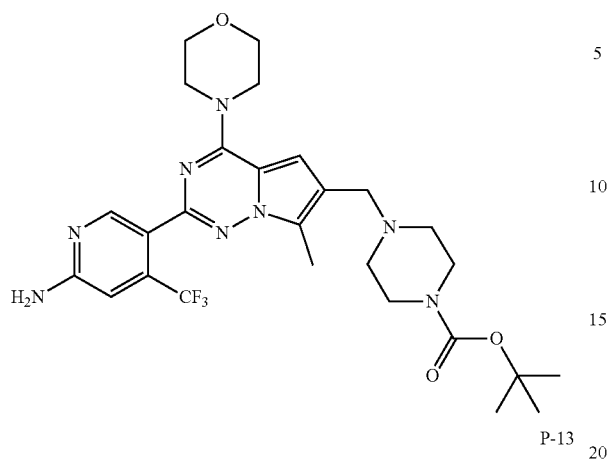
P-13
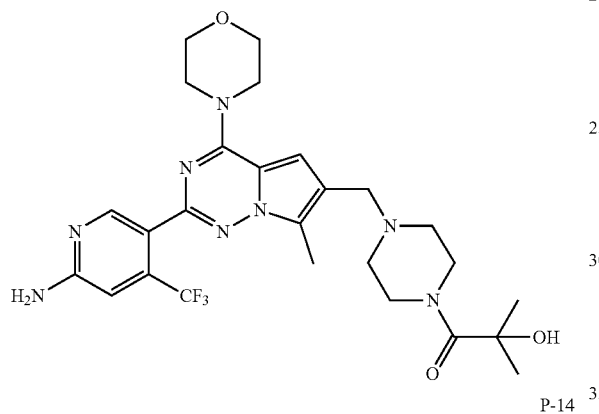
P-14
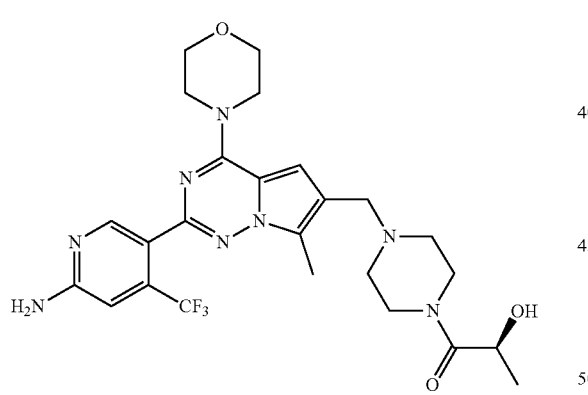
P-15
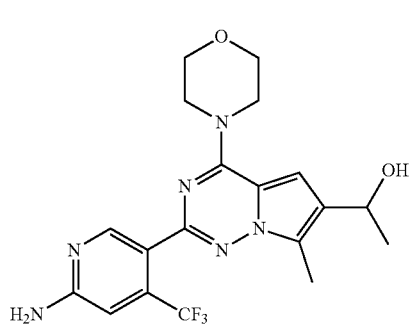
P-16
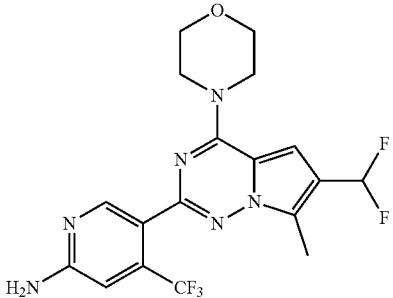
P-17
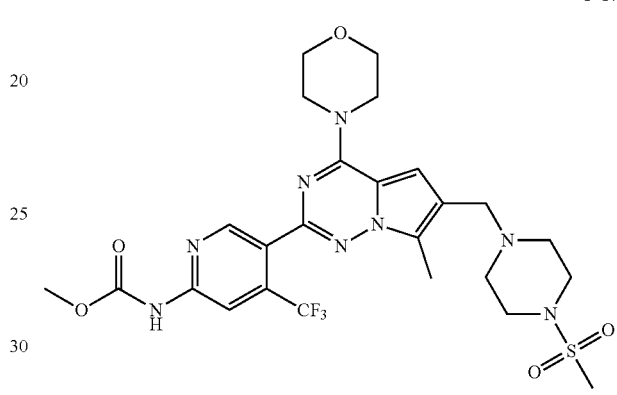
P-18
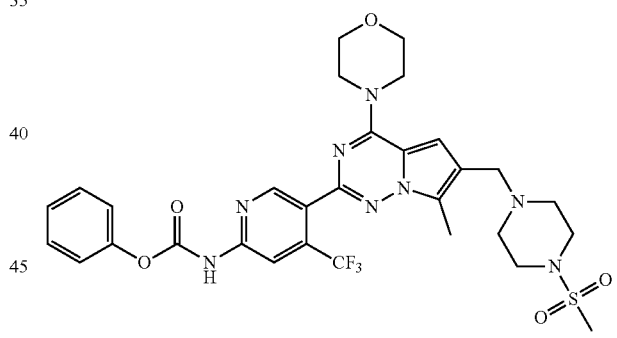
P-19
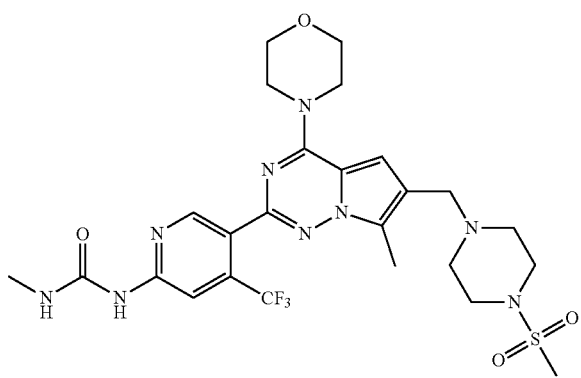

-continued
P-20
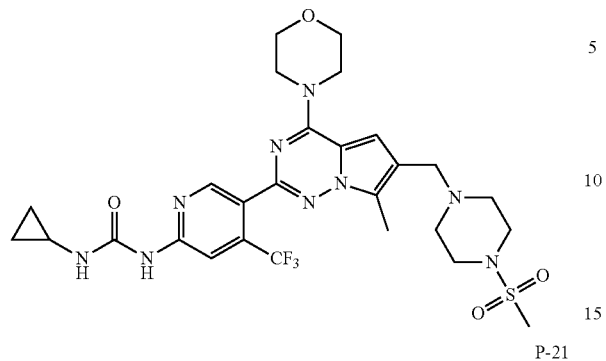
P-21
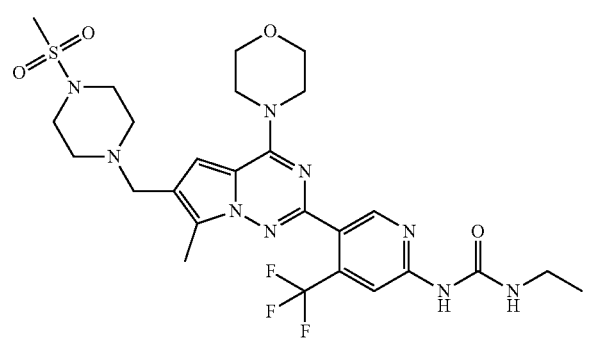
P-22
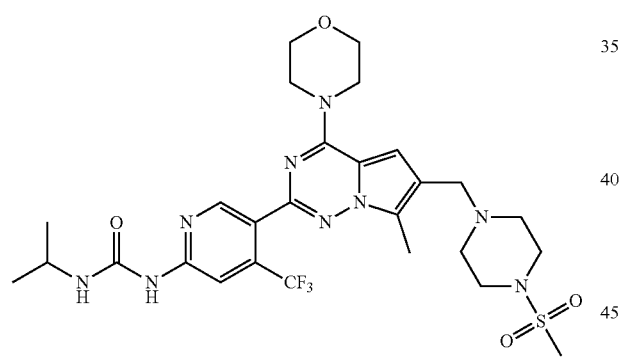
P-23
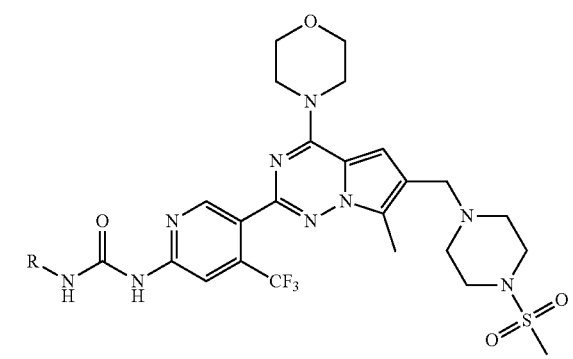
R = p-F-Ph
-continued
P-24
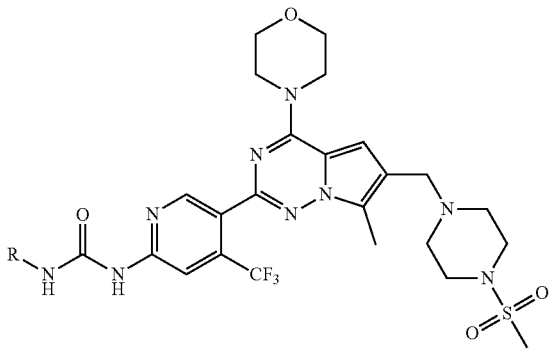
R = p-EtOCOPh
P-25
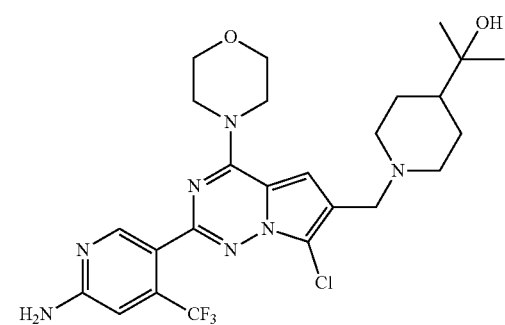
P-26
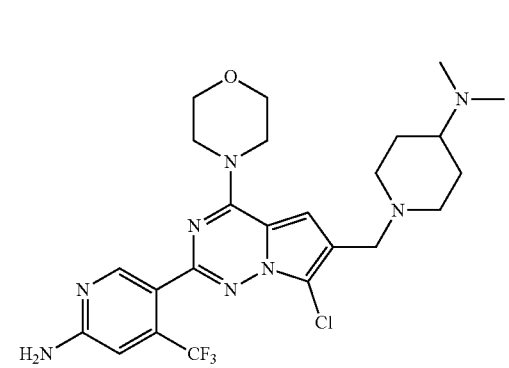
P-27
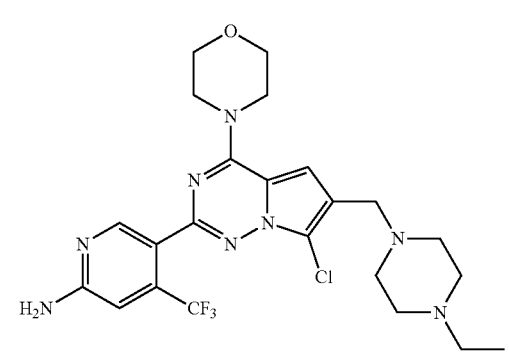

-continued
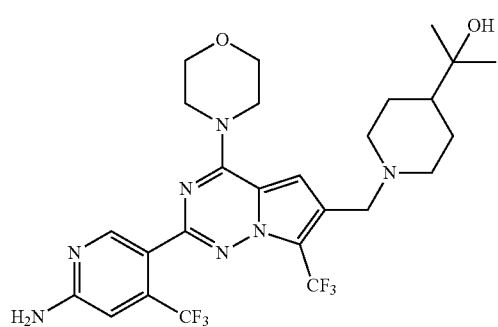
P-28
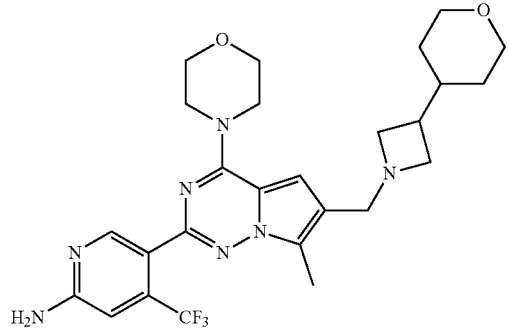
P-29
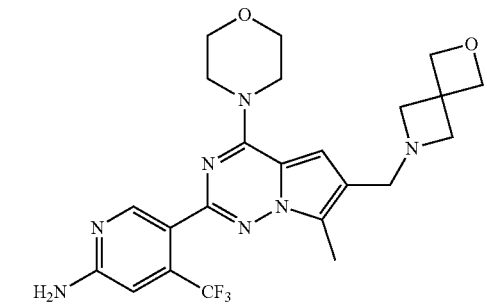
P-30
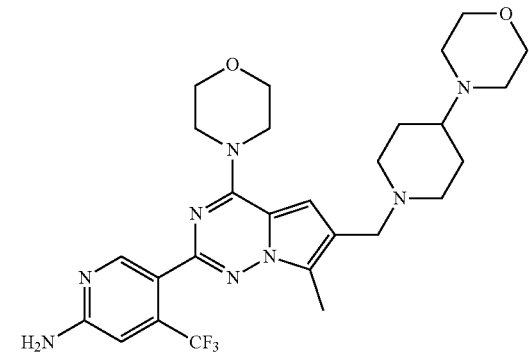
P-31
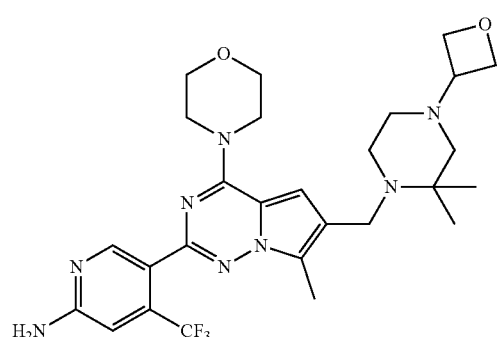
P-32
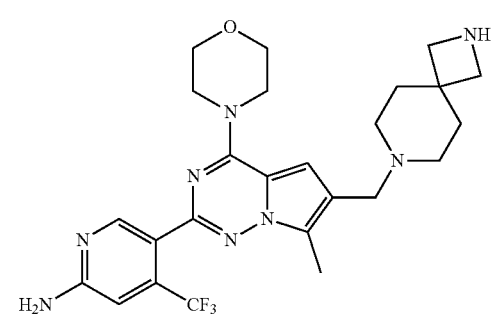
P-33
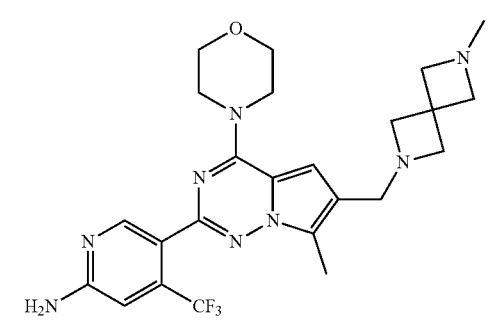
P-34
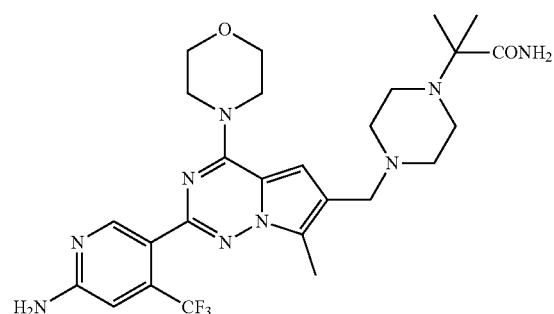
P-35
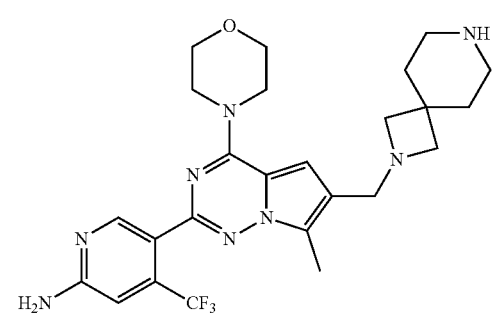
P-36

P-37
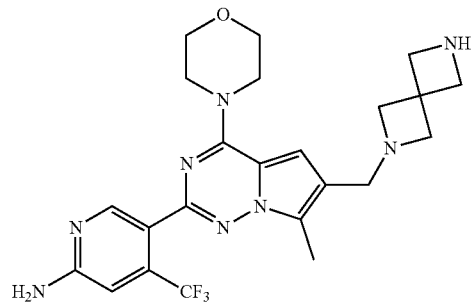
P-38
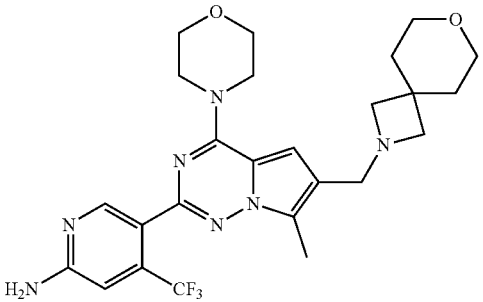
P-39
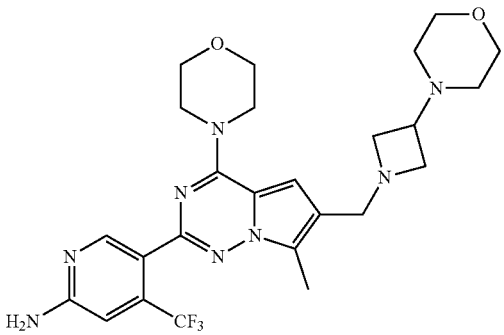
P-40
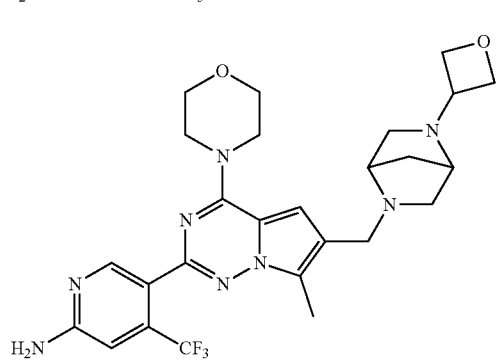
P-41
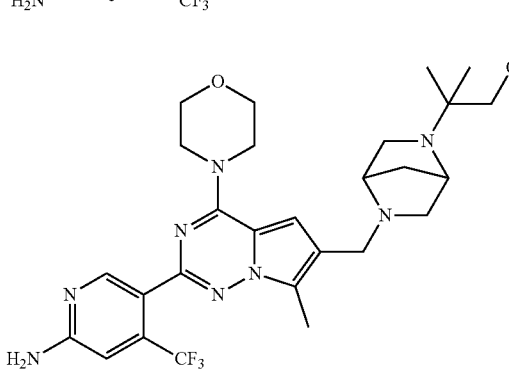
P-42
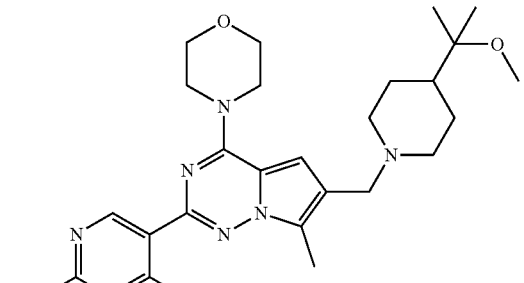
P-43
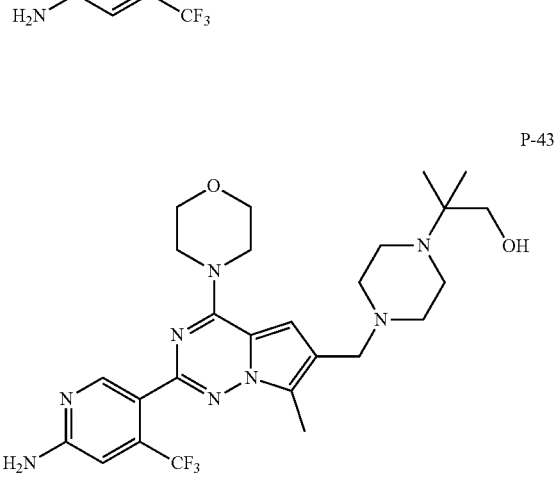
P-44
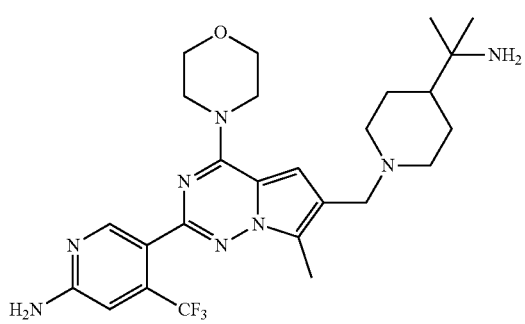
P-45
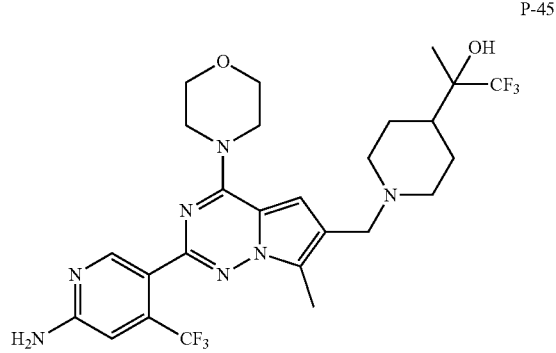

-continued
P-46
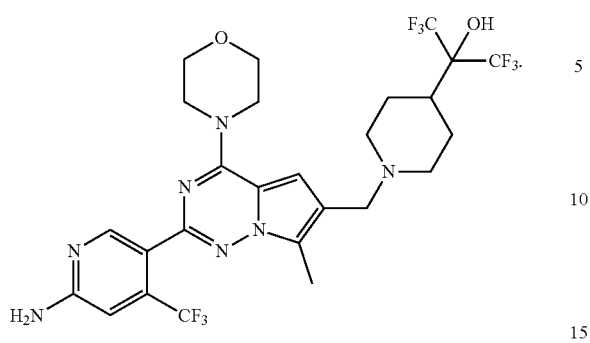
13. A method of inhibiting an activity of a PI3K kinase, the method comprising reacting the 7-substituted pyrrolo[2,1-f][1,2,4]triazine compound represented by the general formula I of claim 1 or a pharmaceutically acceptable salt thereof with the PI3K kinase.
14. The method according to claim 13, wherein the PI3K kinase is a PI3Kδ kinase.
* * * * *